(12) United States Patent
Vígh et al.

(10) Patent No.: US 7,745,465 B2
(45) Date of Patent: Jun. 29, 2010

(54) METHOD OF ENHANCING CELLULAR PRODUCTION OF MOLECULAR CHAPERONE, HYDROXYLAMINE DERIVATIVES USEFUL FOR ENHANCING THE CHAPERONE PRODUCTION AND THE PREPARATION THEREOF

(75) Inventors: László Vígh, Szeged (HU); Péter Literáti Nagy, Budapest (HU); Jenö Szilbereky, Budapest (HU); László Ürögdi, Budapest (HU); Andrea Jednákovits, Budapest (HU); László Jaszlits, Budapest (HU); Katalin Bíró, Budapest (HU); Ede Márványos, Budapest (HU); Mihály Barabás, Budapest (HU); Erzsébet Hegedüs, Budapest (HU); László Korányi, Budapest (HU); Mária Kürthy, Budapest (HU); Gábor Balogh, Szeged (HU); Ibolya Horváth, Szeged (HU); Zsolt Török, Szeged (HU); Éva Udvardy, Budapest (HU); György Dormán, Budapest (HU); Dénes Medzihradszky, Budapest (HU); Bea Mézes, Budapest (HU); Eszter Kovács, Szeged (HU); Ernö Duda, Budapest (HU); Beatrix Farkas, Szeged (HU); Attila Glatz, Szeged (HU)

(73) Assignee: CytRx Corporation, Los Angeles, CA (US)

( * ) Notice: Subject to any disclaimer, the term of this patent is extended or adjusted under 35 U.S.C. 154(b) by 1221 days.

(21) Appl. No.: 10/618,162

(22) Filed: Jul. 10, 2003

(65) Prior Publication Data

US 2004/0067940 A1    Apr. 8, 2004

Related U.S. Application Data

(62) Division of application No. 08/860,582, filed as application No. PCT/HU96/00064 on Nov. 1, 1996, now Pat. No. 6,653,326.

(30) Foreign Application Priority Data

| Nov. 2, 1995 | (HU) | ................................... 95 03141 |
| Feb. 9, 1996 | (HU) | ................................... 95 03141/3919 |
| Oct. 4, 1996 | (HU) | ................................... 95 03141/29820 |

(51) Int. Cl.
*A61K 31/445* (2006.01)
*A61K 31/44* (2006.01)
*A01N 37/00* (2006.01)

(52) U.S. Cl. ............... 514/318; 514/331; 514/356; 514/507; 514/508; 514/633

(58) Field of Classification Search ............... 514/316, 514/331, 356, 507, 508, 633
See application file for complete search history.

(56) References Cited

U.S. PATENT DOCUMENTS

| 4,404,384 | A | 9/1983 | Gebert et al. ............... 544/392 |
| 5,147,879 | A | 9/1992 | Nagy et al. ................ 514/318 |
| 5,239,077 | A | 8/1993 | Bertok et al. .............. 546/193 |
| 5,278,309 | A | 1/1994 | Bertok et al. .............. 546/193 |
| 5,296,606 | A | 3/1994 | Nagy et al. ................ 546/193 |
| 5,334,600 | A | 8/1994 | Van Duzer et al. | |

FOREIGN PATENT DOCUMENTS

| DE | WO-A-90-08131 | 1/1991 |
| DE | WO-A-95-30649 | 2/1996 |
| GB | 1 540 028 | 2/1979 |
| GB | 1582 029 | 12/1980 |
| HU | 216830 | 11/1994 |

OTHER PUBLICATIONS

Sorensen et al., Microbial Cell Factories 4:1, pp. 1-8, (2005).*
CiteSeer Abstract only 1 page (2001) Biogerontology.*
Vachani oncolink non-Hodgkin's (www.onlink.coml-6, (2007)).*
MSDS HyperGlossary, 1 pg (2006).*
bystress.com pp. 1-3 (2006).*
Roberts et al. J. bacteriology (1996), 1829-1841.*
Yoo et al., Electrophoresis (2001), 22, 1233-1241.*
Simone. In "Cecil Textbook of Medicine", 20th Edition (ed. J.C. Bennett), vol. 1 (1997) 1005-1010.*

* cited by examiner

*Primary Examiner*—Michael G Hartley
*Assistant Examiner*—Shirley V Gembeh
(74) *Attorney, Agent, or Firm*—Ropes & Gray LLP; Barbara A. Ruskin; Carl A. Morales

(57) ABSTRACT

A method of increasing expression of a molecular chaperon by a cell and/or enhancing the activity of a molecular chaperon in cells is provided. The method comprises treating a cell that is exposed to a physiological stress which induces expression of a molecular chaperon by the cell with an effective amount of a certain hydroxylamine derivative to increase the stress. Alternatively, an hydroxylamine derivative can be administrated to a cell before it is exposed to a physiological stress which induces expression of a molecular chaperon by the cell. Preferably, the cell to which an hydroxylamine derivative is administered is an eukaryotic cell. The hydroxylamine derivative corresponds to the formulae (I) or (II).

The invention also provides novel hydroxylamine derivatives falling within the scope of the formulae (I) and (II) as well as pharmaceutical and/or cosmetical compositions comprising the said compounds.

11 Claims, 28 Drawing Sheets

US 7,745,465 B2

METHOD OF ENHANCING CELLULAR PRODUCTION OF MOLECULAR CHAPERONE, HYDROXYLAMINE DERIVATIVES USEFUL FOR ENHANCING THE CHAPERONE PRODUCTION AND THE PREPARATION THEREOF

CROSS REFERENCE TO RELATED APPLICATION

This application is a division of U.S. patent application Ser. No. 08/860,582, filed Dec. 7, 1999 now U.S. Pat. No. 6,653, 326, which bases priority from PCT Application No. PCT/HU96/00064, filed Nov. 1, 1996, which claims priority from Hungarian Patent Application No. P 95 03141, filed Nov. 2, 1995, Hungarian Patent Application No. P 95 03141/3919, filed Feb. 9, 1996, and Hungarian Patent Application No. P 95 03141/29820, filed Oct. 4, 1996.

BACKGROUND OF THE INVENTION

Molecular chaperons are proteins which mediate protein folding. They bind non-covalently to exposed surfaces of proteins that are newly synthesized or are denatured or misfolded, and assist them to fold into correct conformations. Molecular chaperons are also involved in a number of cellular processes such as protein synthesis, protein translocation and DNA replication.

Molecular chaperons include heat shock proteins, which are proteins whose expression increases significantly in cells following an exposure to unusually high temperature (heat shock) or an exposure to a wide variety of physiological stresses. This increase in the molecular chaperon expression in turn provides cells with protection against the adverse effects of hyperthermia, as demonstrated by the thermotolerance of cells for otherwise lethal temperatures if the cells are pre-conditioned by a brief exposure to high temperature.

Physiological stresses inducing heat shock protein expression include a wide variety of pathological conditions associated with many diseases. The synthesis of heat shock proteins in cells exposed to such stresses, indicates the protection of the cell against the physiological stresses, like also in the case of the heat shock response.

One such pathological condition associated with induction of molecular chaperons is ischemic injury. Ischemic injury to tissues results from deterioration of blood supply for any possible. For instance, prolonged coronary occlusion causes severe damage to myocardium, leading to myocardial necrosis and jeopardizing the chances for recovery even if the blood flow is restored. In brain, to significant damages may frequently be caused by ischemia, leading to death of the brain-tissue.

It was observed that the amount of heat shock protein hsp70 increased in the myocardium during ischemia leading to necrosis even if the duration of ischemia is short. In these cases, likewise in a heat shock, the enhanced hsp70 content of the cells protects the same against the consequences of a next ischemia, which would otherwise cause necrosis (DAS, D. K., et al. Cardiovascular Res.: 578, 1993). It has also been observed when rat cells in culture were subjected to ischemia, J. Clin. Invest., 93: 759-767 (1994)). Accordingly, heat shock proteins synthesized by myocardial cells provide protection against ischemic injuries.

The situation in brain-tissue is similar, wherein cerebral ischemia results in increased expression of heat shock protein in the brain tissue. Experiments have also proved that pre-treatment of animals with sub-lethal ischemia induces heat stress protein (hsp70) and protects the brain against more severe subsequent ischemic insult. (Simon, et al., Neurosci. Lett., 163:135-137 (1993)).

Yet another example of physiological stress on tissues and organs associated with molecular chaperon induction is provided by inflammatory diseases. Inflammation is a non-specific response of host cells to entry of foreign material such as in case of infection by various bacterial and viral pathogens, and involves aggregation and activation of leukocytes to the injury site, which results in production and release of high levels of reactive oxygen species and cytokines. These cytokines and reactive oxygen radicals attack the pathogen, but also damage the host tissues (Jaquier.Sarlin, Experientia, 50: 1031-1038/1994/). It is believed that as a protection against these toxic mediators of inflammation, the host tissues increase production of molecular chaperons. Molecular chaperons thus produced protect host cells from damages caused by reactive oxygen species and protect cells from cytotoxicity of TNF and other cytokines and reactive oxygen radicals. In animal studies, it has been demonstrated the pre-exposure of an animal to heat shock, with resulting increase of a heat shock protein (hsp70) expression, resulted in remarkable decrease in pulmonary inflammation. Accordingly, molecular chaperons serve anti-inflammatory function.

The above examples illustrate ability of molecular chaperons to protect cells against various physiological stresses disturbing cellular homeostatic balance and causing injury to cells. Molecular chaperons have also been shown to be advantageous in treating neoplasms. For example, it has been reported that when tumor cells are transfixed with a gene encoding a molecular chaperon (65 kd hsp), they lose or show decrease in their tumorigenicity (PCT Application No. PCT/GB93/02339). Furthermore, it has also been reported that tumor cells, in response to heat stress, express molecular chaperons in increased amount. However, they are present not in cyto-plasm, but on the surface of cell membranes. (Ferrarini, M. et al Int. J. Cancer, 51:613-619/1992/). Increased presence of molecular chaperones on cell surfaces correlates with increased sensitivity of NK (natural killer) cells toward the tumor cells, allowing better targeting, infiltrating, and killing of the tumor cells by NK cells (Kurosawa S. et aL Eur. J. Immunol. 23:1029/1993/).

In view of the advantages associated with increased molecular chaperon expression in cells, a method which increased such expression or increased activity of molecular chaperons would be highly desirable.

SUMMARY OF THE INVENTION

The invention relates to methods for increasing expression or enhancing activity of molecular chaperons by a cell. In particular, according to one non-limiting embodiment of the invention, a method is provided comprising treating a cell that is exposed to a physiological stress with an effective amount of a chemical compound during, before or after the physiological stress which increases expression of a molecular chaperon in the cell beyond the amount induced by the physiological stress, wherein the chemical compound is a hydroxylamine derivative the tautomeric forms of which are represented by formulae (I) and (II), or its salt, including the optically active stereoisomers thereof, wherein A is an alkyl, substituted alkyl, aralkyl, aralkyl substituted in the aryl and/or in the alkyl moiety, aryl, substituted aryl, heteroaryl or substituted heteroaryl group, Z is a covalent bond, oxygen or $=NR^3$ wherein $R^3$ is selected from the group consisting of hydrogen, an alkyl, substituted alkyl, aryl, substituted aryl, aralkyl, or aralkyl substituted in the aryl and/or in the alkyl moiety, R is an alkyl or substituted alkyl, X in the tautomer of formula (I) is halogen or a substituted hydroxy or amino, monosubstituted amino or disubstituted amino group and X in the tautomer of formula (II) is oxygen, imino or substituted imino group and R' is hydrogen, an alkyl, substituted alkyl, aryl, substituted aryl, aralkyl, aralkyl having substituted aryl and/or alkyl moiety, acyl or substituted acyl group, and the compounds of formula (I) optionally contain intramolecular ring structures formed by coupling X and a reactive substituent.

An other non-limiting embodiment of the invention is the method of enhancing the activity of a molecular chaperon in a cell exposed to a physiological stress which comprises administering an effective amount of a hydroxylamine derivative of structure (I) or (II), as described above. Thus, the activity of molecular chaperon is increased beyond the amount induced by the physiological stress alone. In either of these methods, it is preferred that the cell to which the hydroxylamine derivative is administered to is an eukaryotic cell.

According to the invention eucaryotic cells are treated with the hydroxylamine derivatives as defined above.

Another object of the invention is the method of treatment or possible prevention of diseases connected with functioning of the chaperon system or associated with damages of the cell- or cell-organellum membrane, wherein for suppressing the pathological condition effective amount of a hydroxylamine derivative of the formula (I) or (II) is administered to the host organism.

Still another object of the invention is the use of the hydroxylamine derivatives of the formula (I) or (II) or the salts thereof in the preparation of pharmaceutical compositions which can be used in the treatment of cardiovascular, vascular, cerebral, tumorous diseases, diseases of the skin and/or mucous membrane or those of the epithelial cells of renal tubules, as well as in the preparation of cosmetical compositions.

The invention further relates to novel hydroxylamine derivatives possessing a wide range of biological effect and are useful for enhancing the level of molecular chaperon in organisms or the activity of the said molecular chaperons and for the preparation of pharmaceutical and cosmetical compositions applicable to this purpose.

A further object of the invention is represented by the pharmaceutical and cosmetical compositions which comprise novel hydroxylamine derivatives together with carriers and auxiliaries generally acceptable in such compositions.

The present invention is based, at least in part, on an unexpected discovery that hydroxylamine derivatives having structures as described above, when used in the treatment of cells, are capable of increasing the amount of molecular chaperons produced by that cell or enhancing the activity thereof. This effect is particularly great when the cell is under physiological stress which induces molecular chaperon expression. In such cases, the chemical compound enhances expression of molecular chaperons by the cell beyond that amount induced by the physiological stress alone. This discovery is significant in view of the role molecular chaperons play in cells defending themselves against pathological effects of various diseases. Thus, if a compound is able to increase the amount or enhance the activity of molecular chaperons being expressed by cells, this allows the cells to be protected against the deleterious effects of the diseases and to repair damages caused by them.

DETAILED DESCRIPTION OF THE INVENTION

Figure 1:
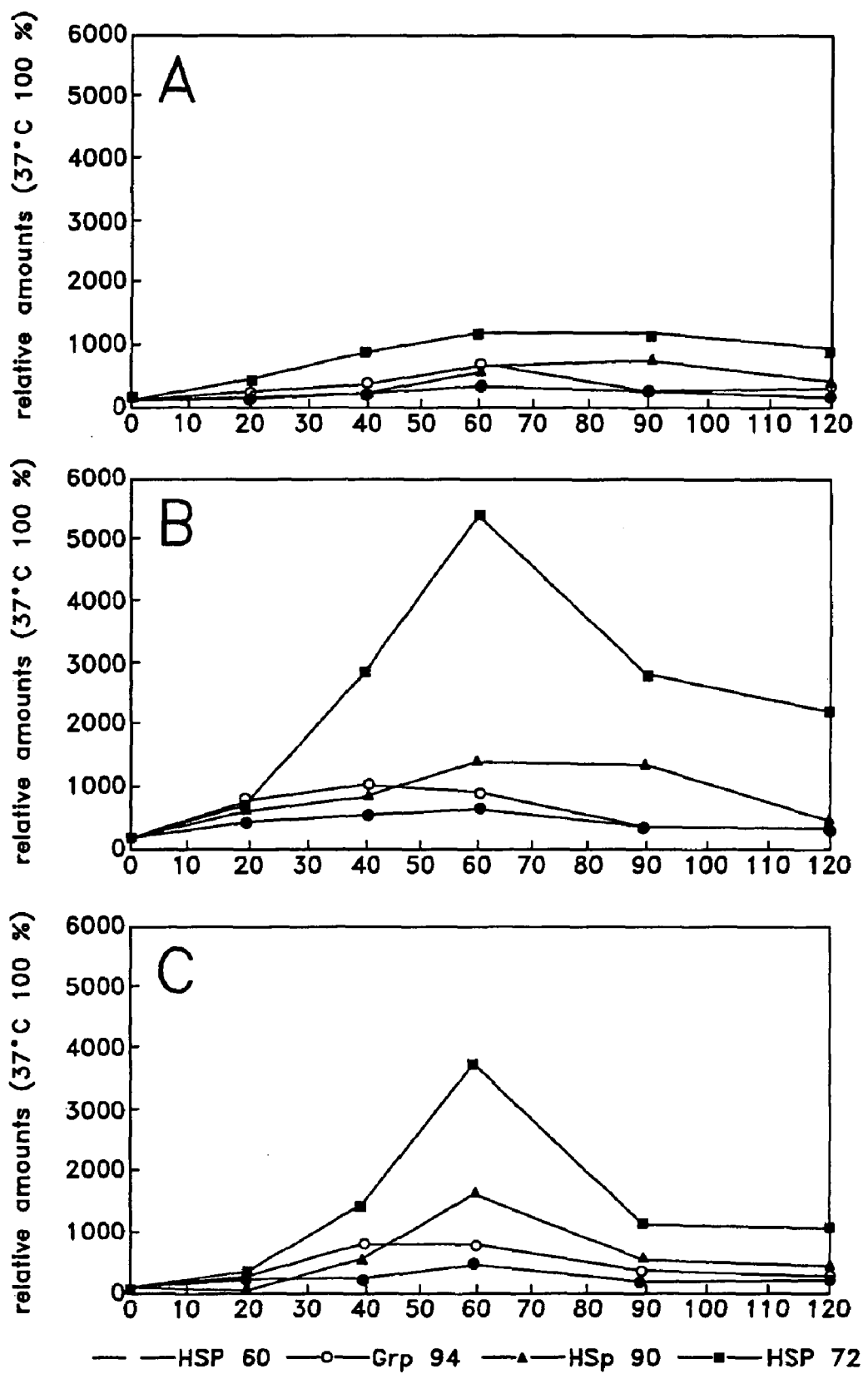
FIG. 1 shows the changes in hsp level on H9c2 rat myocardium exposed to heat shock by the effect of treatment with N-[2-hydroxy-3-(1-piperidinyl)-propoxy]3-pyridinecarboximidoyl chloride maleate. This compound is labeled B on the Figures and referred to as compound B in the followings as well.

The entire disclosure of U.S. patent application Ser. No. 08/860,582, filed Dec. 7, 1999, is expressly incorporated by reference herein.

Hydroxylamine Derivatives of the Invention

Hydroxylamine derivatives, the tautomeric forms of which are represented by formulae (I) and (II), can be used in accordance with the invention described herein. In the above formulae A is an alkyl, substituted alkyl, aralkyl, aralkyl substituted in the aryl and/or in the alkyl moiety, aryl, substituted aryl, heteroaryl or substituted heteroaryl group, Z is a covalent bond, oxygen or $=NR^3$ wherein $R^3$ is selected from the group consisting of hydrogen, an alkyl, substituted alkyl, aryl, substituted aryl, aralkyl and aralkyl substituted in the aryl and/or in the alkyl moiety, R is an alkyl or substituted alkyl, X in the tautomer of formula (I) is halogen or a substituted hydroxy or amino, monosubstituted amino or disubstituted amino group and X in the tautomer of formula (II) is oxygen, imino or substituted imino group and R' is hydrogen, an alkyl, substituted alkyl, aryl, substituted aryl, aralkyl, aralkyl having substituted aryl or alkyl moiety, acyl or substituted acyl group, and the compounds of formula (I) optionally contain intramolecular ring structures formed by coupling X and a reactive substituent.

Where alkyl" is mentioned, it means straight or branched alkyl groups comprising short and long chains as well.

The typical number of carbon atoms of a preferred short chain alkyl group ranges from 1 to 8 and might be methyl-, ethyl-, propyl-, isopropyl-, butyl-, isobutyl-, sec-butyl-, pentyl-, tert-pentyl-, hexyl-, heptyl-, and octyl-groups and the like, more preferably 1 to 6 and might be methyl-, ethyl-, propyl-, isopropyl-, butyl-, isobutyl-, sec-butyl-, pentyl-, tert-pentyl-, and hexyl-groups.

The typical number of carbon atoms of a preferred long chain alkyl group ranges from 9 to 21 and might be nonyl-, decyl-, undecyl-, dodecyl-, tridecyl-, tetradecyl-, pentadecyl-, hexadecyl-, heptadecyl, octadecyl-, nonadecyl-, eicosyl- and heneicosyl-groups and the like, more preferably from 9 to 17 and might be nonyl-, decyl-, undecyl-, dodecyl-, tridecyl, tetradecyl-, pentadecyl-, hexadecyl-, and heptadecyl-groups.

A preferred cycloalkyl group means a cycloalkyl group having a short cycloalkyl chain ranges from 3 to 8 and might be cyclopropyl-, cyclobutyl-, cyclopentyl-cyclohexyl-, cycloheptyl- and cyclooctyl-groups and the like, more preferably from 3 to 7 and might be cyclopropyl-, cyclobutyl-, cyclopentyl-, cyclohexyl- and cycloheptyl-groups.

Optionally substituted aryl or alkyl means an aryl- or alkyl group having one or more substituents such as cyano-, hydroxyl-, short chain alkyl- (e.g. methyl-, ethyl-, propyl-, isopropyl-, butyl-, isobutyl-, sec-butyl-, pentyl-, tert-pentyl-, hexyl-, heptyl-, octyl- and the like), short chain alkoxy- (e.g. methoxy-, ethoxy-, propoxy-, isopropoxy-, butoxy-, isobutoxy, sec-butoxy-, tert-butoxy-, pentyloxy-, tert-pentyl-oxy-, hexyloxy- and the like), aryl- (e.g. phenyl-, naphthyl-, and the like), nitro-, amino-, mono-(short chain alkyl)-substituted amino- (e.g. methyl, ethyl, propyl, isopropyl, tertbutyl)-amino and the like, di-(short chain alkyl)-substituted amino- (e.g. dimethylamino-, diethylamino-, dipropylamino-, diisopropylamino-, dibutylamino-, dipentylamino-, dihexylamino- and the like), monohalogen-, dihalogen- or trihalogen (short chain)-alkyl (e.g. chloromethyl, 2,2-dichloroethyl, trifluoromethyl- and the like) group or halogen atom (e.g. fluoro-, chloro-, bromo-, and iodine atom) and the like as well.

A preferred aralkyl group means a short chain alkyl group as written above, substituted with one or more (optionally substituted) aryl groups and might be benzyl-, benzhydryl-, trityl-, 1-phenyl-ethyl-, 2-phenylethyl-, 2-benzhydryl-ethyl-, 3-phenylpropyl-, 1-methyl-2-phenyl-ethyl-, 1-phenylbutyl-, 4-tritylbutyl-, 1.1-dimethyl-2-phenylethyl-, 4-phenylbutyl-, 5-phenylpentyl-, 6-phenylhexyl-groups and the like, more preferably lower alkyl group from 1 to 4 carbon atom, substituted with a phenyl group and might be benzyl-, 1-phenylethyl-, 2-phenylethyl-, and 1-methyl-2-phenylethyl groups. A preferred aryl group might be phenyl-, naphthyl-, pentalenyl-, anthracenyl-groups and the like, more preferably phenyl- and naphthyl groups.

A preferred 3-8 membered, more preferably 5-8 membered, N-containing saturated heterocyclic group means a saturated heterocyclic group containing 1-4 nitrogen atoms and might be aziridinyl-, azetidinyl-, oxaziranyl-, pyrrolidinyl-, imidazolidinyl-, pyrazolidinyl-, perhydro-tiazolyl-, perhydro-isoxazolyl-, piperidinyl-, piperazinyl-, perhydro-pyrimidinyl-, perhydro-pyridazinyl-, morpholinyl-, perhidro-1, H-azepinyl-groups and the like.

A preferred heteroaryl group means an unsaturated, 3-8 membered, more preferably 5-6 membered, 1-4 N-containing unsaturated hetero-monocyclic group and might be pyrrolyl-, pyrrolinyl-, imidazolyl-, pyrazolyl-, pyridyl-group and its N-oxide, pirimidinyl-, pyrazinyl-, pyridazinyl-, triazolyl-, tetrazolyl-, dihydrotriazinyl-group and the like; or means unsaturated, I-5 N-containing condensed heterocyclic group and might be indolyl-, isoindolyl-, indolizinyl-, benzimidazolyl-, quinolyl-, isoquinolyl-, indazolyl-, benzotriazolyl-, tetrazolopyridyl-, tetrazolopyri-dazinyl-, dihydro-triazolopyridazinyl-group and the like; or means a 3-6 membered, more preferably 5-6 membered, 1-2 oxygen- and 1-3 N-containing unsaturated hetero-monocyclic group and might be oxazolyl-, isoxazolyl-, oxadiazolyl- (e.g. 1,2,4-oxadiazolyl- and others) group and the like; or means unsaturated, 1-2 oxygen- and 1-3 N-containing condensed heterocyclic group and might be benzoxazolyl-, benzoxadiazolyl-group and the like; or means a 3-8 membered, more preferably 5-6 membered, 1-2 sulfur- and 1-3 N-containing unsaturated hetero-monocyclic group and might be thiazolyl-, 1,2-thiazolyl-, thiazolinyl-, thiadiazolyl-group and the like; or means a 3-8 membered, more preferably 5-6 membered, one S-containing unsaturated hetero-monocyclic group and might be thienyl-group; or means one O-containing unsaturated heteromonocyclic group and might be furyl-group; or means unsaturated, 1-2 sulfur- and 1-3 N-containing condensed heterocyclic group and might be benzothiazolyl-, benzothiadiazolyl-group and the like.

A preferred "acyl" group when taken in itself or forming part of an acylated group, preferably means an acyl group which might be a short chain alkanoyl- (e.g. formyl-, acetyl-, propionyl, butyryl- and the like), a short chain alkoxy-carbonyl- (e.g. methoxy-carbonyl-, ethoxy-carbonyl-, propoxy-carbonyl-, butoxy-carbonyl-, tertbutoxy-carbonyl- and the like), a short chain alkyl-sulphonyl- (e.g. methyl-sulphonyl-, ethyl-sulphonyl- and the like), aryl-sulphonyl- (e.g. phenyl-sulphonyl- and the like), aroyl- (e.g. benzoyl, naphthoyl- and the like), aryl-(short chain alkanoyl)- (e.g. phenylacetyl-, phenyl-propionyl- and the like), cyclo-(short chain alkyl)-(short chain alkanoyl)- (e.g. cyclohexyl-acetyl and the like), aryl-(short chain alkoxy)-carbonyl- (e.g. benzyloxy-carbonyl and the like), aryl-carbamoyl- (e.g. phenyl-carbamoyl-, naphthyl carbamoyl- and the like), cycloalkyl-carbamoyl- (e.g. cyclohexyl-carbamoyl- and the like), hetero-monocyclic sulphonyl- (e.g. thienyl-sulphonyl-, furyl-sulphonyl- and the like) group; and the acyl group can be optionally substituted with 1-3 substituents as written above in the "optionally substituted" section.

A preferred T-amino-alkyl group means a short chain alkyl group containing substituted N-atom in the T-position of the alkyl chain and in which the alkyl chain is optionally substituted with one or more substituents, preferably with one or two halogen (e.g. chloro-, bromo-, fluoro-, iodo-), hydroxyl group or acylated hydroxyl group, where the acyl group has been defined earlier; more preferably with one or two short chain alkyl groups and the "alkyl" definition is the same as written above. The N atom in the T position of the alkyl chain can be substituted with one or two short chain alkyl substituents, preferably methyl-, ethyl-, tert-butyl- and the like; with cycloalkyl carbamoyl- (e.g. cyclohexyl-carbamoyl- and the like), more preferably the N-atom can be a part of a saturated heterocyclic group which contains 1-4 nitrogen atoms and might be aziridinyl-, azetidinyl-, oxaziranyl-, pyrrolidinyl-, imidazolidinyl-, pyrazolidinyl-, perhydro-tiazolyl-, perhydro-izoxazolyl-, piperidinyl-, piperazinyl-, perhydropyrimidinyl-, perhydro-pyridazinyl-, morpholinyl-, perhidro-1H-azepinyl-groups and the like; the N-atom in the T position can be substituted with an aryl group (e.g. phenyl and the like), and can be quaternarized by a short chain alkyl substituent or oxidized as well.

If desired, the free bases of the general formulae (I) and (II) may be transformed to acid addition salts by reacting with organic acids and may be acetate, maleate and the like; or by reacting with inorganic acids and may be hydrochloride, hydrobromide, hydroiodide, sulphate, phosphate and the like; or by reacting with amino acids and may be arginine-salt, glutamic acid salt and the like.

In a non-limiting embodiment of the hydroxylamine derivative of structure (I), Z is a covalent bond and X is a halogen, preferably chloro or bromo. Preferred compounds belonging to this group has a A (i) aralkyl or aralkyl having substituted aryl moiety, preferably phenyl alkyl or phenyl alkyl having one or more substituents, preferably alkoxy; (ii) aryl or substituted aryl, preferably phenyl or substituted phenyl, preferably substituted phenyl containing one or more of alkyl, halogen, haloalkyl, alkoxy or nitro group; (iii) naphthyl; (iv) an N-containing heteroaryl group, including those which may be condensed with a benzene ring, preferably piridyl; (v) an S-containing heteroaryl group or (vi) an O-containing heteroaryl group. Preferred compounds belonging to this group has as R (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moeity. Of the T-amino-alkyl group of (i) to (iv), particularly preferred are those with 3-8 carbon atom alkyl moiety.

Certain types of the hydroxylamine derivative of structure (I) having covalent bond as Z and halogen as X are disclosed in the U.S. Pat. Nos. 5,147,879, 5,328,906 and 5,296,606. These compounds can be prepared by procedures described in the cited US patents, preferably by diazotization of the corresponding $X=NH_2$ derivatives in the presence of the appropriate hydrohalide. The starting compounds can be obtained by known procedures described e.g. in Hungarian Patent No. 177,578 (1976), namely by coupling an amidoxime of structure 1 ($R^1=R^2=H$) with e.g. a reactive derivative of structure 2 in the presence of a base, and can be diazotized usually without isolation or purification. The terminal groups A and R of the compounds can be further amidified or derivatized, as desired.

In another non-limiting embodiment of the hydroxylamine derivative of structure (I), Z is covalent bond and X is a substituted hydroxy group OQ, wherein Q is an unsubstituted or substituted alkyl or aralkyl group. In a preferred embodiment, Q is a linear or branched alkyl. In these compounds, A is aryl or heteroaryl, preferably a N-containing heteroaromatic group; and R is preferably a (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl of (i) to (iv), particularly preferred are those with 3-8 carbon atom alkyl moiety.

A special group of the hydroxylamine derivatives of structure (I), wherein Z is covalent bond and X is OQ, is of structure (I'). Structure (I') contains a ring closed through the hydroxy group. These compounds represent a cyclic form of the compounds of structure (I), wherein R is a —$CH_2$—CH(OH)—R", R" being a liner or branched alkyl, or a substituted linear or branched alkyl, preferably T-amino-alkyl which is optionally substituted on its amino group and preferably contains $C_{1-5}$ straight or branched alkyl chain. Most preferably, R" is an T-amino-alkyl mono- or disubstituted on the amino group, wherein the amino-substituents, independently from each other may be one or two straight or branched alkyl or cycloalkyl, or the two amino-substituents, together with the adjacent N-atom form a 3 to 7, preferably 5 to 7-membered hetero ring, which optionally contains additional hetero atom. Of these, preferred compounds have A that is a phenyl, substituted phenyl, N-containing heteroaryl, substituted N-containing heteroaryl, S-containing heteroaryl, or substituted S-containing heteroaryl.

Hydroxylamine derivatives of structure (I) having covalent bond as Z and OQ as X have been disclosed in the Hungarian Patent Application No. 2385/1992. These compounds can be prepared from the corresponding halogen derivatives of the above group (hydroxylamine derivatives of structure (I), wherein Z is covalent bond and X is halogen) by procedures described in the Hung. Pat. Appln. No. 2385/1992, e.g., by reaction with alkoxides, or by alkaline ring closure for the cyclic compounds of structure (I').

In a non-limiting embodiment of the hydroxylamine derivative of structure (I), Z is covalent bond and X is $NR^1R^2$, wherein $R^1$ and $R^2$, independently from each other, are H, a linear or branched alkyl, a substituted linear or branched alkyl, cycloalkyl, or $R^1$ and $R^2$, together with the nitrogen atom attached thereto, form a saturated ring containing 3 to 7 members, preferably 5-7 membered saturated ring.

Of the compounds described in the immediately preceding paragraph, especially preferred are those wherein R is a (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety. Of these compounds, further preferred ones have A that is (i) aralkyl or aralkyl having substituted aryl moiety, preferably phenyl alkyl or phenyl alkyl having one or more substituents, preferably alkoxy; (ii) aryl or substituted aryl, preferably phenyl or substituted phenyl, preferably phenyl containing one or more of alkyl, halogen, haloalkyl, alkoxy, nitro, or acylamino group; (iii) naphthyl; (iv) an N-containing heteroaryl group, including those which may be condensed with a benzene ring, preferably piridyl; (v) an S-containing heteroaryl group or (vi) an O-containing heteroaryl group.

Hydroxylamine derivatives of structure (I) having covalent bond as Z and $NR^1R^2$ as X include both known and new derivatives. Compounds where X is $NH_2$ are disclosed in Hungarian Patent No. 177578 (1976) and can be synthesized by alkylation of unsubstituted amidoxime derivatives of structure 1 (structure 1, wherein $R^1$-$R^2$=H) with a reactive derivative of structure 2 in presence of a base.

A special group of the hydroxylamine derivatives of structure (I), wherein Z is covalent bond and X is $NR^1R^2$, is provided by structure (I"). Structure (I") represents a cyclic form of structure (I) which contains a ring closed through $NR^1R^2$ group. These compounds can be derived from compounds of structure (I), wherein $R^2$ is H and R is $CH_2$—CH (OH)—R", R" being a linear or branched alkyl or a substituted linear or branched alkyl.

Of the compounds of structure (I"), preferred are those wherein A is (i) aryl or substituted aryl, preferably phenyl or substituted phenyl, preferably substituted phenyl containing one or more of alkyl, halogen, haloalkyl, alkoxy, amino or nitro group; (ii) naphthyl; (iii) an N-containing heteroaryl group, including those which may be condensed with a benzene ring; (iv) S-containing heteroraryl group; and (v) O-containing heteroaryl group. Especially preferred of these compounds contain R" which is (i) T-amino-alkyl having mono or disubstituted amino moiety, or (ii) T-amino alkyl having mono or disubstituted amino moiety and also substituted alkyl moiety, preferably the alkyl moiety of T-amino-alkyl of (i) and (ii) contains 1-5 carbon atoms. Especially preferred are the T-amino-alkyl group having disubstituted amino moiety, wherein the substitutents, together with the nitrogen atom attached thereto, form a 3-7 member, preferably 5-7 member, saturated heterocyclic ring. The heterocyclic ring may contain additional heteroatom(s). In these T-amino-alkyl groups the amino-substituent is preferably a linear or branched alkyl group or cycloalkyl. In the compounds of the general formula (I") $R^1$ is hydrogen, unsubstituted or substituted straight or branched alkyl, cycloalkyl, unsubstituted aralkyl or aralkyl substituted in the aryl- and/or alkyl moiety.

The compounds of structure (I") can be prepared by the ring closure between atoms N(4)-C(5). The required open chain derivatives are compounds of structure (I) wherein Z is a covalent bond, X is $=NR^1R^2$, wherein $R^1$ is as defined in connection with the compounds of the formula (I") above, $R^2$ is H and R is a group of the formula —$CH_2$—$CHY^5$—R" wherein $Y^5$ represents a leaving group, e.g., a halogen atom. Such derivatives could be obtained from the corresponding $Y^5$=OH compounds with inorganic halogenating agents, e.g., thionyl chloride or phosphorus pentachloride. The halogenation can be carried out with or without an inert solvent e.g. benzene, chloroform, tetrahydrofurane etc., usually by boiling. After removing the excess of the reagent, e.g., by evaporation of the thionyl chloride, the crude halogen derivative is cyclized—either after or without isolation or purification—by treatment with a strong base, e.g., potassium butoxide in t-butanol to give compound I", which is finally isolated and purified by standard procedures (extraction, recrystallization, etc.).

In a non-limiting embodiment of the hydroxylamine derivative of structure (I), Z is oxygen and X is OQ, wherein Q is an alkyl, substituted alkyl, aralkyl, or aralkyl having substituted aryl or substituted alkyl moiety. The alkyl or substituted alkyl that is Q has preferably 1-4 carbon atoms. Of these compounds, preferred ones have A that is an alkyl or substituted alkyl, preferably 1-4 carbon atoms, or aralkyl or aralkyl having substituted aryl or substituted alkyl moiety. Of these compounds, preferred have R that is (i) T-amino-alkyl, (ii) T-amino-alkyl having mono or disubstituted amino moiety; (iii) T-amino alkyl having substituted alkyl moiety; (iv) T-amino amino alkyl having mono or disubstituted amino moiety and also substituted alkyl moiety, with a hydroxy or acyloxy group being preferred substituent group for the alkyl moiety.

These hydroxylamine derivatives of structure (I), wherein Z is oxygen and X is OQ, can be obtained in the reaction of O-substituted hydroxylamines having structure 6 (see e.g., Ger. Off. 2,651,083 (1976)) and orthoesters having structure 7. The condensation is usually carried out in the regent itself, as a solvent, preferably by boiling. After evaporation, the product is isolated by crystallization, occasionally, (if there is an amine function in the side chain R) in the form of acid addition salt.

In a non-limiting embodiment of the hydroxylamine derivative of structure (I), Z is oxygen and X is $NR^1R^2$, wherein $R^1$ and $R^2$, independently from each other, are H, a linear or branched alkyl, a substituted linear or branched alkyl, cycloalkyl, aryl, substituted aryl, or $R^1$ and $R^2$, together with the nitrogen atom attached thereto, form a saturated ring containing 3 to 7 members, preferably 5-7 membered saturated ring. Of these compounds especially preferred are those wherein R is a (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety. Of these compounds, it is preferred that A is (i) alkyl or substituted alkyl; (iii) aralkyl or aralkyl having substituted aryl and/or substituted alkyl moiety; or (iv) aryl or substituted aryl, preferably phenyl or substituted phenyl.

Preparation of the compounds can be prepared as described herebelow, wherein the methods depend on the nature of X, namely whether X is an unsubstantiated amino ($NH_2$) or a substituted amino functionality.

Preparation of the compounds where X is $NH_2$ can be accomplished by the addition of hydroxylamine of structure 6 to an organic cyanate of structure A-O—CN (see, e.g., Chem.

Ber. 98, 144 (1965)). The reaction is carried out preferably in an inert organic solvent, usually at room temperature. The isolation often requires chromatographic purification.

The compounds having X that is monosubstituted amino group (e.g., $NHR^1$) are prepared from known haloformimidates of structure 9 (see e.g. Houben-Weil, "Methoden der Organischen Chemie", Band E/4, p. 544 (1983) and a compound of structure 6, in the presence of an organic base (e.g., triethylamine) or an inorganic base, such as sodium carbonate in an inert solvent, as benzene, tetrahydrofurane, etc., followed by standard work-up and purification procedures.

Derivatives where X is a disubstituted amino group are prepared by the reaction of a secondary amine of structure 5 with a compound of structure I, where Z is oxygen and X is OQ (preparation of these derivatives is described above). These amination reactions are performed in polar organic solvents, e.g., ethanol, by refluxing, if necessary.

In another non-limiting embodiment of the hydroxylamine derivative of structure (I), Z is $=NR^3$, wherein $R^3$ is hydrogen, an alkyl, substituted alkyl, aryl, substituted aryl, aralkyl, or aralkyl having substituted aryl or substituted alkyl moiety; and X is $NR^1R^2$, wherein $R^1$ and $R^2$, independently from each other, are H, a linear or branched alkyl, a substituted linear or branched alkyl, aryl or substituted aryl, cycloalkyl, or $R^1$ and $R^2$, together with the nitrogen atom attached thereto, form a saturated ring containing 3 to 7 members, preferably 5-7 membered saturated ring.

Of these compounds, it is further preferred that A is an alkyl, substituted alkyl, aralkyl, aralkyl, aralkyl having substituted aryl or substituted alkyl moiety, aryl, or substituted aryl group. Preferred R for compounds belonging to this group of hydroxylamine derivative is (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. It is preferred that the alkyl moiety of T-amino-alkyl of (i) to (iv) contain 3-8 carbon atoms.

The hydroxylamine derivatives of structure (I), wherein Z is $NR^3$ and X is $NR^1R^2$, can be prepared by aminolysis of the corresponding isourea derivatives belonging to a group of compounds described above (this group corresponds to the hydroxylamine derivatives of structure (I) having Z is oxygen and X is $NR^1R^2$) with ammonia or a primary or secondary amine. The reaction is carried out preferably in a polar solvent, e.g., water or ethanol, using excess of the amine. Alternatively, haloformamides of structure 10 (Houben-Weil "Methoden der Organischen Chemie," Band E/4, page 553 (1983)) can be reacted with a compound having structure 6 in the presence of an organic or inorganic base to give compounds of this group as well. The reaction carried out in inert organic solvent, usually at ambient temperature.

The compounds wherein R is a group of the formula (b) wherein $R^7$ is acyl, are prepared by esterifying the corresponding compounds containing hydrogen as $R^7$. The alkyl- or aryl esters are usually obtained by using an acid chloride or anhydride in the presence of a tertiary amine or an inorganic base, preferably in an inert solvent.

Another group of hydroxylamine derivatives useful in the present invention have structure (II), which represents the tautomeric form of the compounds of structure (I). In a non-limiting embodiment of the hydroxylamine derivative of structure (II), Z is covalent bond and X is oxygen. Preferred compounds belonging to this group has A that is (i) alkyl, aralkyl or aralkyl having substituted aryl or alkyl moiety; (ii) aryl or substituted aryl, preferably phenyl or substituted phenyl having one or more substituents, preferred substituent groups including an alkyl, haloalkyl or alkoxy group; (iii) an N-containing heteroaryl group, preferably piridyl; or (iv) S-containing heteroaryl group. For compounds belonging to this group, preferred R is (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety. Preferred compounds of this group has R' that is hydrogen, an alkyl, substituted alkyl, aryl, substituted aryl, aralkyl, or aralkyl having substituted aryl or alkyl moiety.

Compounds belonging to this group are disclosed in the Hungarian Patent Application No. 2385/1992. The routes for their preparation are described therein, most preferably, they can be obtained by acylation of O-substituted hydroxylamine derivatives having structure 6 (see also, e.g., Ger. Off. 2,651, 083 (1976)) with an acid chloride having structure 11. This route can be employed also for the preparation of these new derivatives, where R' is other than hydrogen, using compound of structure 12—instead of structure 6—as starting material.

In another non-limiting embodiment of the hydroxylamine derivative of structure (II), Z is chemical bond; X is $=NR^4$, wherein $R^4$ is H, an alkyl, substituted alkyl, aryl, substituted aryl, aralkyl, aralkyl having substituted aryl or substituted alkyl group, cycloalkyl; and R' that is an alkyl, substituted alkyl, aryl, substituted aryl, aralkyl, or aralkyl having substituted aryl or substituted alkyl moiety. Among these compounds preferred are those wherein (A) is (i) aralkyl or aralkyl having substituted aryl moiety, preferably phenyl alkyl or phenyl alkyl having one or more substituents, preferably alkoxy; (ii) aryl or substituted aryl, preferably phenyl or substituted phenyl, preferably substituted phenyl containing one or more alkyl, haloalkyl or nitro group; (iii) naphthyl; (iv) an N-containing heteroaryl group, preferably piridyl; or (v) S-containing heteroaryl group. Preferred compounds belonging to this group as R (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety of the T-amino-alkyl group of (i) to (iv), particularly preferred are those with 3-8 carbon atom alkyl moiety.

These compounds can be prepared either by O-alkylation of a N, N'-disubstituted amidoxime of structure 13 with a chemical compound having structure 2 (for the reaction conditions, see preparation of compounds of structure I, wherein Z is covalent bond and X is $NR^1R^2$), or by O-acylating an N, O-disubstituted hydroxylamine of the formula 12 with an imidoyl halide of the formula 16, the reaction being carried out in an inert solvent, preferably in the presence of an organic or inorganic acid scavenger.

The compounds wherein R is a group of the formula (b) wherein $R^7$ is acyl, are prepared by esterifying the corresponding compounds containing hydrogen as $R^7$. The alkyl- or aryl esters are usually obtained by using an acid chloride or anhydride in the presence of a tertiary amine or an inorganic base, preferably in an inert solvent.

In another non-limiting embodiment of the hydroxylamine derivative of structure (II), Z is oxygen and X is oxygen. Preferred compounds belonging to this group has A that is an alkyl, substituted alkyl, aralkyl, or aralkyl with substituted aryl or alkyl moiety. R is preferred to be (i) T-amino-alkyl, (ii)

T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety. Preferred compounds of this group has R' that is hydrogen, an alkyl, substituted alkyl, aryl, substituted aryl, aralkyl, or aralkyl with substituted aryl or alkyl moiety.

Compounds belonging to this group are disclosed in Hung. Patent Application No. 1756/95 (filed Jun. 15, 1995). They are prepared by acylation of a hydroxylamine having structure 6 or structure 12 with a chloroformate having structure 14, in a similar manner as with the simple acid chlorides, as described for the synthesis of compounds of structure II wherein Z is covalent bond and X is oxygen. The reaction requires the presence of a base, inorganic or organic, and can be performed in an inert solvent, e.g., in chloroform. The side-product salt is removed, e.g., by extraction with water, and the product is isolated from the organic solution.

In yet another non-limiting embodiment of the hydroxylamine derivative of structure (II), Z is oxygen; X is $=NR^4$, wherein $R^4$ is alkyl, substituted alkyl, aralkyl, aralkyl having substituted aryl or substituted alkyl group, aryl, substituted aryl, heteroaryl or substituted heteroaryl group. In these compounds A is preferably alkyl, substituted alkyl, aryl, substituted aryl, most preferably unsubstituted or substituted phenyl, aralkyl or aralkyl with substituted aryl or alkyl moiety, and R is preferably T-aminoalkyl, which suitably contains a hydroxy or acyloxy group in the alkyl chain, and is optionally substituted on the amine nitrogen, wherein the alkyl chain of the said T-aminoalkyl group preferably contains 3 to 8 carbon atoms. In these compounds R' is preferably alkyl, aryl or aralkyl which groups may be unsubstituted or substituted.

These compounds are N-substituted analogues of hydroxylamine derivatives of structure (I), wherein Z is oxygen and X is $NR^1R^2$, and can be prepared, similarly from haloformimidates having structure 9 and a chemical compound having structure 12, in the presence of an organic base (e.g., triethylamine) or inorganic base. e.g. sodium carbonate in an inert solvent, as benzene, tetrahydrofurane etc., followed by standard work-up and purification procedures.

In another non-limiting embodiment of the hydroxylamine derivative of structure (II), Z is $=NR^3$, wherein $R^3$ is selected from the group consisting of hydrogen, an alkyl, substituted alkyl, aryl, substituted aryl, aralkyl, and aralkyl having substituted aryl or substituted alkyl moiety; and X is oxygen. Preferred compounds of this group have A that is (i) aralkyl or aralkyl having substituted alkyl or aryl moiety, preferably phenylalkyl or phenylalkyl having one or more substituents; (ii) aryl or substituted aryl, preferably phenyl or substituted phenyl, preferably substituted phenyl containing one or more of alkyl, alkoxy, halogen, haloalkyl or nitro group; (iii) an N-containing heteroaryl group; or (iv) an alkyl or substituted alkyl, linear or branched, preferably containing 4 to 12 carbon atoms, or (v) a cycloalkyl group. Preferred compounds belonging to this group has (i) T-amino-alkyl, (ii) T-amino-alkyl having mono or disubstituted amino-moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety. In these compounds R' is preferably hydrogen, an alkyl, substituted alkyl, aralkyl or aralkyl having substituted aryl or alkyl moiety, aryl, substituted aryl, acyl or substituted acyl group.

These compounds are disclosed in a co-pending Hungarian Patent Application No. 1756/95 and can be prepared by reaction of a hydroxylamine compound having structure 6 or structure 12 with an isocyanate having structure 15, in an inert solvent, usually by simple stirring of the mixture at room temperature for 2-24 hours. Finally, the products are isolated—after evaporation of the solvent—preferably by crystallization.

In a non-limiting embodiment of the hydroxylamine derivatives of structure (II), Z is $=NR^3$, wherein $R^3$ is selected from the group consisting of hydrogen, an alkyl, substituted alkyl, aryl, substituted aryl, aralkyl, and aralkyl having substituted aryl or substituted alkyl moiety; X is $=NR^4$, wherein $R^4$ is H, an alkyl, substituted alkyl, aryl, substituted aryl, aralkyl, aralkyl having substituted aryl or substituted alkyl group, cycloalkyl,; and R' is an alkyl, substituted alkyl, aralkyl, or aralkyl having substituted aryl or substituted alkyl moiety, or aryl or substituted aryl. Preferred compounds belonging to this group have as $R^3$ hydrogen, alkyl or substituted alkyl $R^4$ is hydrogen or an aryl group, A is alkyl, substituted alkyl, aryl or substituted aryl, or aralkyl, which may be substituted in the aryl and/or alkyl moiety. Of these compounds, preferred ones have R that is (i) T-amino-alkyl, (ii) T-amino-alkyl having mono or disubstituted amino moiety; (iii) T-amino alkyl having substituted alkyl moiety; (iv) T-amino alkyl having mono or disubstituted amino moiety and also substituted alkyl moiety, with a hydroxy or acyloxy group being preferred substituent group for the alkyl moiety. Of the T-amino-alkyl group of (i) to (iv), particularly preferred are those with 3-8 carbon atom alkyl moiety.

Preparation of compounds belonging to this group can be accomplished by aminolysis of the of the corresponding isourea derivatives (compounds having structure (II), wherein Z is oxygen and X is $NR^4$) with a primary or secondary amine or ammonia. The reaction is carried out preferably in a polar solvent, e.g., water or ethanol, using an excess of the amine. Alternatively, haloformamidines having structure 10 can react with a compound of structure 12 in the presence of an organic or inorganic base in inert solvents, usually at their boiling point.

One non-limiting embodiment of the hydroxylamine derivative of structure (I) defines a novel group of compounds, wherein X is halogen, preferably a chloro or bromo; Z is a chemical bond and A is a group of the formula (a) wherein $Y^1$ is halo, alkoxy, a nitro group or a haloalkyl group, preferably haloalkyl containing 1-4 carbon atoms; and n is 1, 2, or 3; or O-containing heteroaryl, preferably furyl, S-containing heteroaryl (preferably thienyl), or N-containing heteroaryl group (preferably piridyl, quinolyl, or isoquinolyl) which may be condensed with a benzene ring and R is a group having structure (b), wherein $R^5$ and $R^6$, independently from each other, are H, a linear or branched alkyl, preferably a substituted linear or branched alkyl, preferably $C_{1-4}$ alkyl, or cycloalkyl, or $R^5$ and $R^6$, when taken together with the nitrogen atom attached thereto, form a 3 to 7, preferably 5 to 7, membered saturated heterocyclic ring, $Y^6$ is $—OR^7$, wherein $R^7$ is H or an acyl group, preferably alkyl carbonyl, substituted alkyl carbonyl, aryl carbonyl or substituted aryl carbonyl, or aminoacyl or substituted aminoacyl; k is 1, 2 or 3; and m is 1, 2, or 3, with the proviso, that when A is piridyl or naphtyl, or a group of the formula (a) wherein $Y^1$ is halo or alkoxy, then $R^7$ is other than H. These compounds may optionally contain as A an N-containing heteroaromatic group with N-quaternary $C_{1-4}$ alkyl or the oxide of the said N-containing heteroaromatic group and/or an R wherein the ring formed by the terminal groups $R^6$ and $R^7$ is an N-quaternary or N-oxidized saturated heterocyclic ring. Preferred are among these compounds those wherein A is a group of the formula (a) wherein $Y^1$ is trifluoromethyl. This group of the hydroxylamine derivatives of the formula (I) also includes the optically active stereoisomers of the compounds wherein X is halo, A is piridyl, Z is a chemical bond, and R is the group of the formula (b) wherein $R^5$ and $R^6$ independently from each other are H, straight or branched alkyl, preferably $C_{1-4}$ alkyl or cycloalkyl, or $R^5$ and $R^6$, together with the adjacent N atom form a 3 to 7 membered, preferably 5 to 7 membered heterocyclic ring, $Y^6$ is $-OR^7$, wherein $R^7$ is aminoacyl, k is 1, 2 or 3 and m is 1, 2 or 3.

These novel compounds can be prepared using procedures that are analogous to those described in U.S. Pat. Nos. 5,147,879; 5,328,906; and 5,296,606. For example:

Derivatives where both $R^5$ and $R^6$ are other than hydrogen, are prepared by the diazotization of the corresponding $NH_2$ derivatives (the hydroxylamine derivatives of structure (I), wherein Z is covalent bond and X is $NH_2$) in the presence of the appropriate hydrogen halide, similarly to the procedure described in U.S. Pat. Nos. 5,147,879; 5,328,906; and 5,296,606. The starting compounds can be obtained also by a known procedure described, e.g., in Hungarian Patent No. 177578, namely by coupling an amidoxime having structure 1, wherein $R^1$ and $R^2$ of structure 1 is H, with e.g. a reactive derivative having structure 2 in the presence of a base, and can be diazotized usually without isolation or purification.

If in the desired structure $R^7$ is H and m is 1, the synthesis can be accomplished by the reaction of an oxyrane having structure 3 and amine having structure 4. This procedure also can be used for the synthesis of $R^5$=H derivatives.

Compounds where R is a group of the structure (b), and where $R^7$ in this group is an acyl group, are prepared by the esterification of the corresponding $R^7$=H derivatives. Alkyl or aryl esters are usually obtained with an acid chloride or anhydride in the presence of a tertiary amine or an inorganic base, preferably in an inert solvent, or in certain cases by the Schotten-Bauman procedure using aqueous inorganic base in a two-phase system. For the preparation of the aminoacyl esters, carboxyl-activated N-protected amino acid derivatives (e.g., active esters) are used as reagents in procedures basically known from the peptide chemistry. This coupling also requires the presence of a base (e.g. triethylamine). The isolation and purification of the products are performed by using standard preparative techniques; the final preparation is often in the form of a salt with appropriate inorganic or organic acids. Starting from chiral amino acids, the products are frequently diastereomers, possessing the second chiral center in the R group. During the isolation, these diastereomers often separate, and the product can be obtained in stereo-pure form.

Compounds having structure (I) wherein Z is chemical bond, X is halo, preferably chloro or bromo A is a group of the formula (c) and R is a group of the formula (d); one or both of $Y^2$ and $Y^3$, from which at least one must be present in the molecule, are oxygen, or an alkyl or substituted alkyl having 1-4 carbon atoms; k is 1, 2, or 3; and m is 1, 2, or 3. $Y^2$ and $Y^3$ are attached by the dotted line, which means the optional presence of these substituents, are also novel hydroxylamine derivatives. When the compound is a mono- or bivalent cation, the anion thereof is one or two halide, preferably iodide ion.

These hydroxylamine derivatives are prepared by the chemical modifications (i.e., N-oxidation or quaternerization) of the terminal pyridine and/or piperidine groups in their unsubstituted precursors. For the oxidation, preferably peracids, e.g. substituted perbenzoic acids are used in inert solvents (e.g., chloroform, dichloromethane). If both oxidizable groups are present in the molecule, mono- or dioxides may form depending on the quantity of the reagent used. At the end of the reaction, the excess reagent is decomposed and the product is isolated by evaporation. The quaternerization can be accomplished with alkyl halides (e.g., methyliodide), preferably by refluxing the reagent in a suitable solvent, e.g., acetone. The product is often insoluble in the medium, and can be isolated by simple filtration.

Yet another novel group of compounds belonging to the hydroxylamine derivatives having structure (I) are those wherein Z is a chemical bond. A is aralkyl, substituted aralkyl, preferably phenylalkyl which may have one or more alkoxy, preferably alkoxy having 1 to 4 carbon atom, phenyl, substituted phenyl having one or more substituents, preferred substituent groups including an alkyl, preferably alkyl or haloalkyl having 1 to 4 carbon atom, halo, acylamino or nitro group; or a N-containing heteroaryl group, which may be condensed with benzene ring, preferably pyrrolyl, pyridyl, isoquinolyl or quinolyl, or a sulfur containing heteroaromatic group, preferably thienyl, wherein the heteroaryl groups may be substituted with one or more alkyl, preferably alkyl having 1 to 4 carbon atoms; X is $-NR^1R^2$, wherein $R^1$ and $R^2$, independently from each other, are H, a linear or branched alkyl, a substituted linear or branched alkyl, preferably alkyl having 1 to 6 carbon atoms, a cycloalkyl or $R^1$ and $R^2$ taken together with the nitrogen atom attached thereto may form a 3 to 7, preferably 5 to 7, membered saturated hetero ring; R is a group of the formula (e), wherein $R^5$ and $R^6$, independently from each other, are H, a linear or branched alkyl, or a substituted linear or branched alkyl, preferably alkyl having 1 to 4 carbon atoms, or cycloalkyl, or $R^5$ and $R^6$ taken together with the nitrogen atom attached thereto form a 3-7, preferably 5-7 membered saturated hetero ring, which may contain additional hetero atoms and substituents, the substituents being preferably alkyl having 1 to 4 carbon atoms; $Y^4$ is H or an alkyl or substituted alkyl having 1-4 carbon atoms; $Y^5$ is H, or an alkyl or substituted alkyl having 1-4 carbon atoms, or $OR^7$ wherein $R^7$ is H or an acyl; k is 1, 2, or 3; and m is 1, 2, or 3, with the proviso that when A is phenyl which is unsubstituted or substituted with halogen or alkoxy; or phenylalkyl substituted with alkoxy; or a pyridyl group, and $R^7$ is H, then at least one of $R^1$ and $R^2$ is other than H, or when A is phenyl which is unsubstituted or substituted with halogen or alkoxy; phenylalkyl substituted with alkoxy; or pyridyl, and $R^1$ and $R^2$ are each H, then $R^7$ is other than H.

The compounds wherein X is an $NH_2$ derivative, are prepared—similarly to the above-mentioned procedure—by the reaction of the corresponding intermediates having structure 1, wherein $R^1$ and $R^2$ of structure 1 are H, with a compound having structure 2. The alkylating agent (having structure 2) may contain hydroxyl and/or amino substituents. The reaction requires the presence of an inorganic or organic base, in a preferable manner alcoholic alcoholate solution is used as medium and base. The products are often isolated in the form of salt with a suitable organic or inorganic acid.

Another group of the above novel compounds is characterized by $R^1$ and $R^2$, one or both of them being other than H in these derivatives. Such structures can be prepared in two ways:

(i) An amidoxime having structure 1, which already contains the required substituents $R^1$ and/or $R^2$, can react with a reactive compound of structure 2, similarly to the procedure described in the previous paragraph. The substituted amidoximes of structure 1, used as starting materials, are known from the literature [Chem. Rev. 62, 155-183 (1962)].

(ii) Substitution of the halogen atoms in the compounds having structure (1), wherein Z is covalent bond and X is halogen, by an amine of structure 5 can result in similar compounds as well. In the case of derivatives bearing an OH substituent in the R group ($Y^4$=OH), this hydroxyl group has to be protected before, and deprotected after the substitution reaction, otherwise formation of the cyclic derivatives of structure (I') is favored. For the protection, acetyl type protecting groups, e.g., tetrahydropyranyl group, have proven most satisfactory. The protection is carried out by the reaction of the unprotected compound with dihydropyrane, followed by the halogen/amine displacement, which usually requires refluxing in a solvent, e.g., in alcohol. The deprotection of the product, finally, can be accomplished b acidic treatment, e.g., by boiling the ethanolic solution in the presence of e.g. p-toluenesulphonic acid.

As mentioned, a group of the novel compounds also includes those wherein $Y^5$ is an acyloxy group. They can be prepared by acylation of the corresponding $Y^5$=OH derivatives, which are either known from the literature (e.g., Hung, Patent No. 177578) or described in the present invention. The reactions can be accomplished identically to what is described for the analogous halo derivatives, wherein $R^7$ is an acyl group (method (iii)).

The novel hydroxylamine derivatives of the formula (I) also include those wherein Z is oxygen or an =$NR^3$ group wherein $R^3$ is an unsubstituted or substituted alkyl group, X is —$NR^1R^2$. $R^1$ and $R^2$ independently from each other are hydrogen, unsubstituted or substituted straight or branched alkyl, unsubstituted or substituted aryl, preferably phenyl or unsubstituted or substituted aralkyl group or $R^1$ and $R^2$ when taken together with the nitrogen atom attached thereto, form a 3 to 7 membered, preferably 5 to 7 membered saturated heterocyclic ring which optionally contains one or more hetero atoms. In these compounds A is an unsubstituted or substituted alkyl or unsubstituted or substituted aryl, preferably phenyl or substituted phenyl group or an unsubstituted or substituted aralkyl group and R is a group of the formula (b) wherein $R^5$ and $R^6$, independently from each other are H, straight or branched alkyl, preferably $C_{1-4}$ alkyl, or cycloalkyl, or $R^5$ and $R^6$, together with the N-atom attached thereto, form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl or arylcarbonyl, k is 1, 2, or 3 and m is 1, 2 or 3.

The novel hydroxylamine derivatives, wherein Z is oxygen and X is —OR, wherein Q is an unsubstituted or substituted alkyl or unsubstituted or substituted aralkyl group, A is an unsubstituted or substituted alkoxy group or an unsubstituted or substituted aralkyl group and R is a group of the formula (b), wherein $R^5$ and $R^6$, independently from each other are H, straight or branched alkyl, preferably $C_{1-4}$ alkyl, or cycloalkyl, or $R^5$ and $R^6$, together with the N-atom attached thereto, form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl or arylcarbonyl, k is 1, 2 or 3 and m is 1, 2 or 3, fall also within the scope of compounds of formula (I).

$R^1$ and $R^6$, independently from each other, are H, straight or branched alkyl, preferably $C_{1-4}$ alkyl or cycloalkyl, or $R^5$ and $R^6$, when taken together with the N atom attached thereto form a 3 to 7-membered, preferably 5 to 7-membered heterocyclic ring, $Y^6$, is H or —$OR^7$, $R^7$ is H or acyl, preferably unsubstituted or substituted alkylcarbonyl or arylcarbonyl, k is 1, 2 or 3 and m is 1, 2 or 3.

Another group of the novel hydroxylamine derivatives of the formula (I) is represented by those wherein A is unsubstituted or substituted aryl, preferably phenyl or N-containing heteroaromatic group, preferably piridyl or S-containing heteroaromatic group, Z is a chemical bond. X is —OQ wherein Q is $C_{1-4}$ alkyl and R is a group of the formula (b), wherein $R^5$ and $R^6$, independently from each other are H, straight or branched alkyl preferably $C_{1-4}$ alkyl or cycloalkyl or $R^5$ and $R^6$, when taken together with the N atom attached thereto form a 3 to 7-membered, preferably 5 to 7-membered heterocyclic ring. $Y^6$ is H, k is 1, 2 or 3 and m is 1, 2 or 3.

These compounds are prepared by the reaction of the corresponding hydroxylamine derivatives of the formula (I) wherein X is halo and the corresponding alcoholates, preferably in an alcohol corresponding to the alcoholate, preferably by refluxing. The reaction mixture is treated with methods known in the art and the product is isolated by chromatography or salt-forming.

The novel hydroxylamine derivatives of the formula (II) also include the group of compounds wherein X is oxygen, A is $C_{1-20}$ straight or branched alkyl, unsubstituted or substituted aryl, preferably phenyl or halophenyl, unsubstituted or substituted aralkyl, naphtyl or N-containing heteroaromatic group, preferably piridyl, Z is a chemical bond. R' is H, $C_{1-4}$ alkyl or aralkyl, preferably phenylalkyl, R is a group of the formula (b), wherein $R^5$ and $R^6$, independently from each other, are H, straight or branched alkyl, preferably $C_{1-4}$, alkyl or cycloalkyl, or $R^5$ and $R^6$, when taken together with the N atom attached thereto form a 3 to 7-membered, preferably 5 to 7-membered heterocyclic ring, $Y^6$ is H or —$OR^7$, $R^7$ is H, k is 1, 2 or 3 and m is 1, 2 or 3, with the proviso, that when A is other than alkyl and R' is H, $Y^6$ is H.

The novel compounds wherein Z is a covalent bond, oxygen or an =$NR^3$ group wherein $R^3$ is hydrogen or an unsubstituted or substituted alkyl group, X is =$NR^4$, wherein $R^4$ is hydrogen, an unsubstituted or substituted alkyl or unsubstituted or substituted aryl, preferably phenyl group, or substituted or unsubstituted aralkyl, preferably phenylalkyl, fall also within the scope of compounds or formula (II). In these compounds A is an unsubstituted or substituted alkyl or an unsubstituted or substituted aryl preferably phenyl or substituted phenyl, or unsubstituted or substituted aralkyl, preferably phenylalkyl, or cycloalkyl, R' is an unsubstituted or substituted alkyl or unsubstituted or substituted aryl, preferably phenyl, or unsubstituted or substituted aralkyl, preferably phenylalkyl, R is a group of the formula (b), wherein $R^5$ and $R^6$, independently from each other, are H, straight or branched alkyl, preferably $C_{1-4}$ alkyl or cycloalkyl, or $R^5$ and $R^6$, when taken together with the N atom attached thereto form a 3 to 7-membered, preferably 5 to 7-membered heterocyclic ring, $Y^6$ is H or —$OR^7$, $R^7$ is H or acyl, preferably unsubstituted or substituted alkylcarbonyl or arylcarbonyl, k is 1, 2 or 3 and m is 1, 2 or 3.

Novel hydroxylamine derivatives are also those of the formula (II) wherein X is oxygen, A is unsubstituted or substituted alkyl, unsubstituted or substituted aralkyl, preferably phenylalkyl, Z is oxygen, R' is alkyl or aralkyl, preferably phenylalkyl, R is a group of the formula (b), wherein $R^5$ and $R^6$, independently from each other, are H, straight or branched alkyl, preferably $C_{1-4}$ alkyl or cycloalkyl, or $R^5$ and $R^6$, when taken together with the N atom attached thereto form a 3 to 7-membered, preferably 5 to 7-membered heterocyclic ring, $Y^6$ is H or —$OR^7$, $R^7$ is H or acyl, preferably unsubstituted or substituted alkylcarbonyl or arylcarbonyl, k is 1, 2 or 3 and m is 1, 2 or 3.

The hydroxylamine compounds of the formula (II), wherein X is oxygen and Z is =NH, are also novel compounds.

One group of these compounds is formed by those wherein A is unsubstituted or substituted alkyl, cycloalkyl, unsubstituted or substituted aralkyl, preferably phenylalkyl, unsubstituted phenyl or phenyl substituted with halo, alkyl, haloalkyl, alkoxy or nitro, R is a group of the formula (b), wherein $R^5$ and $R^6$, independently from each other, are H, straight or branched alkyl, preferably $C_{1-4}$, alkyl or cycloalkyl, or $R^5$ and $R^6$, when taken together with the N atom attached thereto form a 3 to 7-membered, preferably 5 to 7-membered heterocyclic ring, $Y^6$ is H or —OH, k is 1, 2 or 3 and m is 1, 2 or 3.

Another group of these compounds is formed by those wherein A is a group of the formula (a), wherein $Y^1$ is haloalkyl, preferably trifluoromethyl and n is 1, 2 or 3, R' is H and R is a group of the formula (b), wherein $R^5$ and $R^6$, independently from each other, are H, straight or branched alkyl, preferably $C_{1-4}$ alkyl or cycloalkyl, or $R^5$ and $R^6$, when taken together with the N atom attached thereto form a 3 to 7-membered, preferably 5 to 7-membered heterocyclic ring, $Y^6$ is H or —OH, k is 1, 2 or 3 and m is 1, 2 or 3.

The novel hydroxylamine derivatives according to the invention also include the cyclic compounds of the formula (I"), wherein A is unsubstituted phenyl or phenyl substituted with halo or nitro, or N-containing heteroaryl, $R^1$ is H and R" is an T-amino-alkyl group mono- or disubstituted on the amino group, the alkyl chain of which having 1 to 5 carbon atoms and the amino substituents, independently from each other, may be one or two straight or branched alkyl or cycloalkyl, or the two amino-substituents, together with the N atom adjacent thereto, form a 3 to 7-membered, preferably 5 to 7-membered saturated heterocyclic ring, or a $C_{1-4}$ alkyl N-quaternary derivative thereof, with the proviso, that when A is 3-piridyl, R" is different from 1-piperidinylmethyl.

Method of Increasing Molecular Chaperon Expression in Cells

The present invention relates to a method of enhancing expression of a molecular chaperons in cells, by treating cells and tissues with an effective amount of a hydroxylamine derivative. Hydroxylamine derivatives, the tautomeric forms of which are represented by formulae (I) or (II), can be used for this method. Structures of the formulae (I) and (II) are discussed in details in the preceding section entitled "Hydroxylamine Derivatives of the Invention".

In one non-limiting embodiment of the invention, a method of increasing molecular chaperon expression in cells exposed to stress is provided. In this method, the cells exposed to a physiological stress which induces expression of molecular chaperons by the cells are treated with an effective amount of hydroxylamine derivatives, the tautomeric forms of which are represented by formulae (I) and (II), after occurrence of the stress. The hydroxylamine derivatives increase the expression of molecular chaperons in these cells beyond the amount induced by the physiological stress.

In another non-limiting embodiment of the invention, the cells are treated with the hydroxylamine derivatives before they are exposed to a physiological stress. The hydroxylamine derivatives increase the molecular chaperon expression beyond the amount induced by the physiological stress.

The term "molecular chaperon," as used herein, refers to protein which assists other proteins to fold into correct or active conformations, usually by non-covalently binding to the proteins. Chaperons not only assist in the correction and restoration of proteins newly synthesized but also of those that have been denatured or misfolded. Molecular chaperons include, among others, heat shock proteins (hsp) from which hsp70 and hsp72 are of especial importance in connection with the invention, as well as the IgG heavy chain binding protein (BiP), and glucose regulated proteins (grp). Examples of hsp and grp include, but are not limited to, those belonging to the following classes: hsp70, hsp60, hsp90, grp94, grp80, and hsp27.

Preferably, eukaryotic cells which are treated with the hydroxylamine derivatives are mammalian cells, more preferably human cells. The term "eukaryotic cell" refers to both eukaryotic cells that are in vitro (cells that are outside a living organism, e.g. in culture condition) and in vivo (cells that are within a living organism, e.g., cells comprising tissues and organs).

From the eucaryotic cells of a living organism, neurons, muscle cells, vessel wall cells, especially endothelial cells, epithelial cells and cells of the immune system can preferably be treated in accordance with the method of the invention. Plant cells, including cells of living plant organisms can also preferably be treated in accordance with the method of the invention.

Under the term "physiological stress," as used herein, conditions or factors affecting the cell which would induce the "stress response" of the cell, e.g., induction of chaperon protein synthesis should be understood. Physiological stresses include factors that cause injury to cells or those disturbing homeostatic balance of cells. These are, for example, the metabolic, oxidative, local mechanical stresses or stresses caused by hypoxia, ischemia, heat shock, radiation or toxic materials. An important form of metabolic stress is caused by diabetes mellitus.

Another important appearance form of physiological stresses includes those leading to the formation of free radicals or increase of the quantity of cytokines in the environment of cells. Injuries in cells that are associated with various pathological conditions provide examples of physiological stresses.

In one non-limiting embodiment of the invention, the physiological stress that induces cells to express molecular chaperon as a response to physiological stresses leading to cardiovascular, vascular, cerebral, allergic, immune, autoimmune diseases, viral and bacterial infections, skin and mucosal diseases or diseases of renal tubuli of epithelial origin or causing conditions to be treated by cosmetical interventions.

Such cardiovascular diseases include most preferably atherosclerosis provoked by physiological stress, coronarial diseases, or cardiovascular diseases caused by hypertonia or pulmonary hypertonia.

Characteristic cerebral diseases are, among others, those caused by the cerebrovascular ischemia provoked by physiological stress, stroke, traumatic head injury, senile neurodegenerative diseases, especially senile dementia, AIDS dementia, alcohol dementia, Alzheimer's disease, Parkinson disease or epilepsy.

Characteristic diseases provoked by skin and mucosal diseases are the dermatological diseases or ulcerous diseases of the gastrointestinal system.

During the above diseases, the physiological stress induces chaperon expression in the cells, however, this effect is not sufficient enough to protect against cell damages caused by the diseases. The treatment with the above hydroxylamine derivatives which is associated with enhancement of chaperon expression or increase of chaperon activity makes possible the elimination of structural deviations caused by the disease and thus, regeneration of cells.

In one non-limiting example of the invention, the physiological stress is heat shock or exposure of cells to unusually high temperature. In another non-limiting example of the invention, the physiological stress is cellular injury associated with ischemia. Ischemic lesion of cells, especially heart muscle and cerebral cells is caused by cardiovascular disorders caused by vascular occlusion or rapture, such as coronary or cerebral thrombosis or vascular occlusion, stroke, embolism, or chronic vascular spasm. Ischemia induces "stress response" in cells, resulting in increased amount of hsp, which in turn protect the cells against deleterious effects of ischemia. (Mestril, R. et al, *J. Mol. Cell. Cardiol*, 27:45 (1995).

By treating these cells with an effective amount of hydroxylamine derivatives to those cells, molecular chaperon expression in the cells can be increased beyond the amount induced by ischemic condition as well as the activity of molecular chaperons can be enhanced.

In connection with this matter, when an organ is taken out of an animal for transplantation, such removal is a physiological stress causing injury to the cells comprising that organ, inducing chaperon expression. In such a case, administration of the hydroxylamine derivatives before or after the organ removal could increase the amount of chaperon produced by the cells of the organ or the activity thereof thus providing cytoprotective effect.

Neuronal injuries, besides ischemia, can be induced by many other stresses as well, which induce molecular chaperon production in the neuronal cells. In addition, excitotoxic neuronal injuries also induce production of molecular chaperons by neuronal cells and are included within the term "physiological stress."

In yet another example of the invention, physiological stress is provided by the toxic mediators of inflammation, such as oxidative radicals and cytokines, such as TNF, which are produced by macrophages. Cells exposed to increased amount of these toxic mediators are shown to express an increased amount of hsp, which in turn provide protection to these cells against the toxicity. (Kantengwa, S. et al, *Semin. Immun*. 3: 49-56 (1991). Various inflammatory diseases including pulmonary inflammatory conditions, such as adult distress syndrome, induce expression of hsp by the cells, which in turn exert cytoprotective effect. (Jacquier-Salin, M. R. et al., *Experientia* 50: 1031-1038 (1994)). When the amount of molecular chaperons in cells is increased beyond that induced by TNF and reactive oxygen species, the cells can be better protected against these cytotoxic factors and better enable to repair the damages caused by these.

Factors affecting the physiological state of cell membranes, including cell membrane fluidity, also provide examples of physiological stress. Increase of molecular chaperon expression in these cells beyond that induced by disturbance of the physiological state of cell membranes can provide better protection and also allow the cells to repair the cell membranes.

The phrase "an effective amount of the hydroxylamine derivatives," as used herein in connection with enhancing molecular chaperon production in cells under physiological stress, or cells which will be subsequently exposed to physiological stress, refers to an amount which will increase the expression of molecular chaperon beyond the level induced by the physiological stress alone. Such amount can be readily determined by one skilled in the art. Preferably, for cells in vitro, the effective amount is between $10^{-6}$-$10^{-3}$ M. More preferably, the effective amount is between $10^{-6}$-$5\times10^{-4}$ M.

When administering to an animal, the effective amount varies depending on various factors, such as a mode of administration, but determining effective range is within the skill of one skilled in the art and will not require undue experimentation. For example, when the hydroxylamine derivative is administered intravenously, the effective amount is preferably between 0.1-10 mg/kgbw, more preferably 0.5-2.0 mg/kgbw; and when administered orally, the effective amount is preferably between 10-500 mg/kgbw, more preferably between 50-100 mg/kgbw.

An increase in the molecular chaperon expression in cells can be detected using well established laboratory procedures such as Northern or Western blotting procedure.

An example of the Western blotting technique that can be used is set forth herein: Cells are cultured in vitro at 37° C. in Dulbecco's modified Eagle's medium (DMEM) supplemented with 10% fetal calf serum (GIBCO) in 5% $CO_2$. Hydroxylamine derivatives the tautomeric forms of which are represented by formulae (I) and (II) can be added to the cell culture, for example, $10^{-5}$ M of the compound is administered to cells 16 hours before the physiological stress, or after the time period following the physiological stress. However, the concentration of the hydroxy-lamine derivative, as well as the time of the administration of that compound, can be varied as desired by the experimental design.

Six hours after the heat shock, cells are washed two times in phosphate-buffered saline solution (PBS) then scrapped from the surface of the culture dishes in PBS. Then cells are spun for 5 min. at 1500 rpm and taken up in 100 µl modified solubilizing buffer (*Molecular Cloning, A Laboratory Manual*, Ed. Sambrook, Fritsche, Maniatis, Bold Spring Harbor Laboratory Press (1989)) containing 50 mM Tris-HCl, pH8.0; 5 mM EDTA; 150 mM NaCl; 15 Tritox N-100; 1 PMSF; 2 :g/ml aprotinin; 1 µg/ml chymostatin; 1 µg/ml pepstatin; and sonicated for 3×2o sec (2 min. intervals, setting 8).

Protein concentration is then determined from 5 µl samples by the Bradford assay (M. M. Bradford, *Anal. Biochem*., 72: 248-254 (1976)) in three parallel. Samples are adjusted to 100 µg/30 µl protein concentration with the above buffer and the next buffer so that the final concentration of the components in the buffer in the sample will be: 110 mM Tris-HCl pH 6.8, 8.3 mM mercaptoethanol, 3% SDS, 3% glycerol and some bromophenol blue and shaken at room temperature for 30 min. The sample thus obtained can then be used for to run a gel-electrophoresis.

When chaperon enhancing effect of the hydroxylamine derivatives of the invention is examined for cells in vivo, a physiological stress is applied to an animal, e.g., ischemia or STZ-induced diabetes. In case of ischemia, myocardial ischemia can be induced in an animal as described in Example 8; and diabetic condition can be induced as described in Example 10. A hydroxy-lamine derivative of the present invention can be administered to the animal before it is exposed to physiological stress, during the stress or afterwards. As stated previously, the timing of the administration can be varied according to an experimental design.

The following steps of protein preparation from relevant tissues obtained from the animals thus treated are carried out at 0-4 C. Tissues, such as liver tissues (about 15-20 g) are homogenized with a domestic mixer for 2 min. in 80 ml lysis buffer solution containing 50 mM Tris-HCl pH 8.0, 5 mM EDTA, 150 mM NaCl, 0.1% SDS, 1% Triton X-100 and 1-1 mM protease inhibitors (PMSF, benzamidine, amino-caproic-acid). The homogenate is then centrifuged at 20000×g for 30 min. in a Sorvall RC 28S centrifuge.

Protein concentration of the preparation is determined by the Bradford assay and adjusted to 5 mg/ml. The samples containing 1.8 mg protein are solubilized before gel-electrophoresis with 0.6 ml buffer containing 110 mM Tris-HCl pH 6.8, 8.3 mM mercaptoethanol, 3% SDS, 3% glycerol and some bromophenol blue and shaken at room temperature for 30 min.

The protein samples obtained from cell cultures or from animal tissues, both of which are described above, are used for electrophoresis and subsequent immunoblotting (both procedures are well known in the art and described in detail in *Molecular Cloning, A Laboratory Manual*, Ed. Sambrook, Fritsche, Maniatis, Cold Spring Harbor Laboratory Press (1989); *Protein Blotting Protocols for the Immobilon-P Transfer Membrane*, 3. Laboratory Manual, Millipore; and U. K. Laemmli, Nature: 227: 680-685 (1970).

For example, electrophoresis can be carried out according to Laemmli (U. K. Laemmli, *Nature*, 227:680-685 (1970)) on 8-18% polyacrylamide gel at constant voltage 50 V for overnight. Proteins are either stained with Coomassie Brilliant Blue R-250 or transferred to Immobilone PVDF (Millipore) at constant current (300 mA) for 3 hours at 4° C. in transfer buffer (10 mM CAPS, pH 11, 10% methanol) (*Protein Blotting Protocols for the Immobilon-P Transfer Membrane*, 3. Laboratory Manual, Millipore). After transfer, non-specific sites of the membrane are blocked with 2% bovine serum albumin (BSA) in TPBS (phosphate buffered saline with 0.1% Tween 20) for overnight at 4° C. The blot can then be incubated with an antibody directed as a molecular chaperon, e.g. GRP94 monoclonal antibody (SPA-850, StressGen) diluted 1:3000, with HSP60 monoclonal antibody (SPA-600, StressGen) with 1:2700 dilution, with HSP72 monoclonal antibody (C92F34-5, StressGen) diluted 1:1250 or with HSP90 monoclonal antibody (AC88, StressGen) diluted 1:2000, for 1 hour at room temperature. Then the membrane is washed with TPBS buffer for one hour, and incubated with horseradish peroxidase conjugated anti-rat (Sigma, 1:4000 dilution, for grp-94) or anti-mouse (Sigma, adsorbed with human and rat serum proteins, 1:3000 dilution, for Hsp60, HSP72 or HSP90) secondary antibody for additional 1 hour respectively. After successive washing with TPBS the membrane is developed with ECL (enhanced chemiluminescence) system (Amersham).

The changes in the stress protein content can be quantified using a BioRad densitometer (Model 1650) and a Hewlett-Packard Integrator (HP 3394A). Dilution series are prepared from protein solution containing known amount of chaperon, the above process is repeated with the dilutions and the chaperon concentration of the test samples are determined from the calibration curve obtained from the dilution tests.

Northern hybridization is another experimental procedure available for determining the level of molecular chaperon enhancement (by measuring the mRNA level) by the hydroxylamine derivatives of the invention. The cells or tissues can be obtained as described in connection with the Western blotting procedure. Total RNA from those cells and tissues can be extracted using RNAgents (Promega) according to the manufacturer's instructions (Protocols and Applications Guide, 2nd edition, 1991, Promega Corporation). The frozen tissue samples (about 50 to 100 mg each) are homogenized in 1.0 denaturing 4M guanidine-thiocyanate; 42 mM sodium citrate: 0.83 m β-mercaptoethanol; 0.1% Nonidet P-40) at 4° C. (Brinkman-homogenization). Then 1/10 vol. 3M sodium acetate (pH 4.0) is added and the homogenate are extracted with acidic phenol (phenol:chloroform:isoamylalcohol 25:24:1) for 10 seconds by vortex. The sample is incubated on ice for 15 minutes, and then centrifuged (4 C; 20 min., 10,000×g). The aqueous phase is then transferred to a new Eppendorf-tube the process is repeated and the aqueous phase is precipitated at −20° C. overnight with equal volume of isopropanol. Following centrifugation (4 C; 20 min. 10,000×g) the precipitate is washed twice with 95% ethanol and dried at room temperature. The RNA is suspended in 20 μl diethyl-pyrocarbonate (DEPC)-treated water and the concentrate is measured at 260-280 nm by spectrophotometry. Eight μg of total RNA is run on formaldehydeagarose gel by capillary transfer, the RNA on the gel is blotted onto nylon membrane according to the manufacture's instructions (Zeta-Probe GT, BioRad).

In individual samples, the molecular chaperon mRNA content is compared with the mRNA level of the glyceraldehyde-3-phosphate dehydrogenase (GAPDH) gene in the samples. cDNA probes (for example, full length human hsp70 cDNA when the mRNA probed is hsp70, and Apa-NcoI fragment of the rat GAPDH cDNA) are labeled with alpha-$^{32}$P CTP using Random Prime DNA Labeling Kit (USB). Radiolabeled DNA fragments are purified on Sephadex G-50 (Pharmacia) column as described (Ausubel et al. (eds)): Current Protocols in Molecular Biology: JOHN WILEY & SONS: 1987).

Prehybridizations are carried out at 65° C. in H-buffer (0.25M $Na_2HPO_4$, pH 7.2, 7% SDS) for 15 minutes. Hybridizations are carried out overnight (65 C; H-buffer) with isotope labeled cDNA probe concentration of at least $10^6$ cpm/ml. The membrane is then washed with 20 mM $Na_2HPO_4$, pH 7.2, 5% SDS (65 C; 2×15 min.) and evaluated by autoradiography. The same membrane is used for probing the hsp70 mRNA and the GAPDH and mRNA measurement used as internal standard.

The present invention further includes a method of treating or preventing various pathological conditions, i.e. diseases associated with the functioning of chaperon system and damages in the membranes of cells and cell-organelli by administering an effective amount of hydroxylamine derivatives, the tautomeric forms of which are represented by structures (I) and (II) to control pathological conditions in the organism. In the pathological conditions, characteristic molecular chaperon expression is induced in the cells. Increased molecular chaperon expression in those cells can assist them in repairing the damages caused by the pathological conditions and also in restoring the cellular homeostatic balance.

Such pathological conditions include ischemia, tumorous diseases, infections caused by pathogenic microorganisms, autoimmune diseases and dermatosis.

As used herein, "treating" refers to an amelioration in the clinical condition of the subject, and does not necessarily indicate that a complete cure is achieved. An amelioration refers to a decreased duration of illness or severity of illness, or subjective improvement in the quality of life of the subject or a prolonged survival of the patient.

An effective amount of hydroxylamine of the invention for treatment refers to an amount sufficient to result in the amelioration of clinical condition as described above. An effective amount depends on factors such as the route of administration and can easily be determined by one skilled in the art. The hydroxylamine derivatives of the present invention can be administered parenterally or orally, preferably orally or topically, and the effective amount is 10-500 mg/kgbw. More preferably, the effective amount is 20-100 mg/kgbw.

By using the method of treatment according to the present invention, the myocardium, brain tissues and kidney can be protected against tissue damage or necrosis caused by ischemia, wherein the method comprises administering to a subject an effective amount of hydroxylamine derivatives of the invention to decrease, prevent, or reverse the deleterious effect of prolonged ischemia.

The present invention includes use of a hydroxylamine derivatives, the tautomeric forms of which are represented by formulae (I) and (II) to manufacture a medicament for the treatment of pathological conditions described herein.

In a method for measuring the protective effect of the hydroxylamine derivatives animal test is used as set forth herein. Rats are anaesthetized with sodium-pentobarbital (Nembutal 60 mg/kg body weight, i.p.) and artificially ventilated with room air (2 ml/100 g; 54 stroke/minutes) via tracheotomy. The right carotid artery is then catheterized and connected to a pressure transducer (BPR-01, Stoelting) for the measurement of systemic arterial blood pressure (BP) by means of a preamplifier (Hg-02, Experimetria). Hydroxylamine derivatives of the invention are administered via cannule to jugular vein (i.v.) or orally (p.o.). Heart rate (HR) is measured by a cardiotachometer (HR-10, Experimetria); and the electrocardiogram (ECG standard lead II) is recorded on a devices recorder (MR-12, Medicor) by means of subcutaneous steel needle electrodes. The chest is opened by a left thoracotomy and the heart is then exteriorized by a gentle pressure on the right side of the rib cage. A compression was applied under the main left coronary artery as described by Selye et al. (1960). The heart is carefully replaced in the chest and the animal left to recover. Rectal temperature is monitored and kept constant at 37 C. The experimental protocol is initiated with a 15 minute stabilization period. If sustained blood pressure less than 70 mmHg or arrhythmia were observed during this period the animal was excluded from further experimentation. Myocardial ischemia is then induced with coronary occlusion for 5 minutes and reperfusion is allowed for 10 minutes.

During the entire experiment, blood pressure (BP), heart frequency (HR) and EKG are continuously registered on a multiscriptor (R61-6 CH, Medicor*). Hydroxylamine derivatives are administered at 5 to 60 minutes before the occlusion by i.v. or p.o. treatment. The doses of the hydroxylamine derivative can be 0.5; 0.75; 1.0 mg/kg i.v. and 100 mg/kg of body weight p.o., while the reference substance Bepridil is given in a dose of 1.0 mg/kg i.v. The mean duration of ventricular tachycardia (VT) and/or ventricular fibrillation (VF) during the first 3 minutes of reperfusion is measured and analyzed.

The present invention also includes a method of maintaining a cell membrane fluidity, when the cell membrane fluidity is affected as a result of a physiological stress. The method comprises the treatment of a cell or cell-organellum having altered membrane fluidity with an effective amount of hydroxylamine derivatives to restore the fluidity of said membrane. The experimental protocol set forth in connection with Example 9 (Steady State DPH fluorescence anisotropy) can be used for determining the effect of a hydroxylamine derivative of the invention on the cell membrane fluidity.

As mentioned, the present invention includes a method of treating pathological conditions associated with cell membrane or cell-organellum membrane. One example of such pathological condition is provided by diabetes mellitus as well as the diseases associated with mitocondrium damage, such as ALS (amyotrophic lateral sclerosis), Alzheimer disease, Parkinson disease, Huntington disease (HD), certain cardiomyopathies, such as those of toxic origin, caused by alcohol or heavy metals, inflammatory or viral cardiomyopathy or autoimmune cardiomyopathy. Hydroxylamine derivatives, the tautomeric forms of which are represented by structures (I) and (II), can be used in this method.

The method of the present invention can be used in the treatment of tumorous diseases, the method comprising administering an effective amount of hydroxylamine derivatives to the tumorous organism to prevent formation or growth of tumors. Hydroxylamine derivatives, the tautomeric forms of which are represented by structures (I) and (II), can be used in this method.

Pharmaceutical and Cosmetical Compositions
Containing the Hydroxylamine Derivatives As already mentioned, the invention also relates to the use of hydroxylamine derivatives of the general formulae (I) and (II), including the optically active strereoisomers thereof, in the preparation of pharmaceutical compositions (and optionally cosmetical compositions) useful in the treatment of cardiovascular, vascular, allergic, immune, autoimmune diseases, diseases caused by viral or bacterial infection, tumorous, skin and mucous diseases and renal tubule diseases provoked by physiological stress as well as those conditions caused also by physiological stresses which can be treated by cosmetical intervention, wherein formulae (I) and (II), or its salts, including the optically active stereoisomers thereof, A is an alkyl, substituted alkyl, aralkyl, aralkyl substituted in the aryl and/or in the alkyl moiety, aryl, substituted aryl, heteroaryl or substituted heteroaryl group, Z is a covalent bond, oxygen or $=NR^3$ wherein $R^3$ is selected from the group consisting of hydrogen, an alkyl, substituted alkyl, aryl, substituted aryl, aralkyl, or aralkyl substituted in the aryl and/or in the alkyl moiety, R is an alkyl or substituted alkyl, X in the tautomer of formula (I) is halogen or a substituted hydroxy or amino, monosubstituted amino or disubstituted amino group and X in the tautomer of formula (II) is oxygen, imino or substituted imino group and R' is hydrogen, an alkyl, substituted alkyl, aryl, substituted aryl, aralkyl, aralkyl having substituted aryl and/or alkyl moiety, acyl or substituted acyl group, and the compounds of formula (I) optionally contain intramolecular ring structures formed by coupling X and a reactive substituent.

By using these compounds, compositions for both preventive and curative purposes can be prepared, which, when administering in or applying on human or animal organism can be useful in preventing or controlling the cell damages cause by the above diseases thus relieving or eliminating the pathologic condition of the organism.

These compositions can be prepared by methods known per se in the preparation of cosmetics and pharmaceutical compositions, by mixing the active material and the corresponding carriers and/or auxiliaries. The compositions generally contain 0.5 to 99.5% by weight active compound. The amount of active material in the composition is determined by the nature and seriousness of disease, the age of patient and the mode of treatment. The hydroxylamine derivatives of the formula (I) and (II) can be formulated to compositions to be used orally and parenterally as well as topically.

The daily doses of the active compound is about 10 to 500 m/kg, preferably 20 to 100 mg/kg, which, especially in case of oral compositions, is distributed to 2-3 administration.

For purposes of oral administration, the compositions are formulated into dragée, granulate, if desired, solution or suspension. Parenteral compositions include aqueous suspensions and sterile injectable solutions, while rectal administration forms are, among others, suppositories, and topical forms include ointments, creams, emulsions and gels.

For preparing tablets, the active ingredient is mixed with suitable carriers, such as starch gelatin, lactose, magnesium stearate, talc, gumiarabicum and silicagel, the mixture is granulated and pressed into tablets.

In the preparation of dragées, a mixture similar to the above is prepared from the active ingredient and auxiliaries, the mixture is granulated, the granulate is pressed into a core, which is then coated with sugar, e.g. by using a sugar-containing aqueous polyvinylpirrolidon solution.

For preparing capsule forms, the active ingredient is mixed with auxiliaries, such as starch, talc, silica, microcrystalline cellulose, and the mixture is filled into hard or soft gelatin capsules.

These oral compositions may be completed with absorption promoting or retarding additives.

Syrups or elixirs or drops can be prepared by using, besides the active ingredient, sweeteners, methyl- or propyl-paraben and, if desired, tasting additives, by mixing the aqueous solution of the active ingredient therewith.

For rectal administration, suppositories can be prepared by using the suitable auxiliaries, such as cocoa butter or polyethylene glycol.

Compositions suitable for parenteral administration can be the injections, prepared by dissolving the active ingredient in sterile isotonic saline solution, or aqueous suspensions, which can be prepared by using suitable dispersing and wetting agents, such as propylene glycol or butylene glycol.

The creams and ointments for topical use can be prepared by using primary or secondary alcohols, such as cetyl alcohol, stearyl alcohol, glycerin, natural fats and oils, such as olive oil, wheat germ oil, lanolin, longer hydrocarbons, such as vaseline as well as cellulose derivatives. These compositions may also contain preservatives, such as methyl-p-hydroxy benzoate.

The composition for use as cosmetics or medical cosmetics can be prepared in a similar way. Preferably, the lipophylic components are mixed, and the water-soluble components are dissolved in water, optionally by slight warming. If desired, the pH of the latter is adjusted to the suitable value and the emulsion thus obtained is stirred until cooling. The active ingredient is added to the mixture of the mixture thus obtained in the form of aqueous solution.

The pharmaceutical and cosmetical compositions, which contain the novel hydroxylamine derivatives described in details under 4.1. in this specification can be prepared according to the above processes as well. These compositions form also an object of the invention.

One embodiment of the pharmaceutical and cosmetical compositions according to the invention contains hydroxylamine derivatives according to the formula (I) in an amount of 0.5 to 99.5% by weight together with carriers and auxiliaries generally used in such compositions, wherein X is halo, preferably chloro or bromo, Z is chemical bond, and a1) A is a group of the formula (a), wherein $Y^1$ is halo, alkoxy, haloalkyl or nitro and n is 1, 2 or 3, or an O-containing heteroaryl group, preferably furyl, S-containing heteroaryl, preferably thienyl, or an N-containing heteroaromatic group optionally condensed with a benzene ring, or the N—$C_{1-4}$ alkyl quaternary derivative or N-oxide thereof, preferably piridyl, quinolyl or isoquinolyl, R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is —$OR^7$, wherein $R^7$ is H or acyl, preferably unsubstituted or substituted alkylcarbonyl, arylcarbonyl or aminoacyl, k is 1, 2 or 3 and m is 1, 2 or 3, or an N—$C_{1-4}$ alkyl quaternary derivative or N-oxide thereof, with the proviso, that when A is piridyl or naphtyl, or a group of the formula (a) wherein $Y^1$ is halo or alkoxy, then $R^7$ is other than H, or a2) A is a group of the formula (c), R is a group of the formula (d) and the optional substituents $Y^2$ and $Y^3$ from which at least one must be present in the molecule, is oxygen or $C_{1-4}$ alkyl, and k is 1, 2 or 3 and m is 1, 2 or 3, and when the compound is a mono- or bivalent cation, the anion is one or two halide ion, preferably iodide, or X is —$NR^1R^2$, wherein $R^1$ and $R^2$, independently from each other, are H, unsubstituted or substituted straight or branched alkyl, unsubstituted or substituted aryl, preferably phenyl, unsubstituted or substituted aralkyl, or $R^1$ and $R^2$ together with the N-atom adjacent thereto, form a 3 to 7-membered, preferably 5 to 7-membered heterocyclic ring, which may contain one or more additional hetero atom(s), A is unsubstituted or substituted aryl, preferably phenyl, or unsubstituted or substituted aralkyl, Z is oxygen or =$NR^3$, wherein $R^3$ is H or unsubstituted or substituted alkyl, and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl or arylcarbonyl, k is 1, 2 or 3 and m is 1, 2 or 3, or X is —OQ, wherein Q is unsubstituted or substituted alkyl or aralkyl, Z is oxygen and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl, arylcarbonyl or aminoacyl, k is 1, 2 or 3 and m is 1, 2 or 3, or A is unsubstituted or substituted aryl, preferably phenyl or an N-containing heteroaromatic group, preferably piridyl or an S-containing heteroaromatic group, Z is a chemical bond, X is —OQ, wherein Q is $C_{1-4}$ alkyl, and R is a group of the formula (b), wherein $R^5$ and $R^6$, independently from each other are H, straight or branched alkyl, preferably C1-.J alkyl or cycloalkyl, or $R^5$ and $R^6$ together with the N-atom adjacent thereto form a 3 to 7-membered, preferably 5 to 7-membered saturated heterocyclic ring, $Y^6$ is H, k is 1, 2 or 3 and m is 1, 2 or 3.

Another group of the pharmaceutical and cosmetical compositions according to the invention includes those which, together with pharmaceutically and cosmetically acceptable carriers and/or auxiliaries contain in an amount of about 0.5 to 99.5% by weight a hydroxylamine derivative of the formula (I) or the salts and/or the optically active stereoisomers thereof, wherein X is —$NR^1R^2$, wherein $R^1$ and $R^2$, independently from each other, are H or unsubstituted or substituted straight or branched alkyl, preferably $C_{1-6}$ alkyl or cycloalkyl or, $R^1$ and $R^2$ together with the N-atom adjacent thereto form a 3-7-membered, preferably 5 to 7-membered saturated hetero ring, A is unsubstituted or substituted aralkyl, preferably phenylalkyl substituted with one or more alkoxy, preferably $C_{1-4}$ alkoxy, unsubstituted phenyl or phenyl substituted with one or more halo, alkyl or haloalkyl, acylamino or nitro, or unsubstituted or substituted N-containing heteroaromatic group which is optionally condensed with a benzene ring, preferably pirrolyl, piridyl, isoquinolyl or quinolyl, or an S-containing heteroaryl group, preferably thienyl, wherein the heteroaryl groups may have one or more substituents, preferably one or more alkyl, preferably $C_{1-4}$ alkyl, Z is a chemical bond, and R is a group of the formulae (e), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring which may contain additional hetero atoms and may have substituent(s), preferably $C_{1-4}$ alkyl, $Y^4$ is H or unsubstituted or substituted $C_{1-4}$ alkyl, $Y^5$ is H, unsubstituted or substituted $C_{1-4}$ alkyl or —$OR^7$, wherein $R^7$ is H or acyl, k is 1, 2 or 3 and m is 1, 2 or 3, with the proviso that when A is unsubstituted phenyl or phenyl substituted with halo or alkoxy or phenylalkyl substituted with alkoxy or a piridyl group and $R^7$ is H, at least one of $R^1$ and $R^2$ is other than H, and when A is unsubstituted phenyl or phenyl substituted with halo or alkoxy or phenylalkyl substituted with alkoxy or a piridyl group, and R and $R^2$ are both H, $R^7$ is other than H.

Another group of the pharmaceutical and cosmetical compositions according to the invention includes those which, together with pharmaceutically and cosmetically acceptable carriers and/or auxiliaries contain in an amount of about 0.5 to 99.5% by weight a hydroxylamine derivative of the formula (II) or the salts and/or the optically active stereoisomers thereof, wherein X is oxygen, A is $C_{1-20}$ straight or branched alkyl, unsaturated or saturated aryl, preferably phenyl or haloalkyl-phenyl, unsubstituted or substituted aralkyl, naphtyl or an N-containing heteroaromatic group, preferably piridyl, Z is a chemical bond, R' is H, $C_{1-4}$ alkyl or aralkyl, preferably phenylalkyl, and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —$OR^7$, wherein $R^7$ is H, k is 1, 2 or 3 and m is 1, 2 or 3, with the proviso that when A is other than alkyl and R' is H, $Y^6$ is H, or X is =$NR^4$, wherein $R^4$ is H, unsubstituted or substituted alkyl or unsubstituted or substituted aryl, preferably phenyl, or unsubstituted or substituted aryl, preferably phenylalkyl, A is unsubstituted or substituted alkyl or unsubstituted or substituted aryl, preferably phenyl or substituted phenyl, or unsubstituted or substituted aralkyl, preferably phenylalkyl, or cycloalkyl, Z is a chemical bond, oxygen or =$NR^3$, wherein $R^3$ is H or unsubstituted or substituted alkyl, R' is unsubstituted or substituted alkyl or unsubstituted or substituted aryl, preferably phenyl, or unsubstituted or substituted aralkyl, preferably phenylalkyl, and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl or arylcarbonyl, k is 1, 2 or 3 and m is 1, 2 or 3, or X is oxygen, A is unsubstituted or substituted alkyl, unsubstituted or substituted aralkyl, preferably phenylalkyl, Z is oxygen, R' is alkyl or aralkyl, preferably phenylalkyl, R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —$OR^7$, wherein $R^7$ is H or acyl, preferably unsubstituted or substituted alkylcarbonyl or arylcarbonyl, k is 1, 2 or 3 and m is 1, 2 or 3, or X is oxygen, Z is =NH, and d1) A is unsubstituted or substituted alkyl, cycloalkyl, unsubstituted or substituted aralkyl, preferably phenylalkyl, unsubstituted phenyl or phenyl substituted with halo, haloalkyl, alkoxy or nitro, R' is alkyl or aralkyl, preferably phenylalkyl, and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —OH, k is 1, 2 or 3 and m is 1, 2 or 3, or d2) A is a group of the formula (a) wherein $Y^1$ is haloalkyl, preferably trifluoromethyl and n is 1, 2 or 3, R' is H and R is a group of the formula (b), wherein $R^5$ and $R^6$, independently from each other are H, straight or branched alkyl, preferably $C_{1-4}$ alkyl or cycloalkyl, or $R^5$ and $R^6$ together with the N-atom adjacent thereto form a 3 to 7-membered, preferably 5 to 7-membered saturated heterocyclic ring, $Y^6$ is H or —OH, k is 1, 2 or 3 and m is 1, 2 or 3.

Another group of the pharmaceutical and cosmetical compositions according to the invention includes those which, together with pharmaceutically and cosmetically acceptable carriers and/or auxiliaries contain in an amount of about 0.5 to 99.5% by weight a hydroxylamine derivative of the formula (I") or the salts and/or the optically active stereoisomers thereof, wherein A is unsubstituted phenyl or phenyl substituted with halo or nitro or an N-containing heteroaryl group, preferably piridyl, R' is H and R" is an ω-amino-alkyl group which may be mono- or disubstituted, wherein the alkyl chain contains 1 to carbon atoms and the amino-substituents, independently from each other are one or two straight or branched alkyl or cycloalkyl, or wherein the two amino-substituent together with the N-atom adjacent thereto form a 3 to 7-membered, preferably 5 to 7-membered heterocyclic ring or the N—$C_{1-4}$ alkyl quaternary derivative thereof, with the proviso that when A is piridyl, R" is other than 1-piperidinylmethyl.

The embodiments of the invention are illustrated in the following examples more in details. It should be understood, however, that the scope of protection is not limited to the specific embodiments set forth in the Examples.

Chemical and Composition Examples

Example 1

N-[2-hydroxy-3-(1-piperidinyl)propoxyl]-2-thiophenecarboximidoyl chloride monohydrochloride 5.0 g (15.6 mmol) of N-[2-hydroxy-3-(1-piperidinyl)propoxy]-2-thiophenecarboximidamide monohydrochloride (Example 44) was dissolved in 19 ml of water, then 6.1 ml of concentrated hydrochloric acid was added. The solution was cooled to −5° C., then a cold solution of 4.4 g (63.8 mmol) of sodium nitrite in 2.4 ml of water was added dropwise. Throughout the reaction the internal temperature was maintained at 0° C. When addition was completed the mixture was stirred for a further one hour. Cold benzene (60 ml) was added and the mixture was made alkaline with slow addition of a cold solution of 3.2 g (80 mmol) of sodium hydroxide in 45 ml of water. The organic phase was separated and washed successively with 20 ml portions of water until the pH<9 (3-5 times). The organic solution was dried over anhydrous sodium sulfate, treated with charcoal, filtered and evaporated in vacuum (t<45° C.) to give 2.6 g of oil. This residue was dissolved in 5 ml of isopropyl alcohol and acidified (pH 2) with isopropyl alcohol containing dry hydrochloric acid. The product was crystallized from n-hexane to give off-white material.

Yield: 2.0 g (38%)
Mp.: 115-123° C.

Following the process described in the previous example the following compounds were prepared:

Example 2

N-[2-hydroxy-3-(1-piperidinyl)propoxy]-1-isoquinolinecarboximidoyl chloride monohydrochloride Starting Material: Example 46
Yield: 48%
Mp.: 168-172° C.
IR (KBr): 3425, 3128, 2947, 2866, 2650, 2540, 1622, 1597, 1556, 1452, 1385, 1364, 1329, 1296, 1281, 1240, 1117, 1092, 1024, 1015, 978, 953, 903, 881, 795, 743, 718, 658, 559 $cm^{-1}$ Example 3

N-[2-hydroxy-3-(1-piperidinyl)propoxy]-3-quinolinecarboximidoyl chloride (Z)-2-butenedioate (1:1)

Starting Material: Example 42
In this case the final product was isolated at the end of the work-up procedure by dissolving the crude base in acetone, and adding an equivalent amount of maleic acid.
Yield: 67%
Mp.: 159-162° C.
IR (KBr): 3427, 3019, 2947, 2886, 2689, 1583, 1477, 1450, 1352, 1293, 1221, 1194, 1132, 1072, 1045, 939, 919, 872, 833, 754, 650, 557 $cm^{-1}$ Example 4

N-[2-hydroxy-3-(1-piperidinyl)propoxy]-3-nitro-benzenecarboximidoyl chloride monohydrochloride Starting material: Example 40
Yield: 58%
Mp.: 185-189° C.

Example 5

N-[2-hydroxy-3-(1-piperidinyl)propoxy]-4-nitro-benzenecarboximidoyl chloride monohydrochloride Starting material: Example 43
Yield: 47%
Mp.: 180-182° C.
IR (KBr): 3331, 2953, 2853, 2735, 2654, 2577, 2548, 1605, 1568, 1516, 1456, 1348, 1261, 1165, 1119, 1072, 1059, 1007, 960, 933, 862, 849, 754, 719, 690, 673, 627, 581, 550, 478 $cm^{-1}$ Example 6

N-[2-hydroxy-3-(1-piperidinyl)propoxy]-2-nitro-benzenecarboximidoyl chloride monohydrochloride Starting material: Example 45
Yield: 50%
Mp.: 159-162° C.
IR (KBr): 3298, 2983, 2932, 2746, 1593, 1574, 1535, 1445, 1391, 1354, 1317, 1288, 1242, 1198, 1117, 1092, 1069, 1020, 968, 947, 914, 852, 793, 756, 708, 577 $cm^{-1}$ Example 7

N-[2-hydroxy-3-(1-piperidinyl)propoxy]-2-furanecarboximidoyl chloride monohydrochloride Procedure:

1-Chloro-2-hydroxy-3-(1-piperidinyl)-propane [J. Org. Chem. 33(2) p. 523-30 (1968)](3.0 g, 116.9 mmol) was dissolved in water (1.8 ml). Solid NaOH (1.19 g, 29.8 mmol) was added, and the mixture was stirred at room temperature for 1 hour. N-Hydroxy-2-furanecarboximidamide (1.92 g, 15.2 mmol) was added, and the mixture was kept on stirring at room temperature overnight. Concentrated HCI (2.1 ml) was added to adjust the pH to approx. 4, and the solution was evaporated in vacuum to dryness.

The residue (5.4 g) was dissolved in cc. HCI (37 ml), cooled to 0-5° C., and an aqueous solution of $NaNO_2$ (5.6 g, 80 mmol in 23 ml water) was added dropwise in 30 min. The solution was made alkaline then by addition of 2N NaOH solution (102 ml) to pH=10, and extracted with ethyl acetate (2×130 ml). The combined organic phases were washed with water, dried over anh. $Na_2SO_4$ and evaporated. The residue (2.0 g) was redissolved in a small volume of ethyl acetate (20 ml) and the product was precipitated by addition of isopropanolic HCI solution (3.2 N, 3 ml). The obtained white precipitate was filtered, washed, and finally recrystallized from isopropanol.

Yield: 11%

Mp.: 139-141° C.

IR (KBr): 3427, 3267, 3094, 2955, 2922, 2964, 2745, 1637, 1584, 1479, 1452, 1391, 1319, 1281, 1259, 1157, 1117, 1074, 1024, 999, 980, 943, 887, 854, 843, 743, 710, 596 cm$^{-1}$

Following the process described in the previous example the following compound was prepared:

Example 8

N-[2-hydroxy-3-(1-piperidinyl)propoxy]-4-pyridinecarboximidoyl chloride (Z)-2-butenedioate (1:1)

In this case the final product was isolated at the end of the work-up procedure by dissolving the crude base in acetone, and adding an equivalent amount of maleic acid.

Yield: 25%

Mp.: 165.5-169° C.

Example 9

N-[3-[(1,1-Dimethylethyl)amino]-2-hydroxypropoxy]-3-trifluoromethylbenzene-carboximidoyl chloride monohydrochloride Procedure:

50 g (0.245 mol) of m-trifluoromethyl-benzamidoxime and 33.7 g (0.6 mol) of potassium hydroxide was dissolved in a mixture of dimethyl sulphoxide and 170 ml of water, and the mixture was cooled to 0° C. 48 ml (0.6 mol) of epichlorohydrine was added, and the reaction mixture was stirred at 0° C. for 5 hours, then kept in a refrigerator overnight. Next day 250 ml of water was added, and the mixture was extracted with ethyl acetate (4×250 ml). The combined organic phases were washed with water, dried, treated with charcoal and evaporated to dryness, to yield m-trifluoromethyl-N-(2,3-epoxypropoxy)-benzamidine, as a colorless oil.

Yield: 61 g (96%)

To the obtained oil 400 ml of 18% of hydrochloric acid solution and 60 ml of ether were added, and the mixture was cooled to –5° C., while stirring. 17.4 g (0.25 mol) of sodium nitrite, dissolved in 60 ml of water was added slowly in 40 min., and the reaction mixture was stirred for another 20 minutes. The mixture was extracted then with ether (2×160 ml), and the combined organic phases were washed with water twice. To the ethereal solution 340 ml of 20% of sodium hydroxide solution was added, and the two-phase system was refluxed for 1 hour, while stirring. The phases were then separated, the organic layer was washed with brine until neutral, dried and evaporated to dryness to give m-trifluoromethyl-N-(2,3-epoxypropoxy)-benzimidoyl chloride, as a colorless oil.

Yield: 30.5 g (45%)

A mixture of 1.19 g (4.2 mmol) N-[(2,3-epoxy)propoxy]-3-trifluoromethyl-benzenecarboximidoyl chloride and 0.89 ml (8.5 mmol) of tertbutylamine in 12 ml of isopropyl alcohol was refluxed for 2 hours. Solvent was removed under reduced pressure. The residue was dissolved in ethyl acetate, and 0.98 ml of methanolic hydrogen chloride solution (4.3 N) was added and the mixture was concentrated to small volume under vacuum, then diluted with ether. The precipitate that formed was recovered, washed with cold ether and dried.

Yield: 0.48 g (32%)

Mp.: 150-153° C.

IR (KBr): 3423, 3233, 2978, 2880, 2784, 1620, 1570, 1479, 1441, 1400, 1383, 1340, 1238, 1167, 1128, 1101, 1072, 1038, 982, 930, 897, 804, 787, 714, 694 cm$^{-1}$

Following the process described in the previous example the following compounds were prepared:

Example 10

N-[2-hydroxy-3-[(1-methylethyl)amino]propoxy]-3-trifluoromethyl-benzene-carboximidoyl chloride monohydrochloride Yield: 30%

Mp.: 105-108° C.

IR (KBr): 3358, 2984, 2883, 2804, 1595, 1441, 1383, 1335, 1238, 1184, 1171, 1121, 1099, 1074, 1011, 995, 947, 906, 891, 798, 779, 696, 681, 567 cm$^{-1}$

Example 11

N-[3-(cyclohexylamino)-2-hydroxypropoxy]-3-trifluoromethyl-benzenecarboximidoyl chloride monohydrochloride Yield: 35%

Mp.: 147-149.5° C.

IR (KBr): 3381, 2951, 2860, 2820, 1580, 1439, 1344, 1246, 1161, 1126, 1099, 1074, 1003, 986, 932, 903, 872, 802, 787, 716, 692, 681, 648 cm$^{-1}$

Example 12

N-[3-(diethylamino)-2-hydroxypropoxy]-3-trifluoromethyl-benzenecarboximidoyl chloride monohydrochloride Yield: 21%

Mp.: 121-128° C.

IR (KBr): 3425, 3289, 2951, 2667, 1818, 1443, 1337, 1238, 1178, 1115, 1078, 1049, 997, 910, 804, 781, 696, 683 cm$^{-1}$

Example 13

N-[2-hydroxy-3-(1-piperidinyl)propoxy]-3-trifluoromethyl-benzenecarboximidoyl chloride monohydrochloride Yield: 13%

Mp.: 119-123° C.

IR (KBr): 3366, 2937, 2854, 2737, 2673, 2538, 1616, 1570, 1439, 1404, 1337, 1290, 1236, 1199, 1165, 1129, 1101, 1074, 1030, 984, 972, 933, 901, 829, 804, 788, 717, 699, 685, 646 cm$^{-1}$

Example 14

N-[2-hydroxy-3-(piperidinyl-1-oxide-1-yl)propoxy]-N'-oxy-3-pyridinecarboximidoyl chloride Procedure:

To a solution of N-[2-hydroxy-3-(1-piperidinyl)propoxy]-3-pyridinecarboximidoyl chloride (5.0 g; 17.1 mmol) in chloroform (50 ml) m-chloroperbenzoic acid (7.0 g; 40 mmol) was added in small portions, and the mixture was stirred at room temperature for 2 hours. The solvent was removed, the residue was dissolved in 80 ml of ethyl acetate, extracted with water, dried and evaporated. The obtained oily product was finally crystallized with acetone to give the product as an off-white solid.

Yield: 2.21 g (6.7 mmol; 40%)

Mp.: 140-142° C.

IR (KBr): 3437, 3071, 2943, 2880, 2590, 1801, 1578, 1475, 1454, 1433, 1375, 1294, 1259, 1194, 1165, 1121, 1088, 1043, 1011, 995, 924, 905, 888, 845, 808, 710, 671, 554, 513, 413 cm$^{-1}$

Example 15

N-[2-hydroxy-3-(piperidin-1-oxide-1-yl)propoxy]-3-pyridinecarboximidoyl chloride Procedure:

To a solution of N-[2-hydroxy-3-(1-piperidinyl)propoxy]-3-pyridinecarboximidoyl chloride (2.0 g; 6.8 mmol) in chloroform (20 ml) m-chloroperbenzoic acid (1.6 g of 70% purity; 6.5 mmol) was added, and the mixture was stirred at room temperature for 30 minutes. The solution was made alkaline with 10% of sodium hydroxide solution, then separated, and the organic layer was washed with brine, dried and evaporated. The solid residue was recrystallized with ethyl acetate, the precipitate was filtered off, washed and dried, to give the product as a white solid.

Yield: 1.03 g (48%)

Mp.: 127-130° C.

IR (KBr): 3454, 2988, 2945, 2880, 2585, 1585, 1512, 1479, 1443, 1416, 1393, 1350, 1331, 1289, 1183, 1134, 1072, 1051, 1030, 997, 953, 939, 879, 847, 808, 702, 519, 417 cm$^{-1}$

Example 16

N'-[2-hydroxy-3-(1-methyl-1-piperidinium-1-yl)propoxy]-N-methyl-pyridinium-3-carboximidoyl chloride diiodide Procedure:

A mixture of N-[2-hydroxy-3-(1-piperidinyl)propoxy]-3-pyridinecarboximidoyl chloride (1.0 g; 3.4 mmol) and 1.2 ml (20 mmol) of methyl iodide was refluxed in acetone (10 ml) under nitrogen for 2 hours. The resulting dark yellow precipitate was filtered off, and washed with acetone to give the crude product (1.8 g) which was then recrystallized from 20 ml of ethanol.

Yield: 1.2 g (60%)

Mp.: 153-157° C.

IR (KBr): 3462, 3406, 3317, 3040, 2941, 2878, 2831, 1729, 1636, 1589, 1504, 1462, 1378, 1350, 1290, 1209, 1171, 1121, 1069, 1047, 1030, 1001, 941, 897, 868, 818, 706, 673, 635, 589 cm$^{-1}$

Example 17

N-[2-acetoxy-3-(1-piperidinyl)propoxy]-3-pyridinecarboximidoyl chloride (Z)-2-butenedioate (1:1)

Procedure:

1.48 g (5.0 mmol) of N-[2-hydroxy-3-(1-piperidinyl)propoxy]-3-pyridine-carboximidoyl chloride was dissolved in 5 ml of acetic anhydride. The temperature of the reaction was raised up to 40° C. After 30 minutes at room temperature the solvent was completely removed in vacuum, the residue was dissolved in 30 ml of diethyl ether, treated with charcoal, filtered and the solvent was removed under reduced pressure to give 1.74 g of orange-colored oil.

The residue was dissolved in 10 ml of acetone, and a solution of 0.6 g (5.17 mmol) of maleic acid in 10 ml of acetone was added. The crystalline product was removed by filtration and washed with acetone to give 1.43 g off-white material. Recrystallization, with decolorization, from 9 ml of isopropyl alcohol produced the title compound.

Yield: 1.22 g (54%)

Mp.: 143-144° C.

Example 18

(S)—N-[2-[2-®-(1,1-dimethylethyloxycarbonylamino)-3-phenylpropionyloxyl-3-(1-piperidinyl)propoxy]-3-pyridinecarboximidoyl chloride (Z)-2-butenedioate (1:1)

Procedure:

6.7 g (25.5 mmol) of N-(tert-butoxycarbonyl)-D-phenylalanine was dissolved in 50 ml of dichloromethane. The solution was cooled to 0° C., and 4.0 ml of triethylamine and then 2.5 ml (26 mmol) of ethyl chloroformate was added dropwise. The mixture was stirred for 20 minutes at 0° C., then a solution of 7.5 g (26 mmol) of N-[2-hydroxy-3-(1-piperidinyl)propoxy]-3-pyridinecarboximidoyl chloride in 50 ml of dichloromethane was added in 30 minutes. The reaction mixture was stirred at room temperature for 1 hour. The solution was extracted first with 10% acetic acid (2×100 ml), then with water, dried with anhydrous sodium sulfate, and evaporated to dryness. The residue (10.7 g) was dissolved in 71 ml of acetone and 1.53 g (13 mmol) of maleic acid was added. The resulting solid was filtered off and washed with acetone.

Yield: 4.0 g (6.0 mmol; 23%)

Mp.: 146.5-148° C.

$[\alpha]_D$=+21.5° (c=1, MeOH)

IR (KBr): 3393, 2978, 1744, 1697, 1582, 1518, 1468, 1454, 1420, 1381, 1358, 1313, 1290, 1256, 1213, 1169, 1126, 1099, 1084, 1045, 1016, 930, 908, 870, 750, 690, 575 cm$^{-1}$

Following the process described in the previous example the following compound was prepared:

Example 19

(R)—N-[2-[2-(S)-(1,1-dimethylethyloxycarbonylamino)-3-phenylpropionyloxy-3-(1-piperidinyl)propoxy]-3-pyridinecarboximidoyl chloride (Z)-2-butenedioate (1:1)

Yield: 25%

This compound has the same physical data (Mp.; IR) as written in Example 18.

$[\alpha]_D$=−23.6° (c=1, MeOH)

Example 20

N-[2-benzoyloxy-3-(1-piperidinyl)propoxy]-3-pyridinecarboximidamide (Z)-2-butenedioate (1:1)

Procedure:

20.9 g (75.0 mmol) of N-[2-hydroxy-3-(1-piperidinyl)propoxy]-3-pyridine-carboximidamide [Hung. Pat. 177.578 (1976)] was dissolved in 300 ml of benzene. To this solution 150 ml of 1 N sodium hydroxide solution was added, followed by dropwise addition of 19.5 ml (168 mmol) of benzoyl chloride. After stirring the mixture intensively for 2 hours, 7.1 g (67 mmol) of sodium carbonate and a further portion of benzoyl chloride (9.75 ml; 84 mmol) was added, and the stirring was continued overnight. The phases were then separated, the organic layer was extracted with 1 N sodium hydroxide solution and water, dried and evaporated to dryness. The residue (41 g oil) was dissolved in 150 ml of acetone, and 8.7 g (75 mmol) maleic acid was added. The obtained precipitate was filtered off, washed with acetone, and dried.

Yield: 29.1 g (78%)
Mp.: 194-195° C.

Following the process described in the previous example the following compound was prepared:

Example 21

N-[2-benzoyloxy-3-(1-piperidinyl)propoxy]-3-pyridinecarboximidoyl chloride (Z)-2-butenedioate (1:1)

Starting material: U.S. Pat. No. 5,147,879 (1992)
Yield: 64%
Mp.: 134-136° C.
IR (KBr): 2955, 2939, 2517, 1718, 1583, 1477, 1452, 1410, 1370, 1354, 1317, 1268, 1209, 1173, 1117, 1057, 1043, 998, 968, 939, 903, 870, 748, 723, 714, 652, 582 cm$^{-1}$ Example 22

N-[2-palmitoyloxy-3-(1-piperidinyl)propoxy]-3-pyridinecarboximidamide monohydrochloride Procedure:

14.7 g (52.8 mmol) of N-[2-hydroxy-3-(1-piperidinyl)propoxy]-3-pyridine-carboximidamide [Hung. Pat. 177.578 (1976)] was dissolved in 160 ml of chloroform. 7.7 ml (55 mmol) of triethylamine was added, followed by dropwise addition of a solution of palmitoyl chloride (14.7 g; 56.5 mmol) in 85 ml of chloroform. The mixture was stirred overnight at room temperature. Next day further amount of 3.8 ml of triethylamine and 7.4 g of palmitoylchloride was added, and the stirring was continued for one more day. The solution was extracted then with water, 5% acetic acid and water, successively, dried over anh. sodium sulfate, and evaporated to dryness.

The residue (28.2 g oil) was dissolved in ethyl acetate, and the product was precipitated by addition of 30 ml of 1 N HCl/ethyl acetate. The thick, white precipitate was filtered off, washed with ethyl acetate and dried.

Yield: 10.9 g (37%)
Mp.: 110-113° C.

Following the process described in the previous example the following compounds were prepared:

Example 23

N-[2-palmitoyloxy-3-(1-piperidinyl)propoxy]-3-pyridinecarboximidoyl chloride dihydrochloride Starting material: U.S. Pat. No. 5,147,879 (1992)

Note: the reaction was carried out by refluxing.
Yield: 72%
Mp.: 69-73.5° C.
IR (KBr): 3425, 2922, 2853, 2648, 2544, 1742, 1632, 1468, 1416, 1377, 1287, 1183, 1113, 1087, 1032, 984, 708, 675 cm$^{-1}$ Example 24

N-[2-(2-furoyloxy)-3-(1-piperidinyl)propoxy]-3-pyridinecarboximidamide (Z)-2-butenedioate (1:1)

Note: the product was isolated in the form of maleate salt.
Yield: 52%
Mp.: 167-171.5° C.

Example 25

N-[2-(o-chlorobenzoyloxy)-3-(1-piperidinyl)propoxy]-3-pyridinecarboximidamide monohydrochloride Note: the reaction was carried out by refluxing.
Yield: 50%
Mp.: 91-94° C.

Example 26

N-[2-(p-methoxybenzoyloxy-3-(1-piperidinyl)propoxy]-3-pyridinecarboximidamide monohydrochloride Note: the reaction was carried out by refluxing.
Yield: 71%
Mp.: 152-155° C.

Example 27

N-[2-(m-trifluromethylbenxoyloxy)-3-(1-piperidinyl)propoxy]-3-pyridine-carboximidamide monohydrochloride Note: the reaction was carried out by refluxing.
Yield: 45%
Mp.: 144-147° C.

Example 28

N-[2-(2-thenyloxy)-3-(1-piperidinyl)propoxy]-3-pyridinecarboximidamide (Z)-2-butenedioate (1:1)

Note: the reaction was carried out by refluxing, and the product was isolated in the form of maleate salt.
Yield: 58%
Mp.: 168-176° C.

Example 29

N-[2-acetoxy-3-[(1-piperidinyl)propoxy]-3-pyridinecarboximidamide monohydrochloride Procedure:

2.5 g (9.0 mmol) of N-[2-hydroxy-3-(1-piperidinyl)propoxy]-3-pyridinecarboximidamide was dissolved in 27 ml of chloroform, 1.6 g (16 mmol) of acetic anhydride was added and stirred at room temperature for 1 hour. The reaction mixture was evaporated to dryness, and dissolved in isopropyl alcohol containing the equimolar quantity (9 mmol) of dry hydrogen chloride. The solution was cooled and the solid were filtered. Recrystallization from isopropyl alcohol gave white crystalline compound.

Yield: 1.9 g (59%)
Mp.: 107° C.

Example 30

N-[2-(3-pyridinecarbonyloxy)-3-(1-piperidinyl)]propoxy-3-pyridinecarboximidamide-(Z)-2-butenedioate (1:1)

Procedure:

To a solution of N-[2-hydroxy-3-(1-piperidinyl)propoxy]-3-pyridinecarboximid-amide (1.68 g; 6 mmol) in dry pyridine 1.68 g (7.4 mmol) of nicotinic anhydride was added and kept at room temperature overnight. The mixture was evaporated, the residue was dissolved in 30 ml of ethyl acetate, filtered, the filtrate was extracted with 10% $NaHCO_3$ solution, dried and evaporated. The obtained oil was dissolved in 20 ml of acetone, and 0.53 g of maleic acid was added to result in precipitation. The product was filtered off and washed with acetone.

Yield: 1.84 g (61%)
Mp.: 157-160° C.

Example 31

N-[3-(1-piperidinyl)propoxy]-3-pyridinecarboximidamide dihydrochloride

Procedure:

2.86 g (51.1 mmol) of potassium hydroxide was dissolved in 20 ml of abs. ethanol, then 6.45 g (47.0 mmol) N-hydroxy-3-pyridinecarboximidamide and 7.7 g (47.7 mmol) 1-chloro-3-(1-piperidinyl)-propane were added and refluxed for 9 hours. The solid was removed by filtration and the filtrate was evaporated. The crude product was dissolved in 100 ml of chloroform, washed with 1 N of sodium hydroxide solution then three times of water. The organic layer was dried over sodium sulfate, filtered and the solvent was evaporated under reduced pressure. The residue was dissolved in a small amount of abs. ethanol and isopropyl alcohol containing dry hydrochloric acid was added (pH 2) to afford off-white crystals.

Yield: 4.8 g (38%)
Mp.: 95-100° C. (dec.)
IR (KBr, base): 3422, 3294, 3107, 2984, 2937, 2870, 2818, 1649, 1616, 1593, 1479, 1462, 1441, 1381, 1309, 1194, 1123, 1094, 1059, 1042, 982, 910, 858, 816, 712, 559 $cm^{-1}$ Following the process described in the previous example the following compounds were prepared:

Example 32

N-[3-(1-piperidinyl)propoxy]-3-trifluoromethyl-benzenecarboximidamide monohydrochloride Yield: 42%
Mp.: 116-119° C.
IR (KBr, base): 3412, 3082, 2949, 2874, 2827, 1655, 1485, 1447, 1383, 325, 1283, 1171, 1121, 1094, 1072, 986, 920, 905, 808, 700, 677, 627 $cm^{-1}$

Example 33

N-[3-(1-piperidinyl)propoxy]-(3,4-dimethoxyphenyl)methanecarboximidamide dihydrochloride Yield: 35%
Mp.: 207-209° C.

Example 34

N-[2,2-dimethyl-3-(1-piperidinyl)propoxy]-3-pyridinecarboximidamide

Yield: 38% (oil)
IR (KBr): 3323, 2935, 2888, 2785, 1637, 1477, 1393, 1360, 1157, 1111, 1057, 995, 943, 860, 814, 789, 708, 627 $cm^{-1}$

Example 35

N-[3-(4-methyl-1-piperazinyl)propoxy]-3-pyridinecarboximidamide monohydrochloride Yield: 23%
Mp.: 127-130° C.
IR (KBr): 3387, 2947, 2878, 2802, 1730, 1639, 1450, 1389, 1283, 1242, 1194, 1150, 1083, 1015, 964, 933, 814, 710 $cm^{-1}$

Example 36

N-[3-(1-piperidinyl)propoxy)-3-nitro-benzenecarboximidamide monohydrochloride

Yield: 51%
Mp.: 158-162° C.

Example 37

N-[3-(1-piperidinyl)propoxy]-benzenecarboximidamide dihydrochloride

Yield: 64%
Mp.: 207-209° C.

Example 38

N-[2-hydroxy-3-[(1-piperidinyl)propoxy]-2,4,6-trimethyl-benzenecarboximidamide

Yield: 44%
Mp.: 199-201° C.
IR (KEr): 3410, 3103, 2943, 2912, 2814, 2791, 1634, 1582, 1441, 1383, 1350, 1321, 1304, 1254, 1204, 1146, 1111, 1099, 1065, 993, 878, 851, 785, 754, 525 $cm^{-1}$

Example 39

N-[2-hydroxy-3-[(1-piperidinyl)propoxy]-4-acetamino-benzenecarboximidamide monohydrochloride Yield: 25%
Mp.: 133-137° C.

Example 40

N-[2-hydroxy-3-[(1-piperidinyl)propoxy]-3-nitro-benzenecarboximidamide dihydrochloride Yield: 38%

Mp.: 190-193° C.

Example 41

N-[2-hydroxy-3-[(1-piperidinyl)propoxy](1,5-dimethyl)-pyrrolcarboximidamide monohydrochloride Yield: 20%

Mp.: 144-147° C.

IR (KBr, base): 3458, 3369, 2930, 2849, 1622, 1587, 1502, 1468, 1437, 1396, 1354, 1323, 1279, 1254, 1200, 1157, 1115, 1078, 1042, 988, 962, 930, 870, 856, 758, 737, 694, 609 cm$^{-1}$

Example 42

N-[2-hydroxy-3-[(1-piperidinyl)propoxy]-3-quinolinecarboximidamide dihydrochloride Yield: 36%

Mp.: 210-211° C.

Example 43

N-[2-hydroxy-3-[1-piperidinyl)propoxy]-4-nitro-benzenecarboximidamide dihydrochloride Yield: 77%

Mp.: 184-189° C.

Example 44

N-[2-hydroxy-3-(1-piperidinyl)propoxy]-2-thiophenecarboximidamide dihydrochloride Yield: 73%

Mp.: 157-170° C.

IR (KBr): 3280 (b), 2940, 1655, 1420, 1120, 1018, 1002, 857, 710 cm$^-$

Example 45

N-[2-hydroxy-3-(1-piperidinyl)propoxy]-2-nitro-benzenecarboximidamide dihydrochloride Yield: 47%

Mp.: 200-208° C.

IR (KBr): 3300 (b), 2960, 1670, 1535, 1347, 1155, 1020, 1002, 860, 800, 753 cm$^{-1}$

Example 46

N-[2-hydroxy-3-(1-piperidinyl)propoxy]-1-isoquinolinecarboximidoyl dihydrochloride Yield: 56%

Mp.: 208-216° C.

Example 47

N-[3-[(1,1-dimethylethyl)amino]-2-hydroxypropoxy]-3-trifluoromethyl-benzenecarboximidamide dihydrochloride Procedure:

A mixture of 21.0 g (80.8 mmol) of m-trifluoromethyl-N-(2,3-epoxypropoxy)-benzamidine (Example 9/a), 105 ml of tert-butylamine, 210 ml of ether and 84 ml of 4 N sodium hydroxide solution was refluxed for 5 hours. The phases were separated, the ethereal layer was washed with brine, dried and evaporated to dryness. The resulting oil (25.8 g) was dissolved in 250 ml of acetone, treated with charcoal, then 39 ml of 4 N HCl/ethyl acetate solution was added, while stirring, resulting in precipitation of a white solid, which was filtered off and washed with acetone.

Yield: 22.8 g (70%)

Mp.: 186-192° C. (dec.)

IIR (KBr): 3418, 2984, 2785, 2625, 2527, 2401, 1664, 1585, 1487, 1437, 1381, 1329, 1173, 1155, 1130, 1078, 905, 874, 820, 692, 642, 594 cm$^{-1}$

Example 48

N-[2-hydroxy-3-(1-piperidinyl)propoxy]-N'-butyl-3-pyridinecarboximidamide monohydrochloride Procedure:

Preparation of N-[2-[(2-tetrahydropyranyl)oxy]-3-(1-piperidinyl)propoxy]-3-pyridinecarboximidoyl chloride (21.3 g, 71.4 mmol) of N-[2-hydroxy-3-(1-piperidinyl)propoxy]-3-pyridinecarboximidoyl chloride was dissolved in 500 ml of chloroform, acidified with ethereal hydrochloric acid solution to pH=3, then 32.6 ml (0.357 mol) of 3,4-dihydro-2H-pyrane was added. The mixture was stirred at room temperature for 20 hours, washed three times with 200 ml portions of 2 N sodium hydroxide solution and four times with the same amount of water. The organic phase was dried over sodium sulfate, filtered and evaporated under reduced pressure. The oily residue was dissolved in 600 ml of ethyl acetate and washed four times with 150 ml portions of a pH=5 buffer solution, The organic solution was dried, filtered and evaporated.

Yield: 24.5 g (90%)

A mixture of 3.7 g (9.68 mmol) of N-[2-[(2-tetrahydropyranyl)oxy]-3-(1-piperidinyl)propoxy]-3-(1-piperidinyl)propoxy]-3-pyridinecarboximidoyl chloride and 40 ml (0.41 mol) n-butylamine was refluxed for 3 hours. The excess of amine was evaporated in vacuum affording dark-brown oil, which was dissolved in 40 ml of ethanol containing 3.0 g of 4-toluenesulphonic acid and the mixture was heated at 60° C. for one hour. The solvent was removed under reduced pressure, the residue was made alkaline (pH 10) with 2 N of sodium hydroxide solution then extracted three times with chloroform. The organic solution was dried over sodium sulfate, filtered and the solvent was evaporated in vacuum. The dark oily residue was purified by chromatography to give the pure base, which was dissolved in 20 ml of ethanol and acidified with equivalent amount of dry hydrochloric acid dissolved in isopropyl alcohol to give the title compound as a pale-yellow crystalline solid.

Yield: 1.22 g (34%)

Mp.: 120-122° C.

IR (KBr, base): 3319, 3293, 3040, 2959, 2928, 2854, 2842, 2552, 1612, 1580, 1450, 1427, 1399, 1333, 1315, 1221, 1196, 1171, 1126, 1103, 1051, 1022, 964, 928, 899, 858, 829, 719, 692, 602 cm$^{-1}$ Following the process described in the previous example the following compound was prepared:

Example 49

N-[2-hydroxy-3-(1-piperidinyl)propoxy]-N'-cyclohexyl-3-pyridinecarboximidamide monohydrochloride Yield: 0.89 g (24%)

Mp.: 130-134° C.

IR (KBr): 3280, 2935, 2853, 2640, 1720, 1619, 1551, 1514, 1452, 1404, 1313, 1236, 1194, 1155, 1124, 1111, 1090, 1040, 978, 828, 735, 627 cm$^{-1}$

Example 50

N-[2-hydroxy-3-(1-piperidinyl)propoxy-N'-(1,1-dimethylethyl)-benzenecarboximidamide Procedure:

Into a solution of 0.92 g (5.2 mmol) of 1-chloro-2-hydroxy-3-(1-piperidinyl)-propane in 2 ml of water 0.42 g (10.4 mmol) sodium hydroxide was added and stirred for one hour. To this mixture was added 1.0 g (5.2 mmol) of N-hydroxy-N'-(1,1-dimethylethyl)-benzenecarboximidamide dissolved in 20 ml of ethanol and refluxed for 4 hours. Solvent was evaporated and 50 ml of water was added and three times was extracted with 50 ml portions of chloroform. The organic phase was dried over sodium sulfate, filtered and the solvent was evaporated in vacuum. The yellow oily residue was slowly crystallized in refrigerator. The crystals were triturated with diethyl ether and filtered off.

Yield: 0.55 g (31%)

Mp.: 134-137° C.

IR (KBr): 3427, 3254, 2929, 2853, 2814, 1739, 1603, 1510, 1445, 1391, 1367, 1302, 1281, 1190, 1140, 1117, 1094, 1067, 1036, 993, 963, 922, 841, 789, 716, 675 cm$^{-1}$

Example 51

N-[2-hydroxy-3-(1-piperidinyl)propoxy-N',N'-diethyl-3-pyridinecarboximidamide monohydrochloride Procedure:

0.66 g (16.6 mmol) of sodium hydroxide was dissolved in 25 ml of abs. ethanol, then 1.61 g (8.3 mmol) N-hydroxy-N',N'-diethyl-3-pyridinecarboximidamide and 1.48 g (8.3 mmol) 1-chloro-2-hydroxy-3-(1-piperidinyl)-propane were added and refluxed for 5 hours. Solvent was evaporated and 50 ml of water was added and three times was extracted with 50 ml portions of ethyl acetate. The organic layer was dried over sodium sulfate, filtered and the solvent was evaporated in vacuum. The yellow oily residue was purified by chromatography to give the pure base, which was 64 dissolved in 20 ml of ethyl acetate and acidified with equivalent amount of dry hydrochloric acid dissolved in ethyl acetate to give the title compound as a white crystalline solid.

Yield: 1.3 g (42%)

Mp.: 113-117° C.

Example 52

N-[2-hydroxy-3-(1-piperidinyl)propoxy]-hexadecanoicamide monohydrochloride

Procedure:

1.74 g (10 mmol) 1-aminooxy-2-hydroxy-3-(1-piperidinyl)propane was dissolved in 20 ml of chloroform and cooled to 0°. A solution of palmitoylchloride (2.85 g; 10 mmol) in 10 ml of chloroform was added dropwise in 10 min. After stirring the mixture for 15 minutes the obtained white precipitate was filtered off, washed with chloroform, and dried.

Yield: 3.2 g (71%)

Mp.: 147-150° C.

IR (KBr): 3242, 3090, 2951, 2916, 2849, 1730, 1653, 1520, 1472, 1439, 1371, 1300, 1229, 1169, 1136, 1099, 1070, 1009, 993, 962, 928, 858, 760, 719, 602, 471 cm$^{-1}$

Following the process described in the previous example the following compounds were prepared:

Example 53

N-[3-(1-piperidinyl)propoxy]-3-trifluoromethylbenzamide

Starting material: EP 365,364 (1990)

Yield: 69% (oil)

IR (KBr): 3425, 2941, 2864, 2775, 1674, 1614, 1566, 1520, 1483, 1441, 1393, 1337, 1319, 1277, 1187, 1129, 1072, 922, 914, 750, 698, 650 cm$^{-1}$

Example 54

N-[2-hydroxy-3-(1-piperidinyl)propoxy]naphthalene-1-carboxamide

Yield: 54%

Mp.: 104-107° C.

IR (KBr): 3375, 2934, 1641, 1593, 1564, 1439, 1340, 1325, 1113, 1026, 941, 810, 779 cm$^{-1}$

Example 55

N-[2-hydroxy-3-(1-piperidinyl)propoxy]-N'-heptylurea

Procedure:

To the solution of 1.23 g (7.1 mmol) of 1-aminooxy-2-hydroxy-3-(1-piperidinyl)-propane dissolved in 20 ml of chloroform 1.0 g (7.1 mmol) of heptyl isocyanate was added and the reaction mixture was stirred for 20 hours. Solvent was evaporated in vacuum and the residue was purified by chromatography to give pure colorless oil. White crystalline product was obtained by triturating with petroleum ether.

Yield: 81%

Mp.: 49-51° C.

Following the process described in the previous example the following compound was prepared:

Example 56

N-[2-hydroxy-3-(1-piperidinyl)propoxy]-N'-propyl-urea

Yield: 50% (oil)
IR (KBr): 3319, 2934, 2878, 2802, 1666, 1551, 1456, 1393, 1308, 1155 1092, 1040, 993, 889, 793 cm$^{-1}$

Example 57

N-cyclohexyl-N'-[2-hydroxy-3-(1-piperidinyl)propoxy]-urea

Yield: 67%
Mp.: 108-110° C.
IR (KBr): 3319, 3287, 3188, 2930, 2853, 2797, 1637, 1574, 1452, 1354, 1331, 1300, 1101, 1098, 991 cm$^{-1}$

Example 58

N-hexyl-N'-[2-hydroxy-3-(1-piperidinyl)propoxy]-urea

Yield: 27%
Mp.: 50-52° C.
IR (KBr): 3310, 2932, 2858, 2804, 1666, 1551, 1454, 1377, 1306, 1092, 1040, 995, 791, 725, 604 cm$^{-1}$

Example 59

N-(3-chlorophenyl)-N'-[2-hydroxy-3-(1-piperidinyl)propoxy]-urea

Yield: 34%
Mp.: 117-118° C.
IR (KBr): 3250, 2939, 2900, 1670, 1597, 1551, 1491, 1429, 1329, 1252, 1119 972, 775, 718, 700 cm$^{-1}$

Example 60

N-cyclohexyl-N'-[2-hydroxy-3-[N-cyclohexylcarbamoyl-N-(1,1-dimethylethyl)-amino]propoxy]-urea Yield: 44%
Mp.: 151-152° C.
IR (KBr): 3312, 2932, 2854, 1668, 1616, 1555, 1450, 1393, 1364, 1354, 1252, 1220, 1130, 941, 891 cm$^{-1}$

Example 61

N-hexyl-N'-[3-(1-piperidinyl)propoxy]-urea

Yield: 85% (oil)
IR (KBr): 3354, 2932, 2856, 2810, 2777, 1666, 1543, 1486, 1377, 1308, 1155, 1134, 1076 cm$^{-1}$

Example 62

N-tert-butyl-N'-[(2-hydroxy-3-(1-piperidinyl)propoxy)]-urea

Yield: 38%
Mp: 71-73° C.
IR (KBr): 3314, 2945, 2916, 1651, 1555, 1460, 1393, 1384, 1335, 1254, 1111, 988, 903, 839, 781 cm$^{-1}$

Example 63

N-(3-nitro-phenyl)-N'-[(2-hydroxy-3-(1-piperidinyl)propoxy)]-urea

Yield: 54%
Mp: 137-139° C.
IR (KBr): 3281, 2943, 2818, 1672, 1607, 1560, 1529, 1486, 1437, 1354, 1283, 1115, 802, 739 cm$^{-1}$

Example 64

5,6-Dihydro-5-(1-piperidinyl)methyl-3-(3-pyridyl)-4H-1,2,4-oxadiazine

Procedure:

17.5 g (0.05 mole) of N-[2-hydroxy-3-(1-piperidinyl)propoxy]-3-pyridinecarboximidamide dihydrochloride was dissolved in 50 ml of thionyl chloride, boiled for one hour, then the mixture was evaporated to dryness. The residue was dissolved in 300 ml of methanol, treated with charcoal and after filtration the solvent was evaporated in reduced pressure. The residue was dissolved in the minimum amount of ethanol and refrigerated to yield crystalline N-[2-chloro-3-(1-piperidinyl)propoxy]-3-pyridine-carboximidamide dihydrochloride as intermediate compound.

Yield: 13.2 g (71%)
Mp.: 127-145° C.

13.2 g (35.7 mmol) of N-[2-chloro-3-(1-piperidinyl)propoxy]-3-pyridinecarboximidamide dihydrochloride was added to a solution of 16.5 g (143.5 mmole) of potassium tert-butoxide dissolved in 150 ml of tert-butanol. The mixture was boiled for 6 hours, then evaporated in vacuum. 100 ml of 5% sodium hydroxide solution was added and the mixture was extracted three times with 300 ml portions of ethyl acetate.

The organic layer was dried over sodium sulfate, filtered and evaporated to dryness. The residue was triturated with diethyl ether to yield the title compound as white crystals.

Yield: 3.5 g (38%)
Mp.: 157.5-158° C.

Example 65

N-[3-[1,1-dimethylethyl)amino]-2-hydroxypropoxy]-3-trifluoromethyl-benzamide

Procedure:

1.3 ml (15.2 mmol) of epichlorohydrine was added to a solution of 1.6 ml (15.2 mmol) of tert-butylamine in 8 ml of ethanol during 10 minutes with stirring, keeping the temperature below 20° C., and allow to stand for 3 days.

Separately, 0.8 g (14.3 mmol) of potassium hydroxide was dissolved in a mixture of 20 ml of ethanol and 3 ml of water and into this solution 3.42 g (15.2 mmol) of N-hydroxy-3-(trifluoromethyl)-benzamide potassium salt and the formerly prepared solution of epichlorohydrine and tert-butylamine was added. The reaction mixture was stirred and boiled for 10 hours, then the solvent was evaporated. The residue was triturated with 20 ml of dichloromethane and 10 ml of water, the organic phase was separated, washed with 5 ml of water and 5 ml of saturated sodium chloride solution, dried over sodium

Example 66

Methyl-N-[2-hydroxy-3-(1-piperidinyl)propoxy]-3-pyridinecarboximidate (Z)-2-butenedioate (1:1)

Procedure:

11.4 g (38.2 mmol) of N-[2-hydroxy-3-(1-piperidinyl)propoxy]-3-pyridinecarboximidoyl chloride was dissolved in 60 ml of abs. methanol, then 25 ml (0.1 mole) of 25% methanolic solution of sodium methoxide was added dropwise during 5 minute. The reaction mixture was boiled for a half an hour and evaporated. The residue was stirred with 210 ml of dichloromethane for a half an hour, sodium chloride was filtered off, and the filtrate was washed with 50 ml of water, then with 50 ml of saturated sodium chloride solution, dried over magnesium sulfate and evaporated in reduced pressure. The crude product (9.8 g) was purified by chromatography to yield the title compound as a pale-yellow oil.

Yield: 2.9 g (29%)

Elementary analyses for $C_{15}H_{23}N_3O_3$

|     | calcd. | found |
| --- | ------ | ----- |
| C % | 61.4   | 61.2  |
| H % | 79.0   | 79.1  |
| N % | 14.3   | 14.5  |

Example 67

Diethyl-N-[2-hydroxy-3-(1-piperidinyl)-propoxy]-iminocarbonate

Procedure:

A mixture of 0.87 g (5 mmole) of 1-aminooxy-2-hydroxy-3-(1-piperidinyl)-propane and 1.1 g (5.5 mmole) of tetraethyl orthocarbonate was stirred at 100° C. for 3 hours in the presence of catalytic amount of p-toluenesulfonic acid. After evaporation the residue was purified by column chromatography (Merck Kieselgel 60; eluent: chloroform/methanol-cc. NH$_4$OH 30:5:0.2) to give the title compound as a pale-yellow oil.

Yield: 27.7% (oil)

$^{13}$C-NMR (d, CDCl$_3$): 154.9 (s, C=N), 76.5 (t, N—OCH$_2$), 66.6 (d, CHOH), 64.5 (t, CH$_3$CH$_2$), 64.1 (t, CH$_3$CH2), 61:5 (t, CHCH$_2$N), 54.8 (t, piperidine), 26.0 (t, piperidine), 24.2 (t, piperidine), 14.9 (q, CH$_3$), 14.1 (q, CH$_3$)

Example 68

N-[3-[(1,1-dimethylethyl)amino]-2-hydroxypropoxy]-O-ethyl-N'-phenyl-isourea

Procedure:

18.4 g (0.1 mole) of ethyl N-phenyl-chloroformimidate (F. Lengfeld and J. Stieglitz: Am. Chem. J. 16 70 (1894)) and 16.2 g (0.1 mole) of 1-aminooxy-2-hydroxy-3-[(1,1-dimethyl)amino]-propane [Ger. Off. 2 651 083] were dissolved in 200 ml of tetrahydrofurane, 13.9 ml (0.1 mole) of triethylamine was added and the mixture was stirred at room temperature for 10 hours. Triethylamine hydrochloride that formed was filtered, and the filtrate was evaporated in vacuum, the residue was dissolved in 200 ml of chloroform and washed with 50 ml of water. The organic layer was dried over sodium sulfate, filtered and evaporated under reduced pressure. The crude oily residue was purified by chromotography to give the title compound as a pale yellow oil.

Yield: 18.5 g (59.8%)

Elementary analysis for $C_{16}H_{27}N_3O_3$

|     | calcd. | found |
| --- | ------ | ----- |
| C % | 62.1   | 62.3  |
| H % | 8.8    | 8.5   |
| N % | 13.6   | 13.7  |

Example 69

N-[3-(1-piperidinyl)-propoxy]-O-phenyl isocarboxamide

Procedure:

3.16 g (20 mmole) of 1-aminooxy-3-(1-piperidinyl)-propane were dissolved in 50 ml of benzene, 2.4 g (20 mmole) of phenyl cyanate was added and the mixture was stirred at room temperature for 12 hours. Further 0.16 g (1.3 mmole) cyanate was added and the mixture was stirred further 12 hours. After evaporation the residue was dissolved in methanol and the solution was clarified by activated carbon and evaporated. The product was crystallized from ethyl acetate/ethyl alcohol to give white material.

Yield: 46.9%

Mp.: 63-70° C. (ethyl acetate)

$^{13}$C-NMR (d, D$_2$O): 152.4; 129.9; 125.8; 119.9; 70.3; 57.4; 54.3; 53.2; 23.0; 22.7; 21.0.

Example 70

N-[2-Hydroxy-3-(1-piperidinyl)propoxy]-N'-pentamethylene-O-ethyl-isourea

Procedure:

2.7 g (0.01 mole) of diethyl-N-[2-hydroxy-3-(1-piperidinyl)propoxy]-iminocarbonate (see in Example 67) and 0.99 ml (0.01 mole) of piperidine were dissolved in 40 ml of tetrahydrofurane and stirred at room temperature for 2 hours, then evaporated to dryness. The residue was purified by chromatography to yield the title compound as an oil.

Yield: 2.1 g (67.1%)

Elementary analysis for $C_{16}H_{31}N_3O_3$

|     | calcd. | found |
| --- | ------ | ----- |
| C % | 61.3   | 61.1  |
| H % | 10.0   | 9.8   |
| N % | 13.4   | 13.6  |

Example 71

N,N-dimethyl-N'-[2-hydroxy-3-(1-piperidinyl)-propoxy]-N''-phenyl-guanidine hydrochloride Procedure:

1150 mg (6.58 mmole) of 1-aminooxy-2-hydroxy-3-(1-piperidinyl)-propane (Ger. Off. 2 651 083) was dissolved in chloroform and 750 mg of $Na_2CO_3$ was added, then a solution of 1206 mg (6.58 mmole) of N,N-dimethyl-N'-phenyl-chloroformamidine (BR 888646/1959, Bayer, auth.: Kühle and Eue L.; CA 57, 136961/1962/) in 10 ml of chloroform was added dropwise. After 5 hours the solid state was filtered and the filtrate was evaporated. This residue (1800 mg oil) was dissolved in 10 ml of ethyl acetate, and the product was precipitated by addition of 10.46 ml of 0.54 N HCl/ethyl acetate. The yellow precipitate was filtered off, washed, and finally recrystallized from acetone, after ethyl acetate.

Yield: 28%
Mp.: 127 129° C.
IR (KBr): 3220, 2093, 2840, 2690, 2620, 1608, 1580, 1475, 1433, 1375, 1250, 1070, 1050, 1000, 925, 900, 760, 705 $cm^{-1}$

Example 72

N-[3-[1,1-dimethylethyl)amino]-2-hydroxypropoxy]-N'-phenyl-guanidine

Procedure:

3.1 g (0.01 mole) of N-[3-[(1,1-dimethylethyl)amino]-2-hydroxypropoxy]-O-ethyl-N'-phenyl-isourea (see in Example 68) was dissolved in 20 ml of tetrahydrofuran and 200 ml of 25.% of ammonium-hydroxide solution and 0.26 g (5 mmol) of ammonium chloride were added and the mixture was kept at room temperature for 15 hours. The mixture was evaporated to dryness and purified by chromatography to yield the title compound as an oil.

Yield: 1.7 g (60.7%)
Elementary analysis for $C_{14}H_{24}N_4O_2$

|     | calcd. | found |
|-----|--------|-------|
| C % | 60.0   | 60.2  |
| H % | 8.6    | 8.9   |
| N % | 20.0   | 19.8  |

Example 73

N,N'-diphenyl-N-[2-hydroxy-3-(1-piperidinyl)-propoxy-benzenecarboxamidine hydrochloride Procedure:

3.55 g (20 mmol) of 3-piperidino-2-hydroxy-1-propane was dissolved in 2.5 ml of water, 0.8 g (20 mmol) of NaOH was added, and the mixture was stirred at room temperature for 1 hour. Then a solution of 6.49 g (20 mmol) of N,N'-diphenyl-N-hydroxy-benzenecarboxamidine hydrochloride in 60 ml of ethyl alcohol was added dropwise, and further 0.8 g (20 mmole) NaOH. The obtained yellow suspension was boiled for 2 hours. Then the precipitated sodium chloride was filtered off, washed with ethyl alcohol. Solvent was evaporated and 40 ml of ethyl acetate was added and two times was extracted with 40 ml portions of distilled water. The organic phase was dried over sodium sulfate, filtered. The product was precipitated by addition of 5.5 ml of 3.67 N HCl/ethyl acetate. The precipitate was filtered off, washed, and finally recrystallized from methanol/ether.

Yield: 42%
Mp.: 151-155° C. (methanol/ether)
$^{13}$C-NMR (d, $CDCl_3$): 159.6, 148.0, 140.9, 131.0, 129.7, 129.3, 128.9, 128.5, 127.9, 127.5, 64.2, 60.2, 54.5, 22.7, 21.9.

Example 74

N-[3-(1-piperidinyl-propoxy]-N-methyl-N'-phenyl-O-ethyl-isocarboxamide

Procedure for the preparation of this compound is the same as written in the Example 68, using 1-methylaminooxy-2-hydroxy-3-(1-piperidinyl)-propane and ethyl-N-phenyl-chloroformimidate as starting materials.

Yield: 56% (oil)
Elementary analysis for $C_{17}H_{29}N_3O_3$

|     | calcd. | found |
|-----|--------|-------|
| C % | 66.4   | 66.2  |
| H % | 9.5    | 8.9   |
| N % | 13.7   | 13.9  |

Example 75

N-[2-hydroxy-3-(1-piperidinyl)propoxy]-N-methyl-N'-phenyl-guanidine

Procedure for the preparation of this compound is the same as written in the Example 72, using N-[2-hydroxy-3-(1-piperidinyl)propoxy]-N-methyl-N'-phenyl-O-ethyl-isourea (see Example 74.) as starting materials.

Yield: 43% (oil)
Elementary analysis for $C_{16}H_{26}N_4O_2$

|     | calcd. | found |
|-----|--------|-------|
| C % | 62.7   | 62.2  |
| H % | 8.5    | 8.8   |
| N % | 18.3   | 18.4  |

Example 76

N,N,N'-trimethyl-N'-[3-(1-piperidinyl)-propoxy]N''-phenyl-guanidine

Procedure:

344 mg (2.0 mmole) 1-methylaminooxy-2-hydroxy-3-(1-piperidinyl)-propane was dissolved in chloroform and 220 mg of $Na_2CO_3$ was added, then a solution of 438 mg (2.0 mmole) of N,N-dimethyl-N'-phenyl-chloroformamidine hydrochloride in 3 ml of chloroform was added dropwise. After 8 hours the solid state was filtered and the filtrate was evaporated. This residue was dissolved in ethyl acetate and the product was extracted by addition of HCl solution (pH=1) to water. The aqueous phase was made alkaline then by addition of 2N NaOH solution to pH=11, and extracted with ethyl acetate. The organic phase was evaporated, and the further purification was made by column chromatography to give the title compound as a yellow oil.

Yield: 10% (oil)

$^{13}$C-NMR (d, CDCl$_3$): 156.6, 150.5, 128.4, 120.5, 70.0, 55.9, 54.4, 40.6, 39.4, 25.8, 25.6, 24.3.

Example 77

/R/(+)-N-[2-hydroxyl-3-(1-piperidinyl)propoxy]-3-pyridinecarboximidoyl chloride (Z)-2-butenedioate (1:1)

Procedure:

2.16 g (3.26 mmole) of (S)—N-[2-[2-(R)-(1,1-dimethyl-ethyloxycarbonylamino)-3-phenylpropionyloxy]-3-(1-piperidinyl)propoxy]-3-pyridinecarboximidoyl chloride (Z)-2-butenedioate (1:1) (see Example 18) was suspended in 40 ml of methanol and boiled for 1 hour, then evaporated to dryness. The residue was triturated with 20 ml of ethyl acetate, the precipitate was filtered, washed with ethyl acetate. This crude product was recrystallized in isopropyl alcohol to yield the title compound.

Yield: 1.16 g (85%)

Mp.: 136-137° C.

[∀}$_D$: +5.6° (c=1, MeOH, t=27° C.)

Example 78

N-(3-piperidino-1-propoxy)-3-pyridinecarboximidoyl chloride dihydrochloride

After cooling to 0° C. a mixture of 10 ml of distilled water and 4.36 ml of concentrated hydrochloric acid, 2 g (7.62 mmoles) of N-(3-piperidino-1-propoxy)-3-pyridinecarboxamidine (see Example 31) are added under stirring. To the yellow solution 2.7 g (3.81 mmoles) of sodium nitrite dissolved in 10 ml of water are added dropwise at −5° C. during 30 minutes. After stirring the greenish solution at −5° C. for 1.5 hours, the pH of the solution is adjusted to 10 by adding 1 N aqueous sodium hydroxide solution under cooling, then the solution is extracted 3 times with 40 ml of chloroform. The organic phase is washed with 20 ml of water, dried over sodium sulfate and evaporated. The residue is purified by column chromatography (Merck Kieselgel 60; eluent: chloroform/methanol 1:1) to obtain 1.7 g (79.2%) of the base corresponding to the title compound.

The title hydrochloride is prepared from the base obtained by adding an ethanolic solution of hydrogen chloride, m.p.: 165-167° C.

IR (KBr): 3015, 2945, 2515, 2088, 1982, 1600, 1570, 1437, 1402, 1200, 1060, 988, 912, 808 cm$^{-1}$.

The above starting material can be prepared as follows:

After dissolving 2.86 g (51.06 mmoles) of potassium hydroxide in 20 ml of abs. ethanol, 6.45 g (47.0 mmoles) of 3-pyridinecarboxamide oxide are portionwise added while stirring. After dissolution, 7.7 g (47.66 mmoles) of 1-(3-chloropropyl) piperidine dissolved in 5 ml of ethanol are dropwise added. After 9-hour reaction, the precipitated potassium chloride is filtered off, the ethanolic solution is clarified by activated carbon and evaporated. After taking up in 100 ml of chloroform, the evaporation residue is washed 3 times with 100 ml of 1 N sodium hydroxide solution each, then with 50 ml of water. After separation, the organic phase is dried over sodium sulfate, filtered and evaporated. The oily residue becomes crystalline on cooling. The crystals are triturated with about 20 ml of ether, filtered and dried to give a beige product in a yield of 4.8 g (38.9%).

IR (KBr): 3422, 3107, 2937, 2870, 2819, 1640, 1479, 1391, 1309, 1194, 1123, 1059, 1042, 982, 916 cm$^{-1}$.

Following the process described in the previous example the following compound was prepared:

Example 79

O-(3-piperidinopropyl)-3-nitro-benzhydroximyl chloride hydrochloride

Yield: 50%

Mp.: 173-175° C.

IR (KBr): 3420, 2926, 2953, 2649, 2546, 1514, 1591, 1533, 1452, 1354, 1259, 1252, 1049, 994, 733 cm$^{-1}$.

FORMULATION EXAMPLES

Example 1

Tablet

Tablet containing 50 mg active material is prepared from the following components:

N-[2-hydroxy-3-(1-piperidinyl)-propoxy}-2-thiophene-carboximidoyl

| chloride monochloride | 50.0 mg |
|---|---|
| corn starch | 100.0 mg |
| lactose | 95.0 mg |
| talc | 4.5 mg |
| magnesium stearate | 0.5 mg |

The active compound is finely ground, mixed with the additives, the mixture is homogenized and granulated. The granulates are pressed into tablets.

Example 2

Tablet

Tablet containing 5 mg active material is prepared from the following components:

N-[2-hydroxy-3-(1-piperidinyl)-propoxy]-2-nitro-benzimidoyl

| chloride monochloride | 50.0 mg |
|---|---|
| corn starch | 75.0 mg |
| lactose | 7.5 mg |
| colloidal silica | 7.5 mg |
| magnesium stearate | 5.0 mg |

The composition is prepared from the above components in accordance with example 1.

Example 3

Tablet

Tablet containing 5 mg active material is prepared from the following components:

N-[2-benzyloxy-3-(1-piperidinyl)-propoxy]-3-pyridine-carboximidamide-

| | |
|---|---|
| (Z)-2-butenedioate (1:1) | 5.0 mg |
| corn starch | 75.0 mg |
| gelatin | 7.5 mg |
| microcrystalline cellulose (Apical) | 25.05 mg |
| magnesium stearate | 2.5 mg |

The composition is prepared from the above components in accordance with example 1.

Example 4

Capsule

Capsule containing 10 mg active material is prepared from the following components:

N-[2-palmitoloxy-3-(piperidinyl)-propoxy]-3-pyridine-

| | |
|---|---|
| carboximidamide monohydrochloride | 10 mg |
| lactose | 80 mg |
| corn starch | 25 mg |
| talc | 3 mg |
| colloidal silica | 3 mg |
| magnesium stearate | 2 mg |

The active material is mixed with the additives, the mixture is homogenized and filled into gelatine capsules.

Example 5

Capsule

Capsule containing 20 mg active material is prepared from the following components:

N-{2-hydroxy-3-(piperidinyl)-propoxy]-2-thiophene-

| | |
|---|---|
| carboximidoyl chloride monohydrochloride | 20 mg |
| microcrystalline cellulose (Apical) | 99 mg |
| amorphous silica | 1 mg |

The active material is mixed with the additives, the mixture is homogenized and filled into gelatine capsules.

Example 6

Dragée

Dragée containing 25 mg active material is prepared from the following components:

N-{3-[(1,1-dimethyl-ethyl)-amino]-2-hydroxy-propoxy}-3-

| | |
|---|---|
| trifluoromethyl-benzamidine hydrochloride | 25 mg |
| carboxymethyl cellulose | 295 mg |
| stearic acid | 20 mg |
| cellulose acetate phtalate | 40 mg |

The active material is mixed with the carboxymethyl cellulose and stearic acid, and the mixture is granulated in the solution of cellulose acetate phtalate in 200 ml ethanol-ethyl acetate. A core is pressed from the granulate which is covered by aqueous polyvinylpirrolidone solution containing 5% sugar.

Example 7

Injection

Injection solution is prepared from the following components:

N-[2-hydroxy-3-piperidinyl)-propoxy]-2-nitro-

| | |
|---|---|
| benzimidoyl chloride | 5.0 g |
| sterile physiological saline solution | 2.0 ml |

Example 8

Ointment

Ointment is prepared from the following components:

N-[2-hydroxy-3-(1-piperidinyl)-propoxy]-2-thiophene-

| | |
|---|---|
| carboximidoyl chloride monohydrochloride | 7.5 g |
| stearic acid | 18.0 g |
| cetyl stearyl alcohol | 15.0 g |
| glycerin monostearate | 4.0 g |
| sodium lauryl sulfate | 1.5 g |
| methyl p-hydroxy benzoate | 0.2 g |
| distilled water | 150 ml |

The stearic acid, cetyl stearyl alcohol and glycerine monostearate are melted together. The sodium lauryl sulfate and methyl-p-hydroxy benzoate are dissolved in 100 ml water under slight warming and then added to the lipophylic components while stirring until the temperature decreases to room temperature. Subsequently, the solution of active compound in 50 water is added and thoroughly mixed.

Example 9

Ointment

Ointment is prepared from the following components:

N-[2-hydroxy-3-piperidinyl-propoxy]-2-nitro-

| benzimidoyl chloride monohydrochloride | 7.0 g |
| polysorbate | 4.0 g |
| liquid paraffin | 4.0 g |
| cetyl stearyl alcohol | 12.0 g |
| white vaseline | 20.0 g |
| glycerin monostearate | 4.0 g |
| methyl p-hydroxy benzoate | 0.2 g |
| ethyl alcohol | 1.8 g |
| distilled water | 150 ml |

The composition is prepared as described in Example 8.

Example 10

Cream

Cream is prepared from the following components:

N-[2-hydroxy-3-piperidinyl-propoxy]-4-pyridine-carboximidoyl

| chloride (Z)-2-butenedioate (1:) | 10.0 g |
| white vaseline | 90.0 g |
| white wax | 3.0 g |
| cetyl stearyl alcohol | 3.0 g |
| sodium tetraborate | 4.0 g |
| methyl p-hydroxy benzoate | 0.2 g |
| distilled water | 90 ml |

The solution of the water-soluble components is added to the warm mixture of the lipophylic components as in Example 8, and the aqueous solution of the active compound is added to the final emulsion.

Effect of N-[2-hydroxy-3-(1-piperidinyl)propoxy]-3-pyridinecarboximidoyl chloride maleate on cellular expression of HSP (examined on translational level)

1. Background

Experiments set forth in this section were conducted to determine whether N-[2-hydroxy-3-(1-piperidinyl)propoxy]-3-pyridinecarboximidoyl chloride maleate acts to increase the expression of molecular chaperon by a cell. The accumulation of different heat shock proteins subsequent to a period of exposure to heat shock alone, and to heat shock in combination with N-[2-hydroxy-3-(1-piperidinyl)propoxy]-3-pyridinecarboximidoyl chloride maleate administration, was examined by adding $10^{-5}$ M of N-[2-hydroxy-3-(1-piperidinyl)propoxy]-3-pyridinecarboximidoyl chloride maleate before, during, or immediately after hyperthermic treatment of heart myogenic cells (H9c2 cells).

2. Materials & Methods 2.1 Cell Culture Conditions:

The embryonic rat heart-derived cell line H9c2 was obtained from European Collection of Animal cell Cultures (ECACC) (88092904). The cells were maintained at 37° C. in Dulbecco's modified Eagle's medium (DMEM) supplemented with 10% fetal calf serum (GIBCO) in JOUAN C02 thermostat (5% $CO_2$).

2.2 N-[2-hydroxy-3-(1-piperidinyl)propoxy]-3-pyridinecarboximidoyl Chloride Maleate Treatment and Heat Shock Conditions:

Heat shock was performed at 43° C. in $CO_2$ thermostat for the given time intervals (20, 40, 60, 90 and 120 min.). Cells were then taken back to 37° C. for 6 hours and proteins were extracted for SDS-PAGE. When N-[2-hydroxy-3-(1-piperidinyl)propoxy ]-3-pyridinecarboximidoyl chloride maleate was added before heat shock. $10^{-5}$ M N-[2-hydroxy-3-(1-piperidinyl)propoxy]-3-pyridinecarboximidoyl chloride maleate was administered for 16 hours before the stress. In other set of experiments, N-[2-hydroxy-3-(1-piperidinyl)propoxy]-3-pyridinecarboximidoyl chloride maleate was added in $10^{-5}$ M concentration right after heat stress, during the 6 hours recovery period. The experiments were repeated three times.

2.3 Western Blot

For SDS-PAGE, cells were grown in 6 cm Petri dishes. The amount of the cells at the start of the experiment was $8 \times 10^5$ and were still suconfluent when proteins were extracted. After the 6 hours recovery cells were washed two times in PBS then scrapped from the surface of the dishes in PBS. Then cells were spun for 5 min. at 1500 rpm and taken up in 100: modified solubilizing buffer (*Molecular Cloning, A Laboratory Manual*, Ed. Sambrook. Fritsche. Maniatis, Bold Spring Harbor Laboratory Press (1989)) containing 50 mM Tris-HCl, pH8.0; 5 mM EDTA; 150 mM NaCl; 15 Tritox N-100; 1 PMSF; 2 :g/ml aprotinin; 1 :g/ml chymostatin; 1 :g/ml pepstatin; and sonicated for 3×2o sec (2 min. intervals, setting 8).

Protein concentration was determined from 5:1 samples by the Bradford assay (M. M. Braford, *Anal. Biochem.*, 72: 248-254 (1976)) in three parallel. Samples were adjusted to 100 :g/30:1 with the above buffer and the next buffer so that the concentration of the buffer in the sample will be: 110 mM Tris-HCl pH 6.8, 8.3 mM mercaptoethanol, 3% SDS, 3% glycerol and some bromophenol blue and shaken at room temperature for 30 min.

Electrophoresis was carried out according to Laemmli (U. K. Laemmli, *Nature*, 227:680-685 (1970)) on two 8-18% polyacrylamide gel at constant voltage 50 V for overnight. Proteins were either stained with Coomassie Brilliant Blue R-250 or transferred to Immobilone PVDF membrane (Millipore) at constant current (300 mA) for 3 hours at 4° C. in transfer buffer (10 mM CAPS, pH 11, 10% methanol) (*Protein Blotting Protocols for the Immobilon-P Transfer Membrane*, 3. Laboratory Manual, Millipore). After transfer, non-specific sites of the membrane were blocked with 2% BSA in TPBS (phosphate buffered saline with 0.1% Tween 82) for overnight at 4° ° C. The blot was incubated with GRP94 monoclonal antibody (SPA-850, StressGen) diluted 1:3000, with HSP60 monoclonal antibody (SPA-600, StressGen) with 1:2700 dilution, with HSP72 monoclonal antibody (C92F34-5, StressGen) diluted 1:1250 or with HSP90 monoclonal antibody (AC88, StressGen) diluted 1:2000, for 1 hour at room temperature. Then it was washed with TPBS buffer for one hour and incubated with horseradish peroxidase conjugated anti-rat (Sigma, 1:4000 dilution, for GRP-94) or anti-mouse (Sigma, absorbed with human and rat serum proteins, 1:3000 dilution, for Hsp60, HSP72 or HSP90) secondary antibody for 1 hour respectively. After successive washing with TPBS the membrane was developed with ECL system (Amersham).

A total-protein dilution series was blotted and developed parallel with the samples every time, and a calibration curve was calculated. The changes in the stress protein content was quantified using a Bio-Rad densitometer (Model 1650) and a Hewlett-Packard Integrator (HP 3394A) and corrected according to the calibration curve. When making the calculations the densitometric data of the given protein band at 37° C. without N-2-hydroxy-3-(1-piperidinyl)propoxy]-3-(pyridinecarboximidoyl chloride maleate treatment was considered as 100% and all the other intensities were compared to that sample.

2.4 Statistical Analysis

Data are reported as means±SE. Statistical comparison and calculation was performed by one-way analysis of variance with Posthoc Newman-Keuls test (Pharmacological Calculation System). Statistical significance was defined as $P<0.05$.

3. Results

Hsp60: N-[2-hydroxy-3-(1-piperidinyl)propoxy]-3-pyridinecarboximidoyl chloride maleate treatment accomplished at 37° C. has no measurable effect on the level of this hsp. Heat shock at 43° C. alone, lasting for 20 min. can increase the amount of hsp60 almost by twofold. By extending the duration of heat treatment, no further elevation could be observed in the level of this protein. When N-[2-hydroxy-3-(1-piperidinyl)propoxy]-3-pyridinecarboximidoyl chloride maleate was added at a concentration of $10^{-5}$ M 16 hours before heat stress, the amount of hsp60 increased by about fivefold (compared to 37° C. control) even if samples exposed to 20 min. heat treatment. This effect of N-[2-hydroxy-3-(1-piperidinyl)propoxy]-3-pyridinecarboximidoyl chloride maleate on the level of hsp60 was evident also in samples heat treated for 40 and 60 min., respectively, however started to decline thereafter. N-[2-hydroxy-3-(1-piperidinyl)propoxy]-3-pyridinecarboximidoyl chloride maleate added during the recovery phase was also effective though to a significantly lesser extent then observed by adding this compound before the stress.

Hsp72: The amount of resting hsp72 was rather low in H9c2 cells, the effect of different treatments on hsp70 level, however, was dramatic. There was already a significant increase at 20 min. heat shock, and at 40 min. heat treatment the amount was almost 10 times higher than that of detected in control cells. Heat treatment at longer duration resulted in no significant change compared to 40 min. samples. Administration of N-[2-hydroxy-3-(1-piperidinyl)propoxy]-3-pyridinecarboximidoyl chloride maleate before heat stress had a very profound effect. At 60 min. heat stress the hsp72 level increased by about 50 times when comparing to 37° C. samples, but a significant increase could be detected already at heat stress lasting for 40 min. These highly induced amounts of hsp72 were stable in cells heat shocked for 120 min. N-[2-hydroxy-3-(1-piperidinyl)propoxy]-3-pyridinecarboximidoyl chloride maleate added during the recovery phase was also effective though to a lesser degree.

Hsp90: At 20 min. heat treatment, high temperature shock alone was unable to induce elevated level of HSP90, however, if N-[2-hydroxy-3-(1-piperidinyl)propoxy]-3-pyridinecarboximidoyl chloride maleate added before the heat stress, the level of Hsp90 increased by about fivefold. The highest effect of the drug preincubation could be observed following its combination with 60 min. heat treatment. It was interesting to note, that in the case of HSP90 N-[2-hydroxy-3-(1-piperidinyl)propoxy]-3-pyridinecarboximidoyl chloride maleate added following 43° C. 60 min. treatment was as effective (if not more) as if added before high temperature stress. Obviously, incubation at high temperature longer than 90 min. the effect of N-[2-hydroxy-3-(1-piperidinyl)propoxy]-3-pyridinecarboximidoyl chloride maleate is fading.

Grp94: The formation of the stress protein Grp94 was induced following a 20 min. heat shock. This effect peaked at thermal treatment for 60 min. whereas a sharp decline has already been detected in case of 90 min. samples. The capability of N-[2-hydroxy-3-(1-piperidinyl)propoxy]3-prydinecaboxymidoyl chloride maleate to induce the level of Grp94 was the most pronounced in case if the compound was added before the stress but significant raise could be seen if the preaddition of the drug was combined with a 20 min. long heat shock (where there was a 4 times increase compared to 43° C. treatment). On the other hand, addition of the compound during recovery from heat stress lasting for 40 to 60 min. was almost effective as the administration of N-[2-hydroxy-3-(1-piperidinyl)propoxy]-3-pyridinecarboximidoyl chloride maleate for 16 hours long before the stress.

Figure 2:
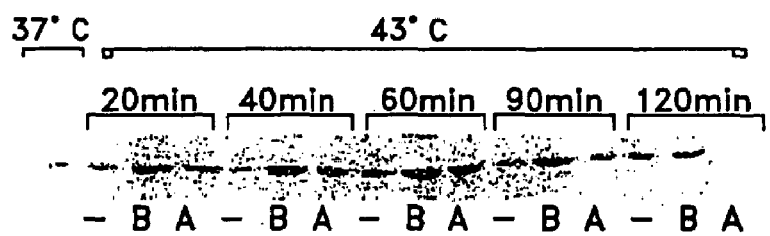
FIG. 2 shows the results of the above experiment obtained by Western blot analysis based on densitometric evaluation.
Figure 2:
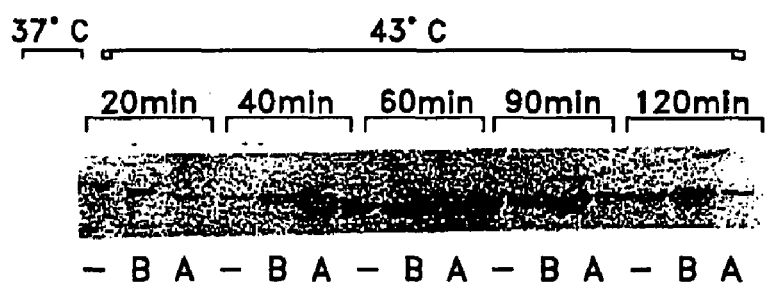
Figure 2:
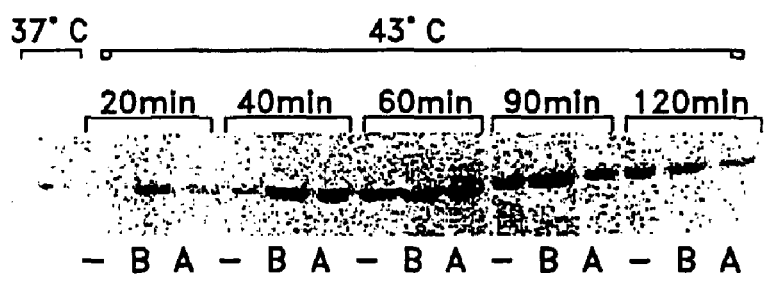
Figure 2:
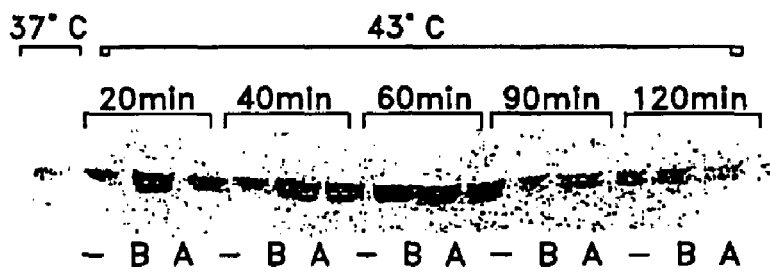

FIG. 2 shows the Western blot analysis of proteins from H9c2 cells. Probes used are: hsp60 antibody, shown in (1); hsp72 antibody shown in (2); hsp90 antibody, shown in (3) and grp94 antibody, shown in (4). Lane (−) represents cells kept in the absence of N-[2-hydroxy-3-(1-piperidinyl)propoxy]-3-pyridinecarboximidoyl chloride maleate at 37° C.; and lane (+) represents cells kept in its presence (concentration of $10^{-5}$ M for 16 hours). Heat shock at 43° C. was performed for the times indicated on the figure. N-[2-hydroxy-3-(1-piperidinyl)propoxy]-3-pyridinecarboximidoyl chloride maleate at $10^{-5}$ M was added 16 hours before the heat treatment (lane (B)) or during the recovery period (lane (A)).

An overview of the effect of the various treatments on the amount of different hsp in H9c2 heart cells is provided in FIG. 1. The amount of stress proteins in cells exposed to heat stress (43° C.) alone is represented by (A); the amount of stress proteins in cells treated with $10^{-5}$ M N-[2-hydroxy-3-(1-piperidinyl)propoxy]-3-pyridinecarboximidoyl maleate before the heat treatment is represented by (B); and the amount of stress proteins in cells treated with $10^{-5}$ M N-[2-hydroxy-3-(1-piperidinyl)propoxy]-3-pyridinecarboximidoyl chloride maleate during the six hour recovery period is represented by C. The horizontal axis represents the time duration of the heat treatment and the vertical axis represents the relative amount of stress proteins.

Heat treatment alone induced all kinds of HSPs investigated in this study. The increase was the less pronounced in the case of hsp60. The level of hsp60 elevated up to about twofold after exposure of cells to 20 min. heat, whereas no further increase could be detected at longer heat treatments. The largest effect of heat stress could be seen for hsp72, as its amount increased to about 12 times. When N-[2-hydroxy-3-(1-piperidinyl)propoxy]-3-pyridinecarboximidoyl chloride maleate was added 16 hours before the heat treatment the level of all HSPs increased further up to at least twofold as compared to that observed upon heat stress. It was also clear that the level of hsp72 increased in a much higher extent amongst HSPs by combining heat stress and N-[2-hydroxy-3-(1-piperidinyl)propoxy]-3-pyridinecarboximidoyl chloride maleate if compared again to the induction detected for heat stress alone. When N-[2-hydroxy-3-(1-piperidinyl)propoxy]-3-pyridinecarboximidoyl chloride maleate was administered during the recovery phase almost in all cases examined, content of hsp(s) increased, but again elevation of hsp72 was the most pronounced.

4. Discussion

Western blot analysis revealed a remarkable accumulation of different classes of HSPs examined after the exposure of heart cells to heat shock. Addition of N-[2-hydroxy-3-(1-piperidinyl)propoxy]-3-pyridinecarboximidoyl chloride maleate either before or after high temperature stress multiplied the effect of heat treatment upon the production of HSPs. Accordingly, N-[2-hydroxy-3-(1-piperidinyl)propoxy]-3-pyridinecarboximidoyl chloride maleate acts in synergy with temperature stress by inducing the formation of all classes of molecular chaperones.

Effect of N-[2-hydroxy-3-(1-piperidinyl)-propoxy]-3-pyridinecarboximidoyl Chloride Maleate on Cellular Expression of HSP (Examined on Transcriptional Level)

1. Background

Brief exposure to ischemia (e.g., by repeated stunning) can precondition the heart and protect it from subsequent lethal ischemia, as evidenced by decreased incidence of ventricular fibrillation, reduced infarct size and better recovery of regional myocardial function during the reperfusion of ischemic heart. Such precondition has been demonstrated to induce the expression of HSPs, especially hsp72. In this section, the effect of N-[2-hydroxy-3-(1-piperidinyl)propoxy]-3-pyridinecarboximidoyl chloride maleate on the expression of hsp72 is investigated by examining the mRNA accumulation in a cell following ischemia and comparing it to the situation where ischemia is combined with administration of N-[2-hydroxy-3-(1-piperidinyl)propoxy]-3-pyridinecarboximidoyl chloride maleate.

2. Materials & Methods 2.1 Induction of Heat Stress

Experiments were carried out in SPRD male rats. Animals were anaesthetized with Nembutal in a dose of 60 mg/kg/i.p. Body temperature of the rats were maintained with an infra lamp placed over the abdomen and the rectal temperature was measured. After a 25-40 minute period the temperature of the rats increased to 42.0-42.2° C. and this temperature was maintained for 15 minutes. After a recovery period (2 hrs), tissue samples were collected from the left and right ventricles.

2.2 Induction of Cardiac Ischemia

Experiments were carried out in SPRD male rats. The animals were anaesthetized with Nembutal in a dose of 60 mg/kg/i.p. After opening the chest and pericardium, the LAD coronary artery was occluded for 5 minutes and then the incidence and duration of ventricular tachycardia and fibrillation in the reperfusion period (10 minutes) were investigated. Tissue samples were collected from the left and right ventricles.

2.3 Northern Blot Method

Total RNA was extracted using RN Agents kit (Promega) according to the manufacturer's instructions (Protocols and Applications Guide, 2nd edition, 1991, Promega Corporation). Briefly, the frozen tissue samples (the tissue samples from the left and right ventricles of rats subjected to heat stress or cardiac ischemia). The tissue samples weighing 50 to 100 mg were homogenized in 1.0 ml denaturing solution at +4° C. by Brinkman homogenization. Then $\frac{1}{10}$ vol. 3M sodium acetate (pH 4.0) was added and the homogenate were extracted with acidic phenol (phenol:chloroform:isoamylalcohol 25:24:1) for 10 seconds by vortex. The sample was incubated on ice for 15 minutes, and then centrifuged (4 C; 20 min, 10,000×g). The aqueous phase was transferred to a new Eppendorf-tube, the process was repeated and the aqueous was precipitated at −20° C. overnight. Following centrifugation (4° C.; 20 min. 10,000×g) the precipitate was washed twice with 95% ethanol and dried at room temperature. The RNA was suspended in 20:1 DEPC-treated water. Eight:1 g of total RNA was run on formaldehyde-agarose gel by capillary transfer, the RNA on the gel was blotted onto nylon membrane according to the manufacture's instructions (Zeta-Probe GT, BioRad).

The hsp72 mRNA content of individual samples was compared with the mRNA level of the glyceraldehyde-3-phosphate dehydrogenase (GAPDH) gene level of the corresponding probes. DNA probes (full length human hsp70 cDNA and Apa-NcoI fragment of the rat GAPDH cDNA) was labeled with alpha-$^{32}$P CTP using Random Primed DNA Labeling Kit (USB). Radiolabeled DNA fragments were purified on Sephadex G-50 (Pharmacia) column as described (Ausubel et al. (eds)): Current Protocols in Molecular Biology: JOHN WILEY & SONS: 1987).

Prehybridizations were carried out at 65° C. in H-buffer (0.25M $Na_2HPO_4$, pH 7.2, 7% SDS) for 15 minutes. Hybridizations were carried out overnight (65 C; H-buffer) with isotope labeled probe concentration of at least $10^6$ cpm/ml. The membrane was washed with 20 mM $Na_2HPO_4$, pH 7.2, 5% SDS (65 C; 2×15 min.) and evaluated by autoradiography. The same membrane was used for the hsp70 probe as well as for the measurement of GAPDH and mRNA used as internal standard.

3. Results

Coronary occlusion for 5 minutes was followed by reperfusion which provoked ventricular tachycardia and fibrillation in the rats. N-[2-hydroxy-3-(1-piperidinyl)propoxy]-3-pyridinecarboximidoyl chloride maleate pretreatment (0.5-, 0.75-, 1.0 mg/kg of body weight i.v. 5 min. before the occlusion) reduced significantly the mean duration of ventricular tachycardia and improved the survival rate by preventing ventricular fibrillation.

Whereas all animals (n=6) from the control group died during the phase of reperfusion, the N-[2-hydroxy-3-(1-piperidinyl)propoxy]-3-pyridinecarboximidoyl chloride maleate treated (100 mg/kg p.o.) ones not only survived the reperfusion after the 5 min. occlusion, but a highly increased expression of hsp72 gene was detected in their heart muscle preparations.

Figure 3:
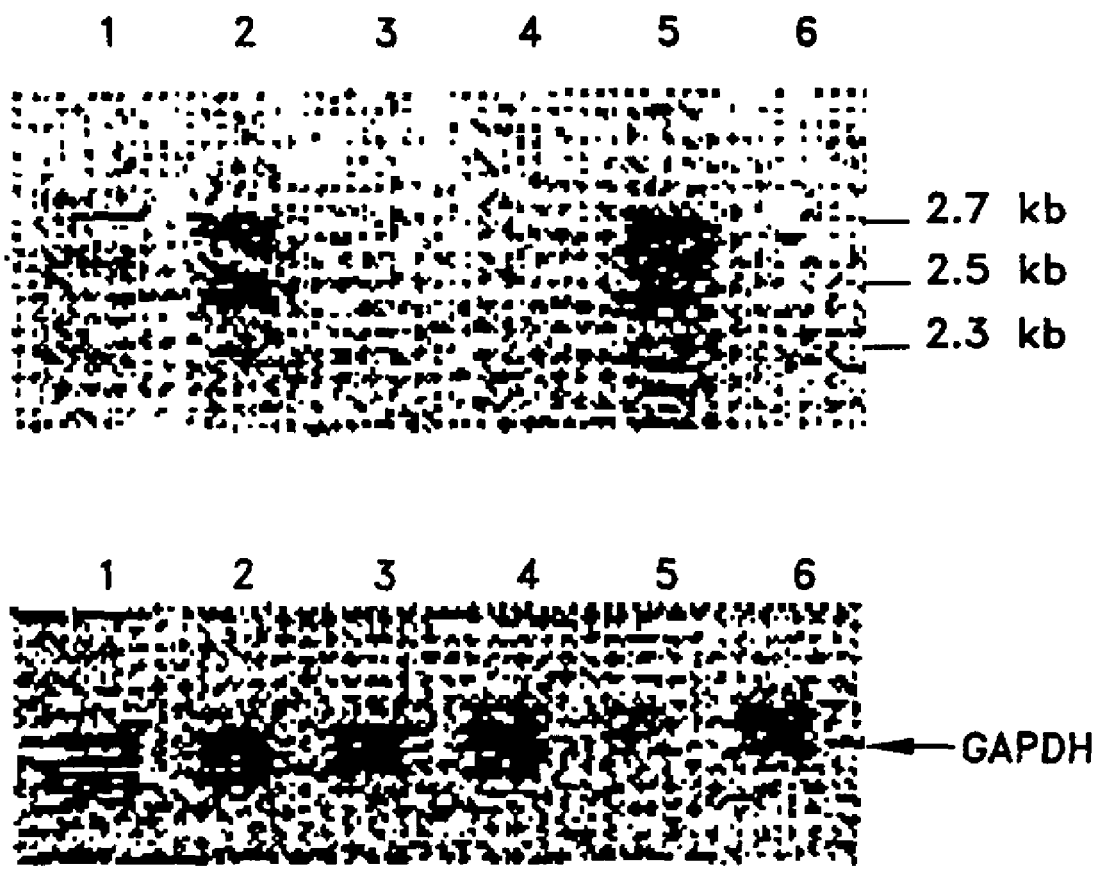
FIG. 3 shows the results of hsp70 mRNA Northern blot analysis obtained during examination of the effect of compound B on cellular hsp expression at transcription level.

FIG. 3 is the Northern blot analysis of total RNA isolated from left ventricles of rat heart, illustrating the results obtained from the experiment. Control (lane 1); heat treated (lane 2); sham operated (lane 3); ischemia (lane 4); N-[2-hydroxy-3-(1-piperidinyl)propoxy]-3-pyridinecarboximidoyl chloride maleate plus ischemia (lane 5); and N-[2-hydroxy-3-(1-piperidinyl)propoxy]-3-pyridinecarboximidoyl chloride maleate (lane 6). GADPH was measured as an internal probe. For heat shock, the rectal temperature was maintained at 42° C. for 15 minutes.

It is noted that in the absence of stress, administration of N-[2-hydroxy-3-(1-piperidinyl)propoxy]-3-pyridinecarboximidoyl chloride maleate alone was unable to activate the hsp72 gene.

Protective Effect of Hydroxylamine Derivatives of the Invention Against Cardiac Ischaemia Male Sprague-Dawley rats (380-450 g b.w.) were anaesthetized with sodiumpentobarbital (Nembutal 60 mg/kg body weight, i.p.) and artificially ventilated with room air (2 ml/100 g; 54 stroke/minutes) via tracheotomy. The right carotid artery was catheterized and connected to a pressure transducer (BPR-01, Stoelting) for the measurement of systemic arterial blood pressure (BP) by means of a preamplifier (Hg-02, Experimetria). Hydroxylamine derivatives disclosed in Example 5 were administered via the venous cannule to jugular vein (i.v.) and orally (p.o.). Heart rate (HR) was measured by a cardiotachometer (HR-01, Experimetria). The electrocardiogram (ECG standard lead II) was recorded on a devices recorder (MR-12, Medicor) by means of subcutaneous steel needles electrodes. The chest was opened by a left thoracotomy and the heart was exteriorized by a gentle pressure on the right side of the rib cage. A 4-0 silk suture was quickly placed under the main left coronary artery as described by Selye et al. (1960). The heart was carefully replaced in the chest and the animal left to recover. Rectal temperature was monitored and kept constant at 37 C. The experimental protocol was initiated with a 15 minute stabilization period during which the observation of a sustained blood pressure less than 70 mmHg and or the occurrence of anhythmia led to exclusion. Myocardial ischemia was induced with coronary occlusion for 5 minutes and reperfusion allowed for 10 minutes.

During the entire experiment BP, HR and ECG were continuously registered on a multiscriptor (R61-6CH, Medicor). Hydroxylamine derivatives, the tautomeric forms of which are represented by structures (I) and (II), were administered 5 to 60 minutes before the occlusion after i.v. and p.o. treatment, respectively. The doses of the hydroxylamine derivatives of Example 5 were 0.5; 0.75; 1.0 mg/kg i.v. and 100 mg/kg of body weight p.o., while the reference substance Bepridil was given in a dose of 1.0 mg/kg i.v.

The mean duration of ventricular tachycardia (VT) and/or ventricular fibrillation (VF) during the first 3 minutes of reperfusion was analyzed by one-way analysis of variance. The incidence of VF was analyzed using a chi-square test. The haemodynamic variables were analyzed using a chi-square test. The haemodynamic variables were analyzed using Student's "t"-test. The critical level of significance was set at $p<0.05$. All results were expressed as a means±S.E.M. Drugs were administered i.v. in a dose of 1 mg/kgbw 5 min. before the occlusion.

The hydroxylamine derivatives that are found to be particularly advantageous for protecting an animal against ischemic/reperfusion injury are listed below. Survival (%) indicates the percent of animals survived the effects of 5 minutes coronary occlusion.

| Code | Survival (%) |
|---|---|
| Example 77 i.v. 1 mg/kgbw | 67 |
| Example 78 i.v. 1 mg/kgbw | 100 |
| Example 8 i.v. 1 mg/kgbw | 100 |
| Example 13 i.v. 1 mg/kgbw | 60 |

-continued

| Code | Survival (%) |
|---|---|
| Example 9 i.v. 1 mg/kgbw | 100 |
| Example 10 i.v. 1 mg/kgbw | 67 |
| Example 7 i.v. 1 mg/kgbw | 80 |
| Example 6 i.v. 1 mg/kgbw | 100 |
| Example 79 i.v. 1 mg/kgbw | 100 |
| Example 1 i.v. 1 mg/kgbw | 100 |
| Example 16 i.v. 1 mg/kgbw | 67 |
| Example 65 i.v. 1 mg/kgbw | 78 |
| Example 54 i.v. 1 mg/kgbw | 80 |
| Example 20 i.v. 1 mg/kgbw | 100 |
| Example 22 i.v. 1 mg/kgbw | 100 |
| Example 47 i.v. 1 mg/kgbw | 100 |
| Example 39 i.v. 1 mg/kgbw | 60 |
| Example 51 i.v. 1 mg/kgbw | 75 |
| Example 64 i.v. 1 mg/kgbw | 100 |
| Example 56 i.v. 1 mg/kgbw | 67 |
| Example 57 i.v. 1 mg/kgbw | 67 |
| Example 58 i.v. 1 mg/kgbw | 100 |
| Example 59 i.v. 1 mg/kgbw | 86 |
| Example 60 i.v. 1 mg/kgbw | 60 |
| Example 61 i.v. 1 mg/kgbw | 83 |
| Example 55 i.v. 1 mg/kgbw | 80 |
| Example 66 i.v. 1 mg/kgbw | 57 |
| Example 62 i.v. 1 mg/kgbw | 57 |
| Example 63 i.v. 1 mg/kgbw | 50 |
| Example 4 i.v. 1 mg/kgbw | 50 |
| Control (non-treated) n = 24 | 10 |

In addition to the above compounds, the following compounds have also been found to provide advantageous results:

N-[2-hydroxy-3-(pyrrolidin-1-yl)-propoxy]-3-pyridincarboximidoyl chloride (Z)-2-butendioate (1:1) (U.S. Pat. No. 5,328,906, Example 12, 1 mg/kgbw i.v., survival %: 67):

N-[2-hydroxy-3-(diethyl-amino)-propoxy]-3-pyridincarboximidoyl chloride hydrochloride (1:1) (U.S. Pat. No. 5,328,906, Example 11, 1 mg/kgbw i.v., survival %: 62);

N-[2-hydroxy-3-prop-2-yl-amino)-propoxy]-3-pyridincarboximidoyl chloride (Z)-butendioate (1:1) (U.S. Pat. No. 5,328,906. Example 13/4, 1 mg/kgbw i.v., survival %: 60);

N-[2-hydroxy-3-(morpholin-1-yl)-propoxy]-3-pyridincarboxamidoyl chloride (Z)-2-butendioate (1:1) (U.S. Pat. No. 5,328,906, Example 12, 1 mg/kgbw i.v., survival %: 71);

N-[2-hydroxy-3-(1-piperidyl)-propoxy]-∀-(3,4-dimethoxy-phenyl)-acetimidoyl chloride (U.S. Pat. No. 5,328,906, Example 14, 1 mg/kgbw i.v., survival %: 67);

N-[2-hydroxy-3-(tert-butyl-amino)-propoxy]-3-pyridincarboxamidoyl chloride (Z)-2-butendioate (1:1) (U.S. Pat. No. 5,328,906, Example 13/5, 1 mg/kgbw i, v., survival %: 57);

O-(3-piperidino-2-hydroxy-1-propyl)-benzhydroximic acid chloride hydrochloride (U.S. Pat. No. 5,147,879, Example 1, 1 mg/kgbw i.v., survival %: 100);

N-[2-hydroxy-3-(1-piperidinyl)propoxy]-3-pyridinecarboximidoyl chloride (Z)-2-butendioate (1:1) (U.S. Pat. No. 5,147,879, Example 2, 1 mg/kgbw i.v., survival %: 100.20 mg/kgbw p.o. survival %: 100);

Effect of N-[2-hydroxy-3-(1-piperidinyl)propoxy]-3-pyridinecarboximidoyl Chloride Maleate in Cell Membrane Repair and Preservation of Membrane Fluidity 1. Alteration in Cell Membrane Fluidity Associated with Cellular Injury Induced by Serum Deprivation Stress and Effect of N-[2-hydroxy-3-(1-piperidinyl)propoxy]-3-pyridinecarboximidoyl Chloride Maleate in Reverting the Alternation in Fluidity 1.1 Background One approach to modeling pathophysiological events caused by the stress of metabolic impairment accompanying diabetes is to decrease the level of insulin in the culturing medium. Since insulin is provided by the supplemented serum, partial or total deprivation seemed to be an optimal tool to detect changes in different regulatory levels of the cell.

Serum deprivation is widely used method for cell arrest in G1/S phase, i.e. cell cycle synchronization (Ashihara. T. *Methods of Enzymology*, 58:248-249 (1979)). It has been observed that cultured cells are undergoing apoptotic processes in the lack of serum supplementation (Cohen, et al., *Adv. In Immunology* 50:50-85 (1991)) and it has been studied as an alternative shock of staurosporin or toposiomerase inhibitors in Balb/3T3 cells (Kulkarni. G. V, et al., *J Cell. Sci.* 107: 1169-1179 (1994)), or heat shock and glutamine deprivation in Ehrlich cells (Rowlands, A G. et al., *Eur. J. Biochem.* 175: 93-99 (1988)) to investigate the inhibited protein synthesis by the phosphorylation of the eukaryotic initiation factor (eIF2 alpha). Moreover, there are evidences on the induction of cytoprotection in serum deprived cells by administering external HSP72 (Johnson, A. D. et al., *In Vitro Cell Dev. Biol. Anim.* 29A:807-812 (1993)). Increases in the relative synthesis of HSP82 and HSP72 by serum deprivation (Toye, P. et al., *Mol. Biochem. Parasitol.* 35, 11-10 (1989)) was also shown.

Ischemic and hypoxic injury of the myocardium and other organs is mediated by progressive membrane dysfunction and damage. It was also demonstrated that alteration in membrane fluidity occurs during metabolic impairment of cardiac cells (Buja L. M. et al, *In vivo* 5: 233-238 (1991)). Membrane fluidity primarily reflects the orientation and rate of the movement of membrane constituent lipids and any alteration of its level greatly influences the fundamental membrane function (Quinn, P. J. et al. *Prog. Biophys. Molec. Biol.* 53: 71-103 (1989); Schlame, M. et al., *Biochim. Biophys. Acta*, 1045: 1-8 (1990)).

In this experiment, investigation was conducted to determine whether changes in plasma membrane fluidity participate in the development in the cellular injury induced by serum deprivation and whether the serum deprivation induced fluidity alteration can be reverted by the administration of N-[2-hydroxy-3-(1-piperidinyl)propoxy]-3-pyridinecarboximidoyl chloride maleate.

1.2 Materials and Methods

Experiments were carried out using WEH1 mouse fibrosarcoma and H9c2 rat heart muscle cell lines divided into three groups:
control (10% FCS fetal calf serum)
serum deprived
N-[2-hydroxy-3-(1-piperidinyl)propoxy]-3-pyridinecarboximidoyl chloride maleate ($10^{-5}$ M) treated and serum deprived 1.2(i) Serum Deprivation and MTT Test We have screened various cell lines, drug concentrations, pretreatment and deprivation times and we have found the most appropriate conditions as follows: $5 \times 10^{-4}$/ml H9c2 rat heart muscle cell (n=6) and WEHI mouse fibrosarcoma cell (n=7) have been plated on 24 well plates in 10% FCS DMEM (Dulbecco modified Eagle's medium) and incubated for 2 hours at 37 C, 5% $CO_2$. Medium has been discarded and replaced by 10% FCS DMEM containing $10^{-5}$ M N-[2-hydroxy-3-(1-piperidinyl)propoxy ]-3-pyridinecarboximidoyl chloride maleate. After further incubation on the above circumstances for 6 hours, plates have been washed intensively by PBS and serum deprived. Pretreated cells were administered with N-[2-hydroxy-3-(1-piperidinyl) propoxy]-3-pyridinecarboximidoyl chloride maleate until the end of the experiment. Following 18 hours starvation, most of the cells were detached, i.e., died, observed microscopically, in serum deprived culture, while N-[2-hydroxy-3-(1-piperidinyl)propoxy]-3-pyridinecarboximidoyl chloride maleate pretreated cultures have shown similar picture to the control cells. Cell viability was measured by MTT test based on the method of Plumb et al. (*Cancer Res.* 49: 4435-4444 (1989)) The tetrazolium salt method involving conversion of MTT (3-(4,5-dimethylthiazol-2yl)-2,5-diphenyltetrazolium bromide) to colored formazan by alive cells, served as an indirect measurement of cell viability. MTT has been added directly to the medium at a concentration of 1 mg/ml. After 2 hr incubation at 37° C. in dark, the supernatant was removed and 200:1 of 0.05 M HCl in isopropanol was added immediately to the cells. O.D. of the plates was read at 570 nm on an ELISA plate reader (Labsystems Multiskan Biochromatic type:348). Experiments have been carried out in each case at least in triplicates. Relative cell viability was calculated defining control group as 100%.

1.2(ii) Determination of Steady-State Fluorescence Anisotropy

Cell suspensions of Ix $10^{-5}$ cells/ml in PBS were labeled by the addition of DPH-PA (3-[p-(6-Phenyl)-1,3,5-hexatrienyl] phenylpropionic acid) dissolved in tetrahydrofuran at a final concentration of 0.1 :M and incubated for 10 min. at 37 C. The amount of organic solvent added was 0.05% to avoid its effect on cell membranes. The membrane probe DPH-PA was selected due to charge properties of the probe that enable DPH-PA to localize predominantly within the outer leaflet of the plasma membrane, with the diphenyl-hexatriene moiety intercalating between upper portions of fatty acyl chains (Kitagawa, S., et al. *J. Membrane Biol.* 119:221-227 (1991)). DPH-PA exhibits strong fluorescence enhancement upon binding to lipids, providing a means of evaluating fluorescence anisotropy as a function of lipid ordering. Fluorescence measurements were carried out at 37° C. using a Quanta Master QM-1 T-format luminescence spectrometer (Photon Technology Int. Inc., N.J. USA) equipped with polarizers in the excitation and in the two emission light path. Excitation and emission wavelengths were 360 nm (5 nm slit width) and 430 nm (5 nm slit width), respectively. The measured fluorescence intensities were corrected for background fluorescence and light scattering from the unlabeled sample. The fluorescence anisotropy was calculated as $$rs = (IVV - G \cdot IVH)/(IVV + (2 \times G \times IVH))$$

where IVV and IVH are observed intensities measured with polarizers parallel and perpendicular to the vertically polarized exciting beam, respectively. The factor G equals IVH/IHH and corrects for the inability of the instrument to transmit differently polarized light equally and for the difference in sensitivity of the two emission channel (Kitagawa, S., et al. *J Membrane Biol.* 119:121-227 (1991)). IHV and IHH are the fluorescence intensities determined at vertical and horizontal positions of the emission polarizer when the excitation polarizer is set horizontally.

1.2(iii) Statistical Analysis

Data are reported as means±SEM. Statistical comparison and calculation was performed by one way analysis or variance with Posthoc Newman-Keuls test (Pharmacological Calculation System). Statistical significance was defined as $P<0.05$.

1.3 Results 1.3(i) Serum Deprivation as a Model to Test Cytoprotective Effect of N-[2-hydroxy-3-(1-piperidinyl) propoxy]-3-pyridinecarboximidoyl Chloride Maleate Serum deprived WEHI and H9c2 cells showed 74.8% and 50.5% relative cell viability, respectively. In case if $10^{-5}$ M N-[2-hydroxy-3-(1-piperidinyl)propoxy]-3-pyridinecarboximidoyl chloride maleate was present in the culture medium the administration resulted in an almost total survival of WEHI (93%) and a high protection in H9c2 heart muscle cells (82.75%). Decrease of relative cell viability by serum deprivation and its protection by N-[2-hydroxy-3-(1-piperidinyl) propoxy]-3-pyridinecarboximidoyl chloride maleate in both cell lines were significant.

1.3(ii) Effect of N-[2-hydroxy-3-(1-piperidinyl)propoxy]-3-pyridinecarboximidoyl Chloride Maleate on the Fluidity of Serum Deprived Mammalian Cells To examine the effect of serum deprivation on the plasma membrane fluidity of cultured mammalian cells fluorescence anisotropy measurements have been accomplished by using the plasma membrane probe DPH-PA. The physical properties of the cell plasma membranes were significantly altered by serum deprivation. Serum deprivation caused a pronounced decrease in fluorescence anisotropy of DPH-PA that is an abnormal increase in plasma membrane fluidity in both cell models investigated. Upon the addition of N-[2-hydroxy-3-(1-piperidinyl)propoxy]-3-pyridinecarboximidoyl chloride maleate we observed an almost complete preservation of the membrane physical state. These changes were obviously consistent with the tendencies described on cell viability.

1.4 Discussion

By resulting in metabolic impairments, deprivation of normal culture medium in both type of cells studied reduced their viability as tested with the MTT method. This effect was almost fully reverted upon the addition of N-[2-hydroxy-3-(1-piperidinyl)propoxy]-3-pyridinecarboximidoyl chloride maleate. Deprivation of serum induced also prominent alterations in the fluidity of plasma membranes which is known to contribute to the membrane dysfunction accompanying myocardial injury. In contrary, serum deprived cells, grown in the presence of N-[2-hydroxy-3-(1-piperidinyl)propoxy]-3-pyridinecarboximidoyl chloride maleate, were able to preserve (or retain) partially their normal plasma membrane physical state.

Effect of Insulin and N-[2-hydroxy-3-(1-piperidinyl)-propoxy]-3-pyridinecarboximidoyl Chloride Maleate on the Level of GRP-94 in STZ Diabetic Rat Liver 1. Background Anoxia, glucose starvation and several other conditions that adversely affect the function of endoplasmic reticulum (ER) induce the synthesis of the glucose regulated class of stress proteins (GRPs) (Lin, H. Y., et al. *Mol. Biol. Cell.* 4:1109-1119 (1993)). The 94 kDa member of GRPs, GRP-94, 50% homologous to 90 kDa stress protein, is a lumenal calcium-binding protein of ER. Together with other proteins of ER, GRP-94 appears to function as a molecular chaperon (Nigem, S. K., et al. *J. Biol. Chem.* 263; 1744-1749 (1994)). It is assumed that the accumulation of molecular chaperone GRP-94 should have a beneficial effect on the repairing of cellular damage induced by STZ diabetes in rats. Accordingly, in the experiments set forth herein we compared the various levels of GRP-94 in livers derived from healthy, diabetic, N-[2-hydroxy-3-(1-piperidinyl)propoxy]-3-pyridinecarboximidoyl chloride maleate treated and insulin plus N-[2 hydroxy-3-(1-piperidinyl)propoxy]-3-pyridinecarboximidoyl chloride maleate treated rats.

2. Materials & Methods 2.1 Test Substances: N-[2-hydroxy-3-(1-piperidinyl)propoxy]-3-pyridinecarboximidoyl Chloride Maleate (BIOREX Ltd.) Insulin (Protophane HM inj.)

2.2 Animals: Crl (VAF plus) Wistar Male Rats (250-300 g)

Animals were housed 7 per cage at 23-25° C. at 50-60% relative humidity with 12/12 hours light-dark cycle. Free access was given to chow and tap water 2.3 Induction of Diabetes: A Single Dose of STZ (45 mg/kg i.v.) was Given in Fasting State.

2.4 Animals were Divided into the Following Groups:

a. Healthy Animals
1. Saline treated healthy for 1 weeks (n=5)
2. Saline treated healthy for 2 weeks (n=5)
3. Saline treated healthy for 4 weeks (n=5)
4. N-[2-hydroxy-3-(1-piperidinyl)propoxy]-3-pyridinecarboximidoyl chloride maleate treated for 1 weeks (n=7)
5. N-[2-hydroxy-3-(1-piperidinyl)propoxy]-3-pyridinecarboximidoyl chloride maleate treated for 2 weeks (n=7)
6. N-[2-hydroxy-3-(1-piperidinyl)propoxy]-3-pyridinecarboximidoyl chloride maleate treated for 4 weeks (n=7)

b. STZ-Diabetic Animals
7. Saline treated diabetic for 1 weeks (n=5)
8. Saline treated diabetic for 2 weeks (n=5)
9. Saline treated diabetic for 4 weeks (n=5)
10. N-[2-hydroxy-3-(1-piperidinyl)propoxy]-3-pyridinecarboximidoyl chloride maleate treated diabetic for 1 weeks (n=7)
11. N-[2-hydroxy-3-(1-piperidinyl)propoxy]-3-pyridinecarboximidoyl chloride maleate treated diabetic for 2 weeks (n=7)
12. N-[2-hydroxy-3-(1-piperidinyl)propoxy]-3-pyridinecarboximidoyl chloride maleate treated diabetic for 4 weeks (n=7)

c. Insulinized STZ-Diabetic Animals
13. 1-week insulin treated diabetic (n=7)
14. 2-week insulin treated diabetic (n=7)
15. 4-week insulin treated diabetic (n=7)

d. N-[2-hydroxy-3-(1-piperidinyl)propoxy]-3-pyridinecarboximidoyl Chloride Maleate Treated and Insulinized Diabetic Animals
16. 1-week insulin and N-[2-hydroxy-3-(1-piperidinyl)propoxy]-3-pyridinecarboximidoyl chloride maleate treated diabetic (n=7)
17. 2-week insulin and N-[2-hydroxy-3-(1-piperidinyl)propoxy]-3-pyridinecarboximidoyl chloride maleate treated diabetic (n=7)
18. 4-week insulin and N-[2-hydroxy-3-(-1-piperidinyl)propoxy]-3-pyridinecarboximidoyl chloride maleate treated diabetic (n=7)

After the treatments liver was removed, and was immediately frozen at −70° C. in liquid nitrogen. N-[2-hydroxy-3-(1-piperidinyl)propoxy]-3-pyridinecarboximidoyl chloride maleate treatment (wherever applicable): 20 mg/kg/day, p.o. Insulin treatment: twice daily in a dose required to maintain normal glucose level.

2.5 Determination the Level of GRP-94.

Extraction of Total Soluble Protein from Rat Liver.

All steps were carried out at 0-4 C. Rat livers (about 15-20 g) were homogenized with a domestic mixer for 2 min. in 80 ml of a modified single detergent lysis buffer solution containing 50 mM Tris-HCl pH 8.0, 5 mM EDTA, 150 mM NaCl, 0.1% SDS, 1% Triton X-100 and 1-1 mM pro-tease inhibitors (PMSF, benzamidine, amino-caproic-acid). The homogenate was centrifuged at 20000×g for 30 min. in a Servile RC 28S centrifuge. The majority of the supernatant was frozen to −20° C. as a stock sample), 1 ml was used for the analysis.

Protein concentration was determined by the Bradford assay (Guide to Protein Purification. *Methods in Enzimology*. vol. 182. M. P. Deutscher (Ed.), Academic Press (1990)) in three parallel and was adjusted to 5 mg/ml.

Electrophoresis and Immunoblotting

Laboratory techniques for electrophoresis and immunoblotting are described in detail in *Molecular Cloning, A Laboratory Manual*, Ed. Sambrook, Fritsche, Maniatis, Bold Spring Harbor Laboratory Press (1989): *Protein Blotting Protocols for the Immobilon-P Transfer Membrane*, 3. Laboratory Manual, Millipore: and U. K. Laemmli, *Nature*: 227: 680-685 (1970). Each sample consisted of 1.8 mg protein was solubilized for gel-electrophoresis with 0.6 ml buffer containing 110 mM Tris-HCl pH 6.8, 8.3 mM mercaptoethanol, 3% SDS, 3% glycerol and some bromophenol blue and shaken at room temperature for 30 min. Electrophoresis was carried out on 8% polyacrylamide gel with 30 mg protein per lane at constant voltage 50 V for overnight. Proteins were either stained with Coomassie Brilliant Blue R-250 or transferred to Immobilone PVDF membrane (Millipore) at constant current (300 mA) for 3 hours at 4° C. in transfer buffer (10 mM CAPS pH 11.10% methanol). Non-specific sites of the membrane were blocked with 2% BSA in TPBS (phosphate buffered saline with 0.1% Tween 20) for overnight at 4 C. The blot was incubated with GRP-94 monoclonal antibody (SPA-850, StressGen) diluted 1:3000 for 1 hour at room temperature. Then it was washed with TPBS buffer for another one hour, and incubated with horseradish peroxidase conjugated anti-rat secondary antibody (Sigma, I:4000 dilution) for 1 hour. After successive washing with TPBS the membrane was developed with ECL system (Amersham).

A total-protein (9/1 sample) dilution series was blotted and developed parallel with the samples every time, and a calibration curve was calculated. The changes in the stress protein content was quantified using a Bio-Rad densitometer model 1650) and a Hewlett-Packard Integrator (11 P 3394A) and corrected according to the calibration curve.

Statistical Analysis

Data are reported as means±SEM. Statistical comparison and calculation was performed by one-way analysis of variance with Posthoc Newman-Keuls test (Pharmacological Calculation System). Statistical significance was defined as P<0.05.

3. Results

Significant decrease of relative GRP-94 content is observed in 1 week, 2-weeks and 4-weeks diabetic rats. This effect in 1 week and 2-weeks diabetic animals could completely be reverted upon N-[2-hydroxy-3-(1-piperidinyl)propoxy]-3-pyridinecarboximidoyl chloride maleate treatment. Administration of insulin alone or in combination with N-[2-hydroxy-3-(-1-piperidinyl)propoxy]-3-pyridinecarboximidoyl chloride maleate in 1 week and 2-weeks samples almost doubled the levels of this protein compared to the control state.

In contrast to the previous findings, treatment of rats diabetic for 4 weeks by N-[2-hydroxy-3-(1-piperidinyl)propoxy]-3-pyridinecarboximidoyl chloride maleate alone, resulted in no significant alteration in the relative amount of GRP-94. Moreover, both in the insulinized groups, irrespective either treated or not by N-[2-hydroxy-3-(1-piperidinyl) propoxy]-3-pyridinecarboximidoyl chloride maleate, we observed a recovery of GRP-94 to the control level.

Effect of N-[2-hydroxy-3-(1-piperidinyl)-propoxy]-3-pyridinecarboximidoyl Chloride Maleate in Protecting Epidermal Cells Against Damages Caused by Exposure to Heat and UV Light 1. Materials & Methods HaCaT cell line is a spontaneously immortalized, ancuploid human keratinocyte cell line derived from normal human adult skin (Boukamp et al., J. Cell Biol. 106:761-771 (1988)), HaCaT is a cell line with full epidermal differentiation capacity, with normal keratinization and with nontumorogenic character. This rapidly multiplying keratinocyte line with high ditharnol sensitivity is also characterized by the presence of steroid receptors. HaCaT cells ($4 \times 10^5$ cells per Petri-dish with a diameter of 35 mm) were seeded and grown in DMEM supplemented with 5% fetal calf serum (Gibco, Cat. No. 011-6290H) under a humidified atmosphere of 5% $CO_2$ at 37° C. 24 hours after plating, the cultures were rinsed with PBS and treated by heat or light.

The confluent cultures of the cells were exposed to heat (42, 44, 46, 47, 48° C.) or UV light (UVA I, 2, 4, 6 J/cm$^2$). Heat exposure was provided in circulating water baths. As a UV light source, Waldmann PUVA 4000 was used with an energy spectrum of the final output between 320 an 390 nm, peaking at 365 nm. The energy output was monitored by an IL-1700 radiometer equipped with UVA and UVB sensor.

The morphology of the cells was monitored using phase contrast microscopy (Opton Axioplan Microscope, with Plan-Apochromat Ph phase contrast objectives). The following factors were considered as indicators of cytotoxicity: (a) reduced density of adherent cells; (b) loss of regular "cobblestone" pattern with enlargement of intercellular spaces; (c) alteration of cell shape. e.g., impeded cell spreading, swelling, pycnotic shrinking, fragmentation: and (d) cytoplasmic changes, e.g., condensation or vacuolization. Cell viability was also examined, using Trypan-blue exclusion test.

2. Results

Sensitivity of HaCaT keranitocytes to heat-stress was determined by examining their viability. The results indicated that 24 hours after being exposed to heat at a temperature of 48° C., there were practically no living cells (2.7%), compared to the control (100%) at 37° C. Viability of HaCaT keratinocytes 24 hrs after a 45° C. heat exposure proved to be 59%. There were no morphological changes in HaCaT cultures 1 hr after the heat exposure. 24 hrs after the heat treatment at 46° C. or higher temperature significant (p<0.01) cell detachment and morphological changes occurred, such as the loss of regular "cobble-stone" pattern with the enlargement of intercellular spaces, swelling, pycnotic shrinking, and vacuolization of HaCaT keranitocytes. Following UV exposure, it was found that reduction of viable cells were directly correlated with the dose of UVA.

Preconditioning the cells with heat (42° C. for 1 hour) or N-[2-hydroxy-3-(1-piperidinyl)propoxy]-3-piridinecarboximidoyl chloride maleate (at a concentration of $5 \times 10^5$ M for one hour) provided the cells with protection against a 48° C. heat exposure. When cells were examined 24 hours after the 48° C. treatment, it was found that compared to cells that were not treated, the cell viability increased to 48% (when preconditioned with 42° C.) and 84% (with N-[2-hydroxy-3-(1-piperidinyl)propoxy)-3-piridinecarboxymidoyl chloride maleate pre-treatment). The most pronounced protection (increase of 140% in viability) could be observed in case of a combined treatment (with 42° C. and N-[2-hydroxy-3-(1-piperidinyl)propoxy)-3-pyridinecarboximidoyl chloride maleate).

Heat preconditioning with 42° C., but not with 44° C. and 45° C., induced a prominent reduction of cytotoxicity due to UV-light. A treatment with 42° C. provided protection both at exposure of 2 and 4 J/cm². Viability of pretreated HaCaT kerationocytes increased to 132% (at 2 J/cm²) and to 218% (at 4 J/cm²) compared to UV-exposed cells without pretreatment (100%).

Effect of N-[2-hydroxy-3-(1-piperidinyl)-propoxy]-3-piridinecarboxymidoyl Chloride Maleate in Inducing Molecular Chaperon Expression in Human Skin Tissues Ultraviolet UVB light (290-320 nm) is one of the components of sunlight and is known to cause damage to the skin. The role of N-[2-hydroxy-3-(1)-piperidinyl)propoxy]-3-pyridinecarboximidoyl chloride maleate in reducing damages caused to the skin tissues by the UVB exposure was investigated, as well as the effect of N-[2-hydroxy-3-(1-piperidinyl) propoxy]-3-pyridinecarboximidoyl chloride maleate in increasing the expression of molecular chaperon in the skin tissues.

1. Materials & Methods

Human skin tissues were grafted onto immunodeficiency (SCID) mice. The experimental protocol involved a treatment of one group of the mice with N-[2-hydroxy-3-(1-piperidinyl)propoxy]-3-piridinecarboximidoyl chloride maleate (5.0 mg/kg i.p.) and the other with the solvent NaCl solution (300 µl) for 7 days. On day 8, both groups of mice were exposed to UVB light (100 mJ/cm²) 24 hours subsequent to the exposure, skin biopsies were taken for histological (sections stained with hematoxylin and eosin), and immunohistological examinations (indirect immunoflourescence technique with monoclonal antibody, mAB).

2. Results

In UV-irradiated mice that was pretreated with N-[2-hydroxy-3-(1-piperidinyl)propoxy]-3-piridinecarboximidoyl chloride maleate, clinical signs of injuries due to UV exposure could not be observed. In contrast, in one of the untreated animals a pustulous reaction of the transplanted area was found. Furthermore, indirect immunofluorescence studies using mAB hsp72 showed an intense, linear staining along the basement membrane zone of human and mouse skin of the N-[2-hydroxy-3-(1-piperidinyl)propoxy]-3-pyridinecarboximidoyl chloride maleate treated animals. The same reaction could not be observed in the skin of the untreated animals. In addition, a nuclear type of staining of granulocytes was present in the pustule (inflammatory skin reaction) of the untreated animal.

Accordingly, administration of N-[2-hydroxy-3-(1-piperidinyl)propoxy]-3-pyridinecarboximidoyl chloride maleate to skin tissues resulted in increased formation of hsp72 in skin tissues and provided protection against injuries from UV exposure.

3. Determination of the Level of HSP-70 from Skin: Western Blot Analysis of Proteins Derived from UVB and UVB+N-[2-hydroxy-3-(1-piperidinyl)propoxy]-3-pyridinecarboximidoyl Chloride Maleate Treated Human Skin Grafted in SCID-mouse.

Methods:

a. Extraction of Total Soluble Protein from Skin.

All steps were carried out at room temperature. Skin (about 9-35 mg) was cut into tiny pieces and homogenized with frosted-glass pestle in Eppendorf tubes for 2 min. in (2 µl/µg skin) of 2 times concentrated Laemmli buffer (65 mM Tris-HCI, pH 6.8: 5% β-mercaptoethanol; 2% SDS; 10% glycerol; 0.1% bromophenolblue; all of these materials were Sigma products). Then samples were solubilized for another 60 min. with continuous shaking. The homogenates were centrifuged at 10.000 rpm for 10 min. prior loading to the gel.

b. Electrophoresis and Immunoblotting [5, 7, 8]

Electrophoresis were carried out on 8% polyacrylamide gel with 10 µl of sample per lane at constant voltage (50 V) for overnight.

Proteins were either stained with Coomassie Brilliant Blue R-250 or transferred to Immobilone PVDF membrane (Millipore) at constant current (300 mA) for 3 hours at 4° C. in transfer buffer (10 mM CAPS pH 11, 10% methanol).

Non-specific sites of the membrane were blocked with 2% BSA in TPBS (phosphate buffered saline with 0.1% Tween 20) for overnight at 4° C. The blot were incubated with HSP-70 monoclonal antibody (SPA-8dc., StressGen) diluted 1:1500 for 1 hour at room temperature. Then it was washed three times with TPBS buffer for another one hour, and incubated with horseradish peroxidase conjugated anti-mouse secondary antibody (Sigma, 1:1500 dilution) for 1 hour.

After successive washing (three times) with TPBS. the membrane was developed with ECL System (Amersham).

Effect of N-[2-hydroxy-3-(1-piperidinyl)propoxy]-3-(piridinecarboxymidoyl Chloride Maleate in Activation of HSP Formation and Production of Oxidative Phosphorylation)

1. Background

It has been shown that exposing *Saccharomyces cerevisiae* cells to heat shock (5 min. at 42-44° C.) resulted in an impairment of coupling of oxidative phosphorylation and mitochondrial electron transport system, affecting the ability of the cells to synthesize ATP (Patriarca et al., Bio-chemistry and Cell Biology, 70:207-214, 1992). However, when the cells were pre-treated with N-[2-hydroxy-3-(1-piperidinyl)propoxy]-3-piridinecarboximidoyl chloride maleate for a short period of time at 37° C. prior to heat shock, it lessened the impairment of the coupling and protected mitochondrial ATP synthesis. Inhibition of cytoplasmic RNA or protein synthesis during heat shock appears to prevent this protection of mitochondrial activity. Accordingly, one of the roles of hsp seems to be that of protecting the coupling of oxidative phosphorylation and mito-chondrial electron transport system which is disturbed when cells are exposed to physiological stress, e.g., heat shock.

In this section, N-[2-hydroxy-3-(1-piperidinyl)propoxy]-3-piridinecarboxymidoyl chloride maleate is administered to cells prior to being exposed to heat shock, and its effect on protecting coupling of oxidative phosphorylation with mitochondrial transport system against the heat stress is examined.

It was also investigated if the activity of AP-1 and P 1 transcription factors can be modulated by N-[2-hydroxy-3-(1-piperidinyl)propoxy]-3-piridinecarboximidoyl chloride maleate in yeast cells exposed to various stress conditions.

2. Materials & Methods

The experimental protocol for determining the impairment of oxidative phosphorylation and mitochondrial ATP synthesis in *Saccharomyces cerevisiae* is provided in Patriarca et al., Bio-chemistry and Cell Biology, 70:207-214, 1992, said reference being fully incorporated herein by reference.

To *S. cerevisiae* cells that were maintained at 25° C., varying concentration of N-[2-hydroxy-3-(1-piperidinyl)propoxy]-3-piridinecarboximidoyl chloride maleate was introduced (concentrations between 10 to 100 μM), cells were then incubated for one hour at 25° C. in the presence of N-[2-hydroxy-3-(1-piperidinyl)propoxy]-3-piridinecarboximidoyl chloride maleate. The temperature was then increased to 42° C., and the oxygraph measurements were taken as described in the Patriarca reference.

The cells treated with N-[2-hydroxy-3-(1-piperidinyl)propoxy]-3-pyridine carboximidoyl chloride maleate were tested for concomitant induction of hsp genes, using Northern Blotting procedure. The method of extracting, purifying mRNAs from eukaryotic cells, and analyzing the RNA thus obtained using Northern blotting procedure is well known in the art and described in Maniatis, and Maresca, et al. *Archives Medial Research* 24: 247-249 (1993), both of the references being fully incorporated herein. The Northern blotting protocol is also described in Example 7 set forth above. Hsp 26 and hsp70 DNA sequences were used as probes.

3. Results 3.1

Figure 4:
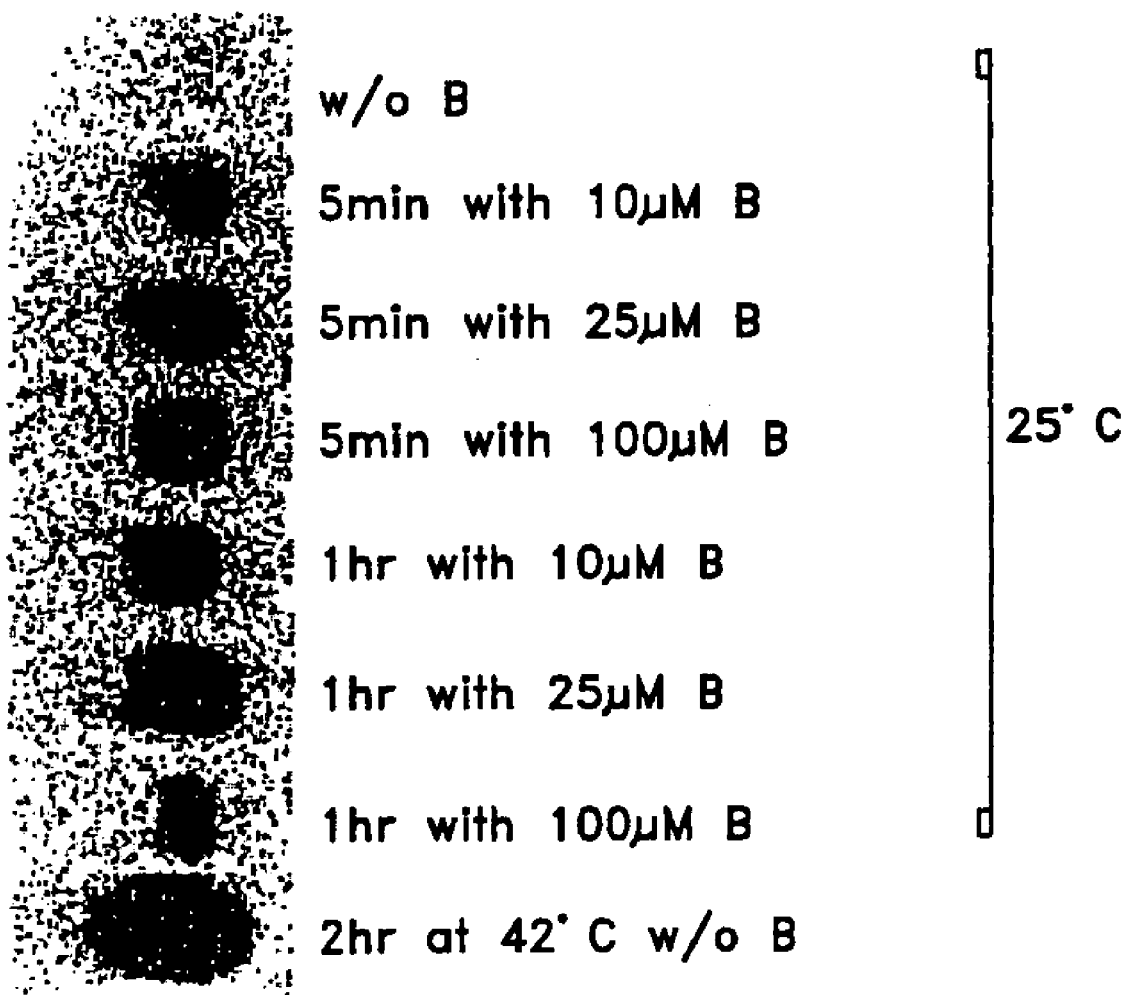
FIG. 4 shows the results of hsp26 mRNA Northern blot analysis obtained on *Saccharomyces cerevisiae* cells during examination of the effect of compound B on hsp activation.

FIG. 4 is the Northern blot analysis of hsp26 mRNA induced in *S. cerevisiae*, illustrating the results obtained from the experiment. The concentration of the chemical compound administered to the cells and the duration of incubation in the compound are indicated.

In the cells that were incubated in the presence of N-[2-hydroxy-3-(1-piperidinyl)propoxy]-3-piridinecarboxymidoyl chloride maleate (10-100 μM) for 5 min. to 1 hour at 25° C., the induction of hsp 26 was observed. The results also seem to indicate that the induction occurs even after 5 minute incubation.

It was also found that concentrations between 10 and 100 μM of test compound was effective in lessening the impairment of the coupling between oxidative phosphorylation and mitochondrial electron transport system that results from heat shock. The protection from the impairment of mitochondrial ATP synthesis was in the range obtained when thermotolerance was induced by pre-conditioning the cells by exposing them to the intermediate temperature of 37° C. (40-60% protection).

3.2

Figure 5:
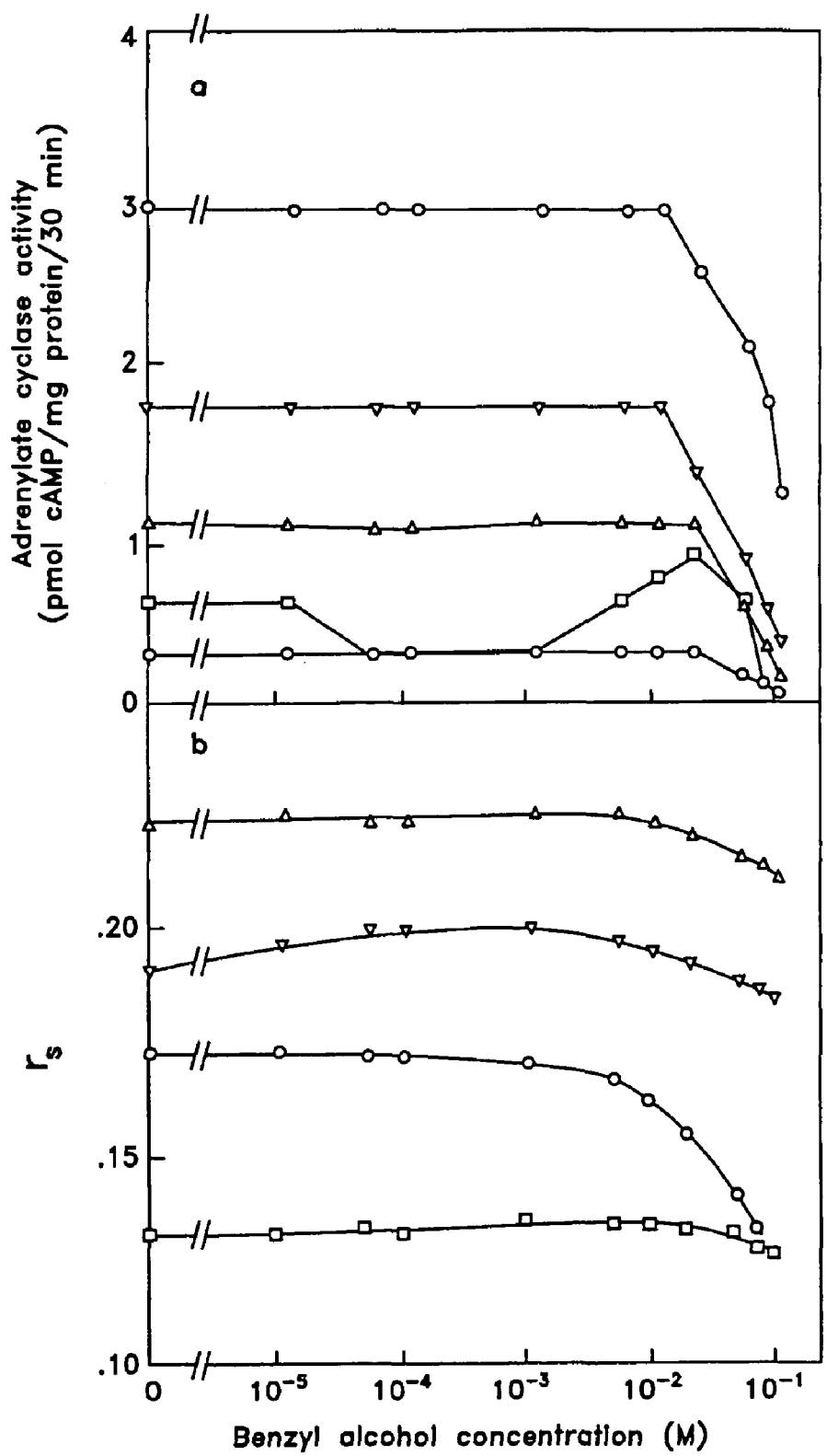
FIG. 5 shows the effect of benzyl alcohol on the adenylate cyclate activation and the membrane state of plasma.

The effect of benzyl alcohol on (a) adenylate cyclase activity and (b) the physical state of bovine thyroid plasma membranes are shown on FIG. 5. Effect of benzyl alcohol on (a) the adenylate cyclase activity and (b) the physical state of bovine thyroid plasma membranes. The change in adenylate cyclase activity (a) is shown for basal (o-o). TSH-stimulated (-), forskolin-stimulated (ε-ε), choleratoxin-stimulated (∇-∇), and fluoride-stimulated (◊-◊) enzyme activity. The membranes were incubated with the drugs prior to the addition of coupling factors. The physical state of the membrane was evaluated by following the steady-state fluorescence anisotropy (b) of several fluorophores embedded in the membranes: DPH (o-o). 12-AS (-) and TMA-DPH (ε-ε). Measurements were performed at 37° C. The flourophore/lipid molar ratio was always 1:500.

3.3

Our experiments proved that N-[2-hydroxy-3-(1-piperidinyl)propoxy]-3-pyridine carboximidoyl chloride maleate exerts a significant influence on the activity of AP-1 and its effect is determined by the actual metabolic conditions of the cells. While N-[2-hydroxy-3-(1-piperidinyl)propoxy]-3-piridinecarboximidoyl chloride maleate increases the activity of AP-1 if the supply of nutrients is inadequate, in rich medium it does decrease the activity of the factor. The effect of the drug is most pronounced in dense, late log cultures. The opposite tendency could be seen for P 1. Its activity decreased if N-[2-hydroxy-3-(1-piperidinyl)propoxy]-3-pyridine carboximidoyl chloride maleate was administered to cells in a minimal medium. It is conceivable, that the downregulation of P-1 was elicited by the very changes in the cells anti-stress machinery caused by the N-[2-hydroxy-3-(1-piperidinyl) propoxy]-3-piridinecarboximidoyl chloride maleate induced AP-1 activation. It is noted, that P-1 responded to all types of stresses but its activity was not influenced by the test material. Our important findings, especially with AP-1 could explain many facets of the in vivo activity of the drug and will be discussed in details.

Figure 6:
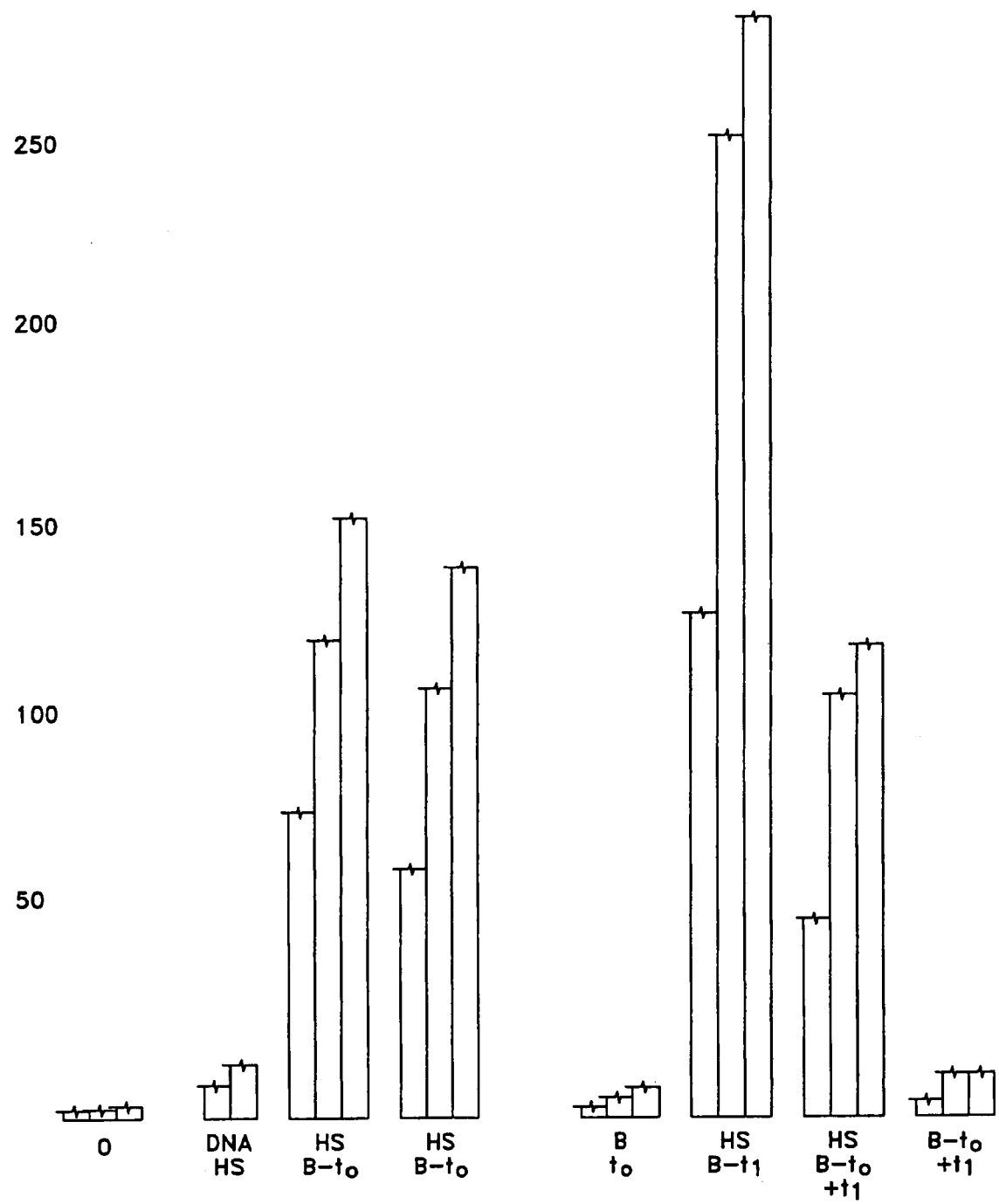
FIG. 6 shows the hsp gene expression rate on HeLa cells, using luciferase reporter gene for the test.

The effect of N-[2-hydroxy-3-(1-piperidinyl)propoxy]-3-piridinecarboximidoyl chloride maleate (B) on hsp gene expression in tissue culture is shown in FIG. 6. HeLa cells were transfected with a reporter plasmid construct in which the promoter of human hsp70 gene was fused to the luciferase reporter gene. The effect of heat shock and/or N-[2-hydroxy-3-(1-piperidinyl)propoxy]-3-piridinecarboximidoyl chloride maleate on the hsp promoter was determined by measuring the activity of luciferase in luminometer and by determining the hsp protein level (expressed from the chromosomal gene) on Western blot.

Samples are:
1: no DNA control; 2: 10 μg transfected DNA at $t_0$, no heat shock; 3: 10 μg transfected DNA at $t_0$ 60 min. heat shock 24 h later; 4: as earlier+N-[2-hydroxy-3-(1-piperidinyl)propoxy]-3-pyridin carboximidoyl chloride maleate (B) at $t_0$: 5: 10 kg transfected DNA at $t_0$+N-[hydroxyl-3-(1-piperidinyl)propoxy]-3-piridinecarboximidoyl chloride maleate (B) at $t_0$: 6: 10 μg transfected DNA at to 60 min. heat shock 24 h later N-[2-hydroxy-3-(1-piperidinyl)propoxy]-3-pyridine carboximidoyl chloride maleate (B) added at the time of heat shock; 7: 10 μg transfected DNA at to 60 min. heat shock 24 h later N-[2-hydroxy-3-(1-piperidinyl)propoxy]-3-piridinecarboxymidoyl chloride maleate (B) added at 0 time and at the time of heat shock: 8: 10 μg transfected DNA at to with no heat shock, N-[2-hydroxy-3-(1-piperidinyl)propoxy]-3-piridinecarboxymidoyl chloride maleate (B) added at 0 time and 24 h later.

Effect of N-[2-hydroxy-3-(1-piperidinyl)propoxy]-3-piridinecarboxymidoyl Chloride Maleate in Inducing Molecular Chaperon in Tumor Cells Nonlethal heat shock increases the sensitivity to lysis mediated by NK cells by 1.5-fold and that heat shock plus treatment with N-[2-hydroxy-3-(1-piperidinyl)propoxy]-3-pyridine carboximidoyl chloride maleate has a synergistic effect on the lisability of K562 cells. This additional effect accounted for N-[2-hydroxy-3-(1-piperidinyl)propoxy]-3-piridinecarboximidoyl chloride maleate clearly resulted from the elevated plasma membrane expression of hsp72, since in vivo antibody blocking studies (using hsp72 specific monoclonal Ab) revealed a strong inhibition of NK-lysis.

Figure 7:
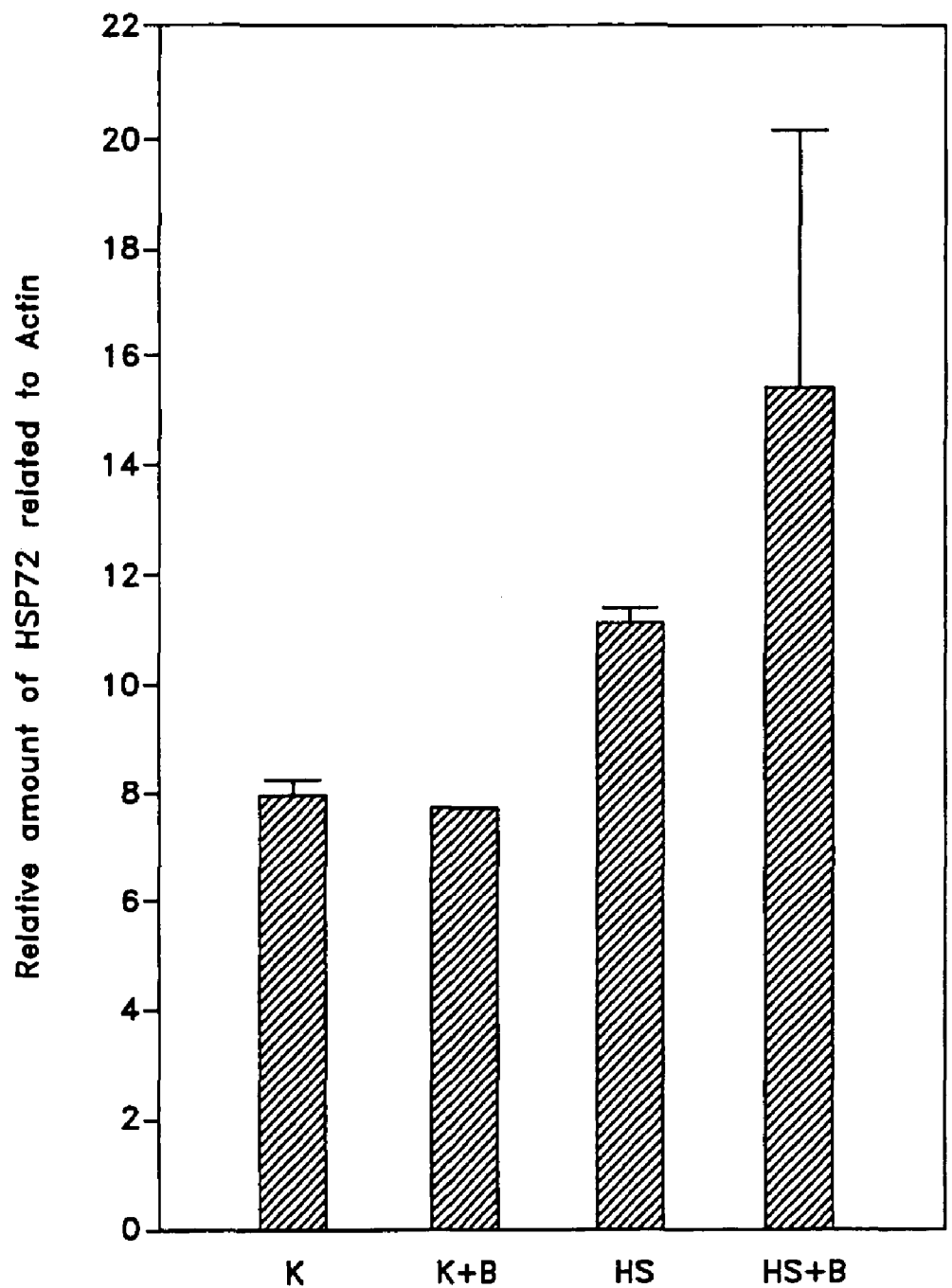
FIG. 7 illustrates the effect of compound B on hsp72 cell surface expression in K562 cell line.

On FIG. 7, the effect of N-[2-hydroxy-3-(1-piperidinyl)propoxy]-3-piridinecarboximidoyl chloride maleate (B) on heat shock induced hsp72 levels is shown. N-[2-hydroxy-3-(1-piperidinyl)propoxy]-3-piridinecarboximidoyl chloride maleate alone did not increase hsp72 levels while the combination of heat shock and N-[2-hydroxy-3-(1-piperidinyl)propoxy]-3-piridinecarboxymidoyl chloride maleate treatment resulted in a significant increase of hsp72 expression compared to heat shock alone.

1. Background

Heat shock proteins are known to be located in the cytoplasm, where they perform a variety of chaperoning functions. In tumor cells, however, hsp is reported to be expressed also on the surface of cell membrane (Ferrarini, M. et al. Int. J. Cancer, 51, 613, 619, (1992)). Experiments seem to indicate that increased hsp (e.g. hsp70) on cell surface is induced by exposure of tumor cells to nonlethal heat shock, and this increase correlates with an increased sensitivity of IL-2 specific, CD-3 natural killer cells (NK) toward tumor cells. Since NK cells are reported to participate in infiltrating and killing tumor cells in vivo (Kurosawa, S. et al. Eur. J. Immunol. 23:1029, (1993)), this increased sensitivity of NK cells towards tumor cells allows better targeting of the tumor cells by NK cells. Thus, if the expression of hsp can be induced in tumor cells, with increased hsp on the cell surface, it can allow better targeting and killing of these cells by the NK cells. In this section, the effect of N-[2-hydroxy-3-(1-piperidinyl)propoxy]-3-piridinecarboximidoyl chloride maleate in inducing expression of hsp72 in tumor cells is examined.

2. Materials & Methods

Human K562 cells, a myeloid tumor cell line derived from a patient with chronic myelogenous leukemia in blast phase (ATCC, CCL243) was used (Lozzio, B C and Lozzio, B B Blood 45:321, 1975). Exponentially growing cells were treated with $5 \times 10^{-5}$ M N-[2-hydroxy-3-(1-piperidinyl)propoxy]-3-(1-piperdinecarboximidoyl chloride maleate during the nonlethal temperature (42° C.) for 2 hours. Following a recovery period of 16 hrs at 37° C., cells were tested for the level of hsp72 content by flow-cytometry (Multhoff et al., Int. J. Cancer: 61, 272-279, (1995)). Treatment with N-[2-hydroxy-3-(1-piperidinyl)propoxy]-3-piridinecarboximidoyl chloride maleate resulted in an enhanced level of hsp72 in the tumor cells.

Interaction of N-[2-hydroxy-3-(1-piperidinyl)propoxy]-3-piridinecarboxymidoyl Chloride Maleate with Lipid Membranes. A Monolayer Study 1. Background The mechanism(s) by which stress (physical, pathophysiological, etc.) is detected as a signal and transduced to the transcriptional apparatus is hitherto unknown. It was assumed that the physical state of the membrane lipid matrix, which determines the structure and function of the membrane-bound proteins, is directly involved in the perception of temperature changes and that under heat shock (HS) conditions perturbance of membrane structure causes transduction of a signal that induces transcription of HS genes. Parallelly with the induction of stress tolerance, N-[2-hydroxy-3-(1-piperidinyl)propoxy]-3-piridinecarboxymidoyl chloride maleate was shown to enhance the efficacy of cells to detect and signal various stress conditions by upregulating the expression of some chaperone genes.

It is known that monolayer technique using monomolecular lipid layers spread at the air-water interface is an effective tool for the verification of the presence of interactions between membranes and membrane active agents. The behavior of the bilayer system is very similar to that of the respective monolayer system in many aspects (molecular area of membrane constituents, phospholipase action, orientation of inserted proteins, etc.). By measuring the surface pressure changes caused by molecules inserted into monolayers it becomes possible to get insight into the molecular dimension of the interaction.

The crucial prerequisite of the assumption that some N-[2-hydroxy-3-(1-piperidinyl) propoxy]-3-piridinecarboxymidoyl chloride maleate mediated early triggering events in stress responses may occur in the cell membrane is to serve evidences on the direct physical interaction of N-[2-hydroxy-3-(1-piperidinyl)propoxy]-3-piridinecarboximidoyl chloride maleate with membrane constituents. The aim of the present study was to investigate the interaction of N-[2-hydroxy-3-(1 piperidinyl)propoxy]-3-piridinecarboximidoyl chloride maleate with membranes by using different lipid monolayers as model system for biological membranes.

2. Materials and Methods

Monolayer experiments were carried out in a Teflon dish, with a volume of 6.5 ml, and a surface area of 8.8 cm² at 25° C. in a KSV3000 Langmuir-Blodgett instrument (KSV Instruments Ltd., Helsinki, Finland) essentially as described. Monomolecular lipid layers consisting of 1,2-dipalmitoyl-sn-glycero-3-phosphocholine (DPPC), egg yolk phosphatidylglycerol (EggpG) or bovine heart cardiolipin (BHCL) were spread from chloroform lipid solutions to give the desired initial surface pressure on a subphase of 10 mM Na-phosphate (pH 7.0). The subphase was continuously stirred with a magnetic bar. N-[2-hydroxy-3-(1-piperidinyl)propoxy]-3-pyridine carboximidoyl chloride maleate, dissolved in $H_2O$, was added underneath the monolayer through a hole in the Teflon chamber connected to the subphase. The injected volumes were always <1% of the total subphase volume. The surface pressure was measured by the Wilhelmy method using a platinum plate. The surface pressure increase data were extracted from the raw data files by using the LB5000 software of the Langmuir-Blodget measuring system.

3. Results

Figure 8:
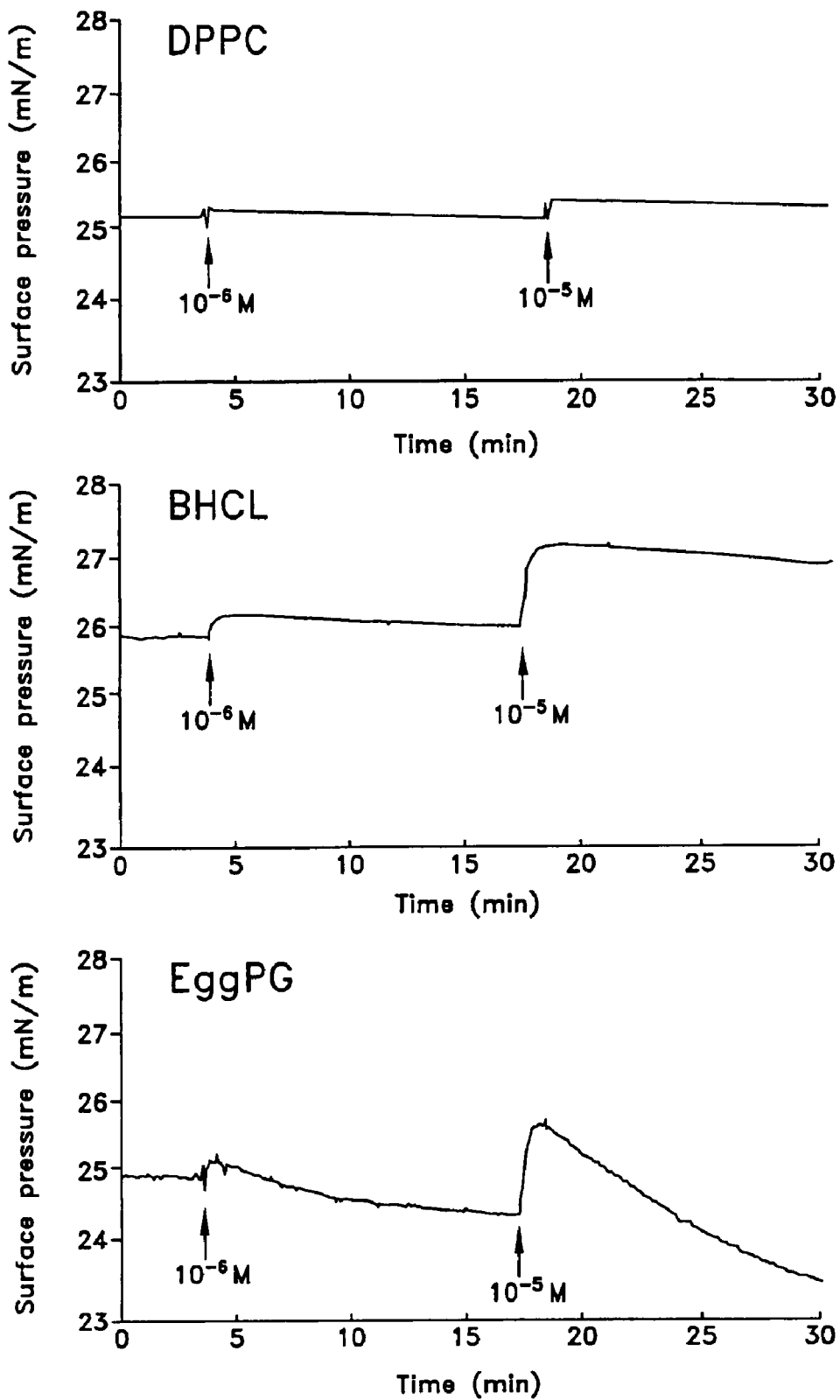
FIG. 8 shows the interaction of compound B and different lipid membranes showing the increase of surface pressure.

The interaction of N-[2-hydroxy-3-(1-piperidinyl)propoxy]-3-piridinecarboximidoyl chloride maleate with different phospholipids was tested by measuring the drug-induced surface pressure increase of lipid monolayers spread at the air-water interface (FIG. 8.). Monolayers in the present study have been formed from DPPC, EggPG and BHCL and increasing amount of N-[2-hydroxy-3-(1-piperidinyl)propoxy]-3-piridinecarboximidoyl chloride maleate was added in two concentrations ($10^{-6}$ M, $10^{-5}$ M) to the subphase. The addition of the drug underneath a lipid monolayer resulted in a surface pressure increase which was dependent on the concentration of N-[2-hydroxy-3-(1-piperidinyl)propoxy]-3-piridinecarboximidoyl chloride maleate in the subphase in all cases. There was, however, a prominent difference in the surface pressure profile of the different lipid monolayers. In case of zwitterionic DPPC, the pressure changed quickly after the injection of N-[2-hydroxy-3-(1-piperidinyl)propoxy]-3-piridinecarboxymidoyl chloride maleate, then it stayed at a constant level. By using mono layers containing the negatively charged BHCL the surface pressure profile showed a typical insertion kinetics, that is the pressure increased for about two minutes after which it reached an equilibrium level. In the presence of PG, the insertion kinetics of the drug was similar to that observed with BHCL, however, after reaching a certain value, the pressure started to decrease. The rate of pressure decrease was dependent on the concentration of the drug in the subphase. One possible explanation for this phenomena is the removal of N-[2-hydroxy-3-(1-piperidinyl)propoxy]-3-piridinecarboximidoyl chloride maleate-EggPG complexes from the interface since the decrease of pressure continued, even after reaching the initial pressure of the pure lipid monolayer.

To get further insight into the specific interaction of N-[2-hydroxy-3-(1-piperidinyl)propoxy]-3-piperidinyl) propoxy]-3-piridinecarboxymidoyl chloride maleate with lipid monolayers the drug induced surface pressure increase was measured at different initial surface pressure (FIG. 8.) The method of extrapolation to high initial surface pressure allows the estimation of limiting insertion pressures for the molecule, at which it is no longer able to insert into the monolayer. The extrapolated limiting initial surface pressures were 89 mN/m and 39 mN/m for BHCL and for DPPC, respectively. In case of monolayers containing the negatively charged BHCL, the pressure increases were always higher than those found for the zwitterionic DPPC by suggesting the importance of electrostatic interactions.

Our investigations serves with the first evidence that upon the administration of N-[2-hydroxy-3-(1-piperidinyl)propoxy]-3-piridinecarboximidoyl chloride maleate in a physiologically relevant concentrations, it is able to interact with lipid membranes, in a head-group specific manner.

Figure 9:
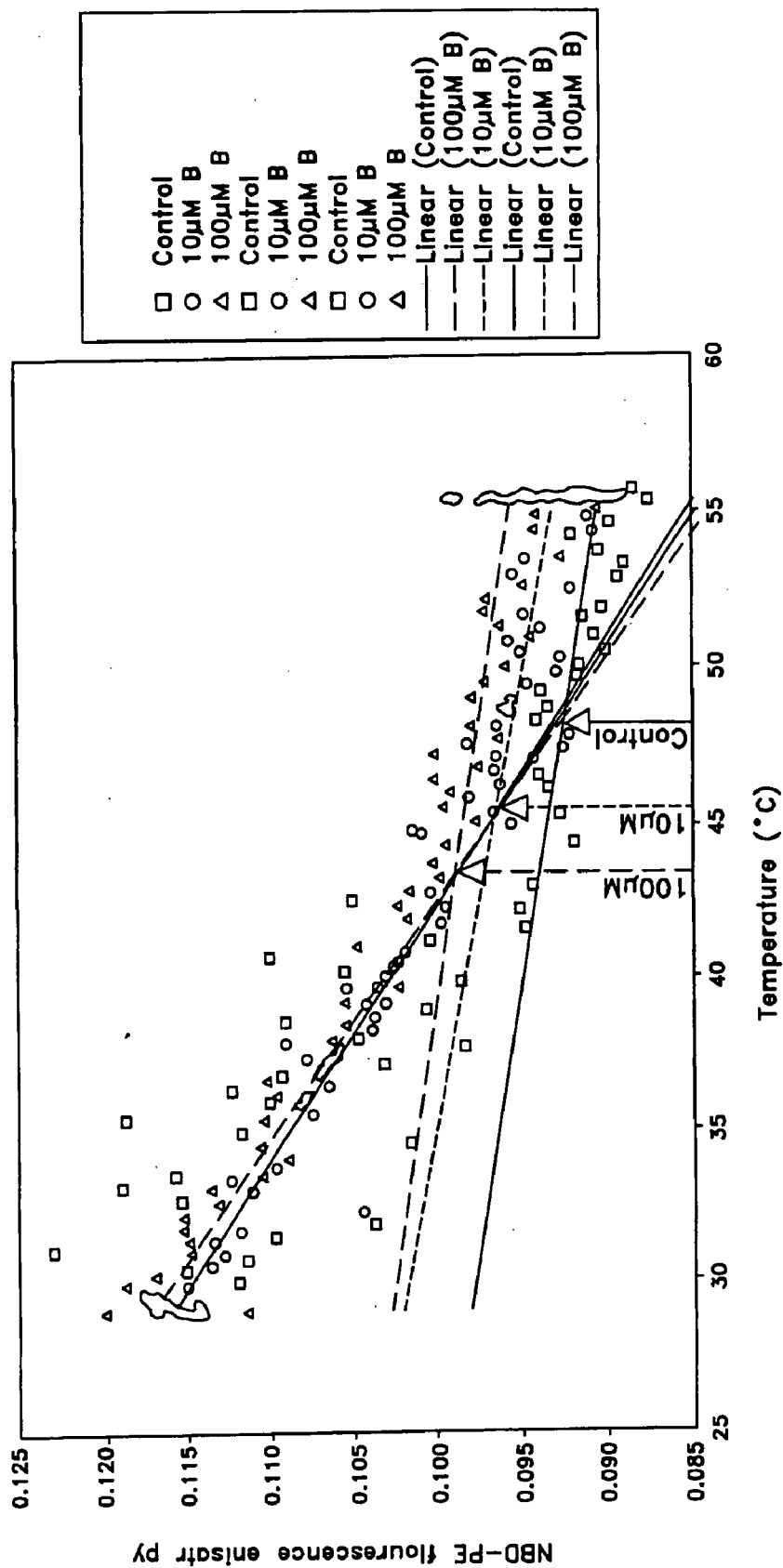
FIG. 9 shows the effect of compound B in the concentration of 10 mM and 100 mM on the bilayer $(L_a) \to T$ hexagonal $(H_{II})$ phase transfer of large unilamellar vesicles prepared from dipalmitoyl-phosphatidyl ethanolamine.

In FIG. 8. the interaction of N-[2-hydroxy-3-(1-piperidinyl)propoxy]-3-pyridine carboximidoyl chloride maleate (B) and the monomolecular lipid layers is shown. At the arrows N-[2-hydroxy-3-(1-piperidinyl)propoxy]-3-piridinecarboximidoyl chloride maleate was added to the subphase at the indicated concentrations. In FIG. 9. the surface pressure increase is presented after the injection of N-[2-hydroxy-3-(1-piperidinyl)propoxy]-3-piridinecarboxymidoyl chloride maleate (B) underneath monolayers of BHCL or DPPC at different initial pressures. The N-[2-hydroxy-3-(1-piperidinyl)propoxy]-3-piridinecarboximidoyl chloride maleate concentration in the subphase was 10 μmol. The linear regression analysis of the experimental data resulted in correlation coefficients of 0.844 and 0.995 for BHCL and DPPC monolayers respectively.

The Protective Effect of N-[2-hydroxy-3-(1-piperidinyl)propoxy]-3-piridinecarboximidoyl Chloride Maleate Against Cytotoxic Cytokines and Cycloheximide 1. Background The purpose of these studies was to investigate a possible connection between the production of cytokines and the pathophysiological changes N-[2-hydroxy-3-(1-piperidinyl)propoxy]-3-piridinecarboximidoyl chloride maleate seems to be protective against.

Our data suggest that N-[2-hydroxy-3-(1-piperidinyl)propoxy]-3-piridinecarboximidoyl chloride maleate is a cytoprotective agent for tissue cultured cells treated with cytotoxic cytokines. N-[2-hydroxy-3-(1-piperidinyl)propoxy]-3-piridinecarboximidoyl chloride maleate treatment increased the survival rate of TNF treated WEHI 164 (and other mammalian) cells. This effect was concentration dependent, but was not directly proportional to the drug concentration. The extent of protection provided by the N-[2-hydroxy-3-(1-piperidinyl)propoxy]-3-pyridine carboximidoyl chloride maleate treatment was variable from experiment to experiment, though the increased resistance of the treated cells to cytotoxic cytokines was clearly a tendency in all experiments. The protection provided by N-[2-hydroxy-3-(1-piperidinyl)propoxy]-3-pyridine carboxymidoyl chloride maleate treatment was not very high, however, in a living animal even this degree of protection could have been sufficient to moderate or prevent pathophysiological processes.

2. Aim of Study

Serum TNF levels and inducibility of macrophages from STZ diabetic and control animals were measured. LPS-induced serum TNF activities were significantly enhanced in STZ-induced diabetic rats (6-18 weeks of age) compared with those of non-diabetic rats, during the first month of diabetes.

3. Results

The mean serum TNF concentration (measured by radioimmunoassay) of the diabetic group was significantly higher (480±96 U/ml) than in healthy controls (345±48 U/ml). (Foss et al. 1992 Braz. J. Med. Biol. Res. 25, 239 reported similar results in human patients). Within the diabetic group, there was no correlation between serum TNF levels and duration of diabetes. We have not found biologically active TNF in the sera of diabetic animals by the cytotoxicity assay on L929 cells. The difference between the RIA and cytotoxicity measurements indicate the presence of high levels of soluble TNF receptor antagonists (a protective, anti-inflammatory molecule), suggesting the involvement of TNF in diabetic complications.

N-[2-hydroxy-3-(1-piperidinyl)propoxy]-3-piridinecarboximidoyl chloride maleate had an unexpected proliferative effect on yeast cells (and on different, cultured, normal, diploid animal or human cells). The influence of N-[2-hydroxy-3-(1-piperidinyl)propoxy]-3-pyridine carboximidoyl chloride maleate was especially impressive in the presence of low concentrations of the growth inhibitory antibiotic, cycloheximide. Yeast cell colonies grown in the presence of N-[2-hydroxy-3-(1-piperidinyl)propoxy]-3-piridinecarboximidoyl chloride maleate and cycloheximide did not show an increased incidence of genetic changes (antibiotic resistant mutations), only higher metabolic resistance against the inhibitory effect of cycloheximide on protein synthesis.

According to our measurements the effects of N-[2-hydroxy-3-(1-piperidinyl)propoxy]-3-piridinecarboximidoyl chloride maleate can be traced down to the increased activity of the AP-1 transcription factor, which mediates the effects of both mitogenic factors and different types of stress. The results also indicate that the above test compound and similar compounds influence the detixity of AP-1 and possibly other transcription factors by maintaining the effects of growth factors and metabolic stress conditions.

Figure 10:
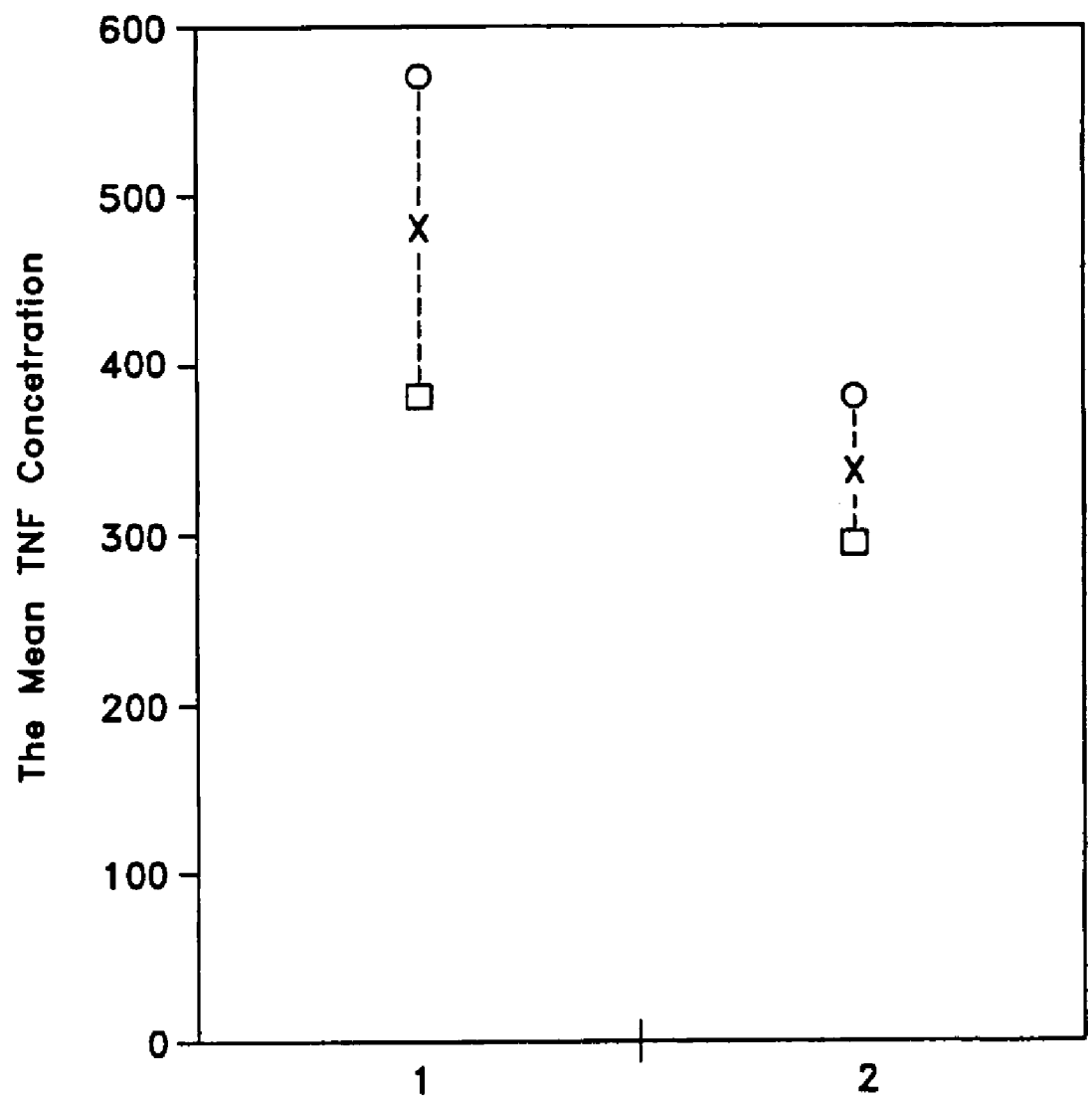
FIG. 10 is the diagram of the effect of compound B on the serum TNF level in healthy and STZ diabetic rats.
Figure 11:
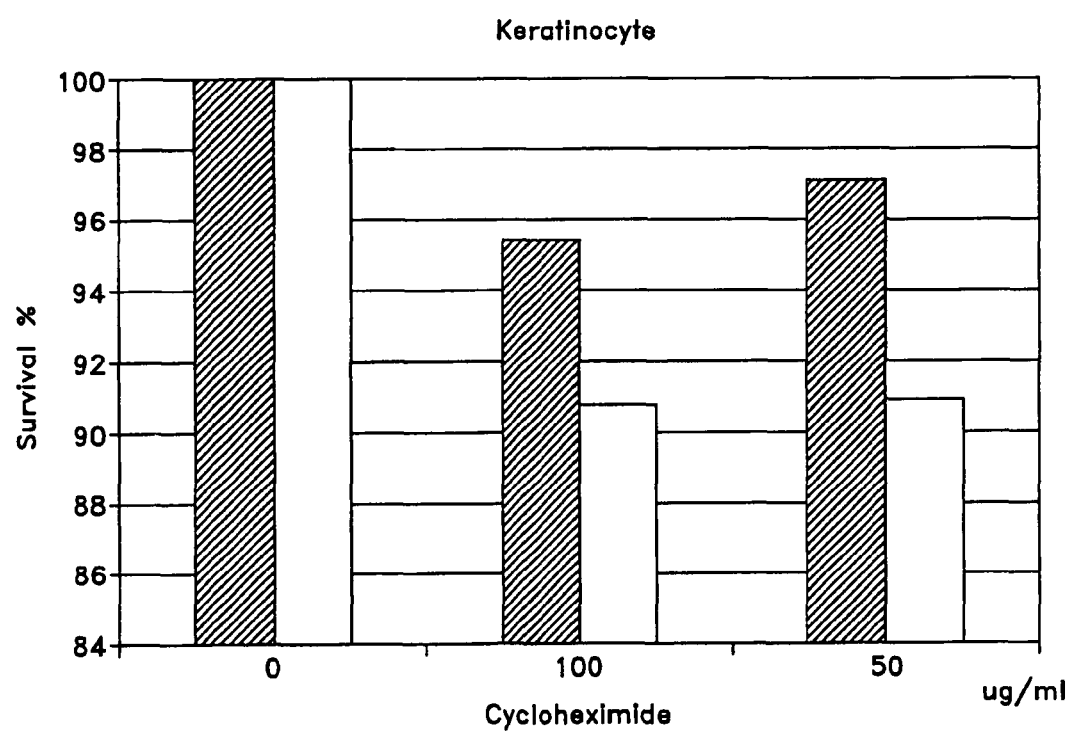
FIG. 11 shows the effect of compound B against the growth inhibiting effect of keratinocyte cyclohexylimide.
Figure 12:
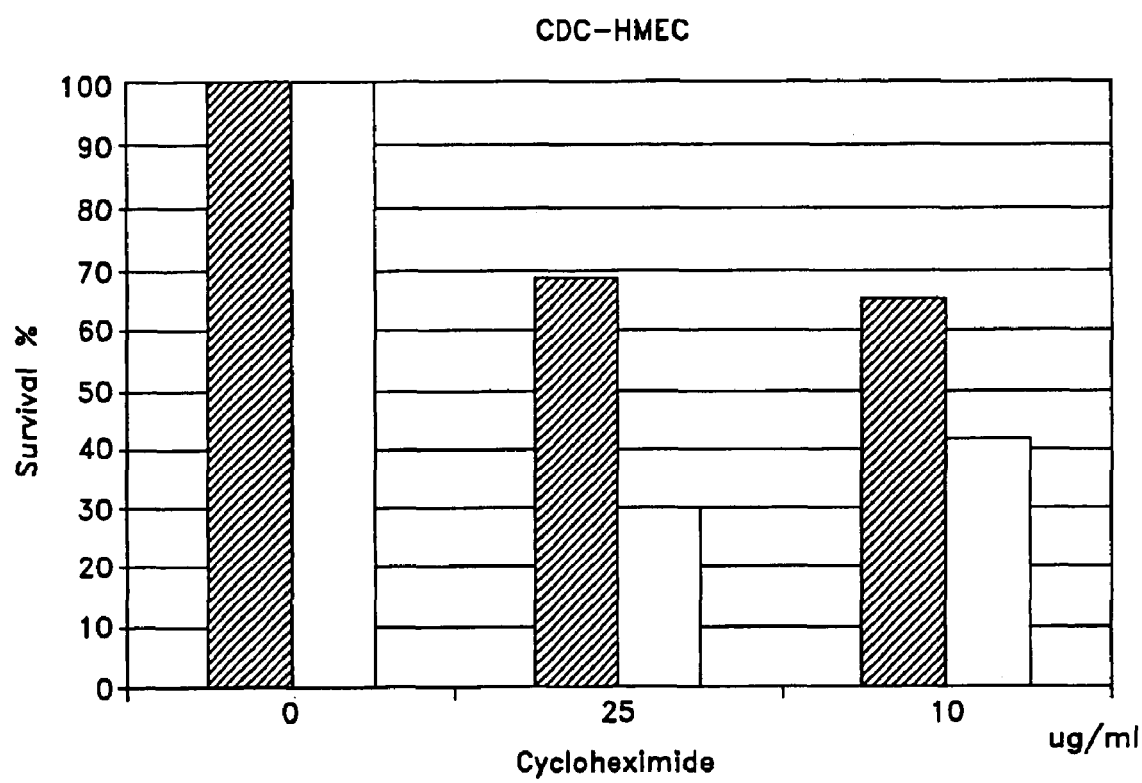
FIG. 12 shows the effect of compound B against the cell damaging effect of cycloheximide on endothelial cells.
Figure 13:
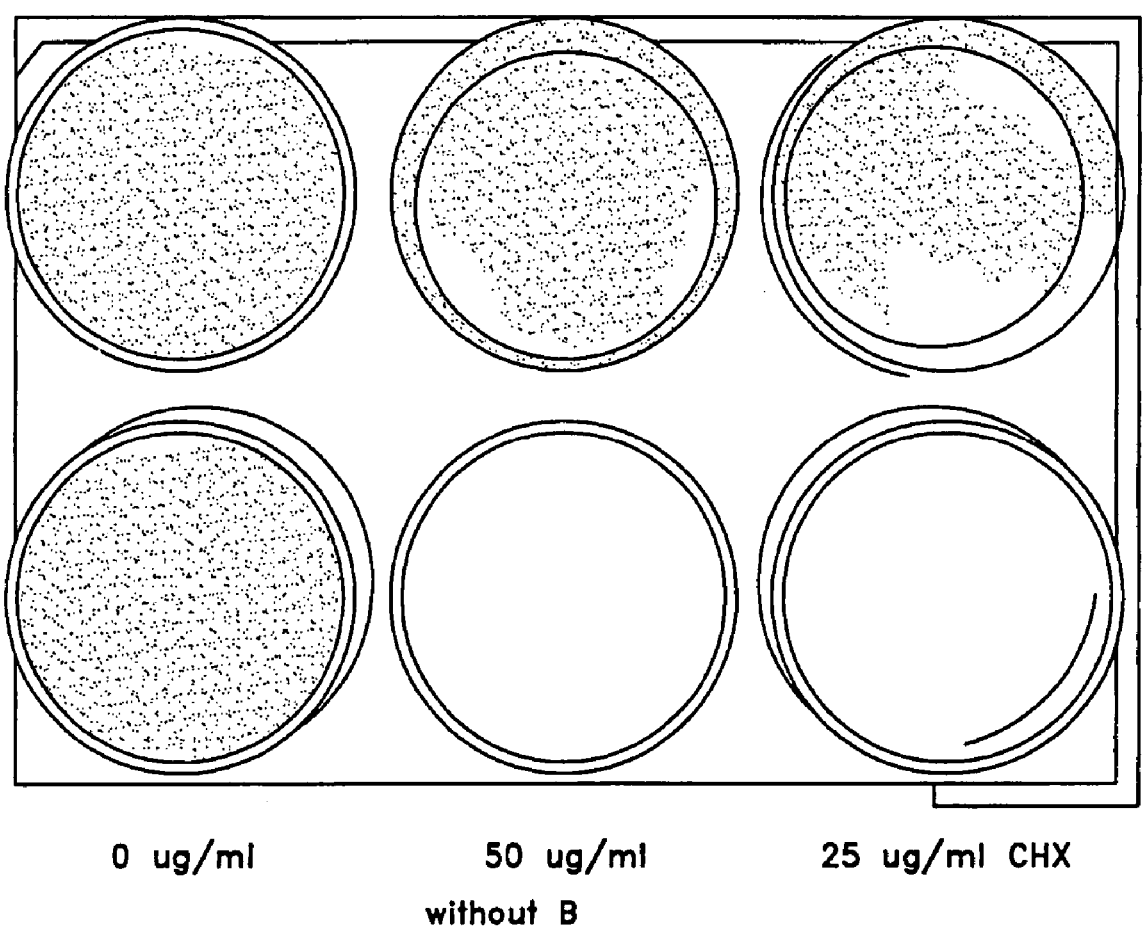
FIG. 13 shows the cytoprotective effect of compound B against the cell damaging effect of cycloheximide on HeLa cell line.
Figure 14:
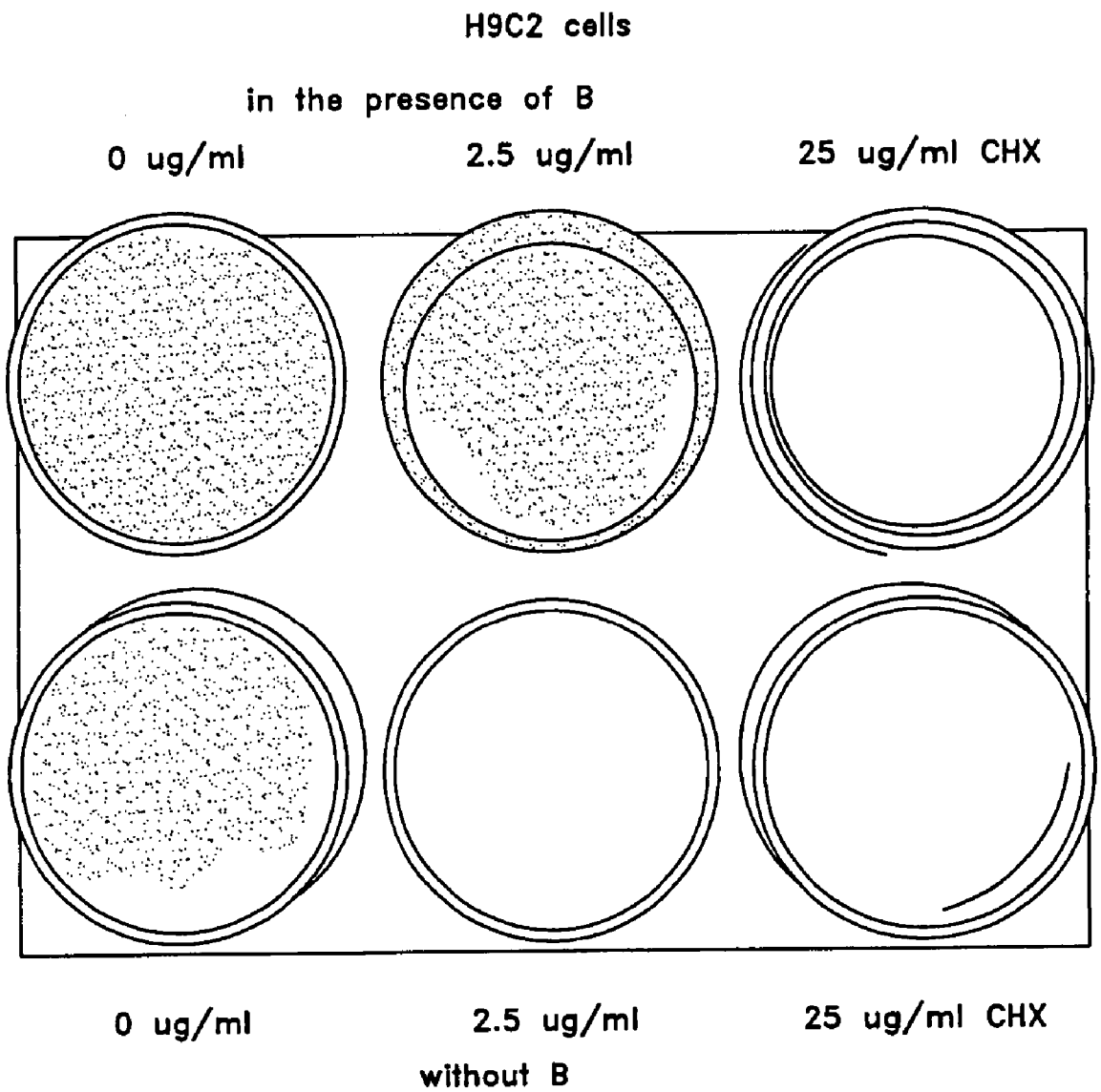
FIG. 14 shows the effect of compound B against the growth inhibiting effect of cyclohexylimide on H9c2 rat myocardium cell line.
Figure 15:
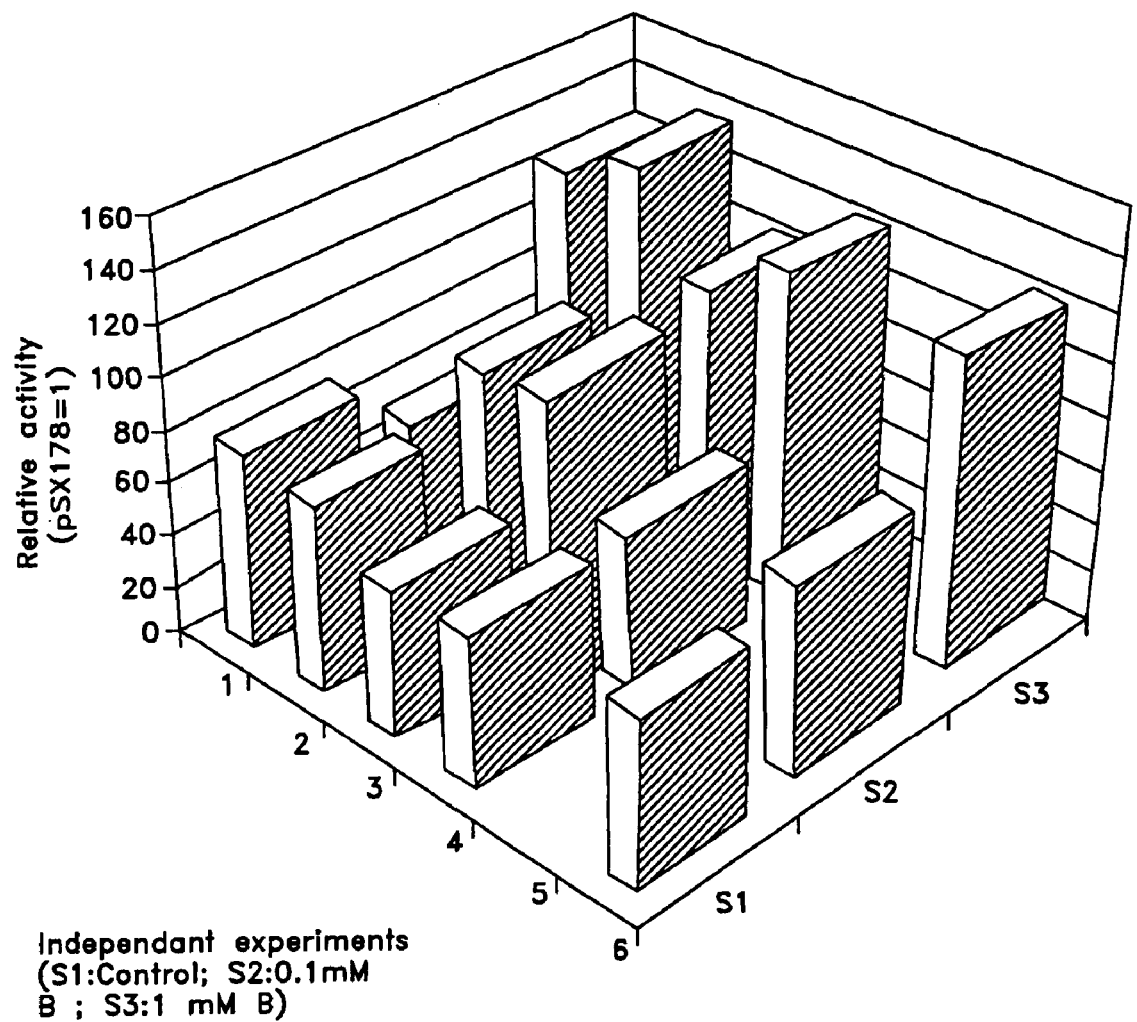
FIG. 15 shows the effect of compound B on the PI transcription factor activity in AB 1380 yeast cells.
Figure 16:
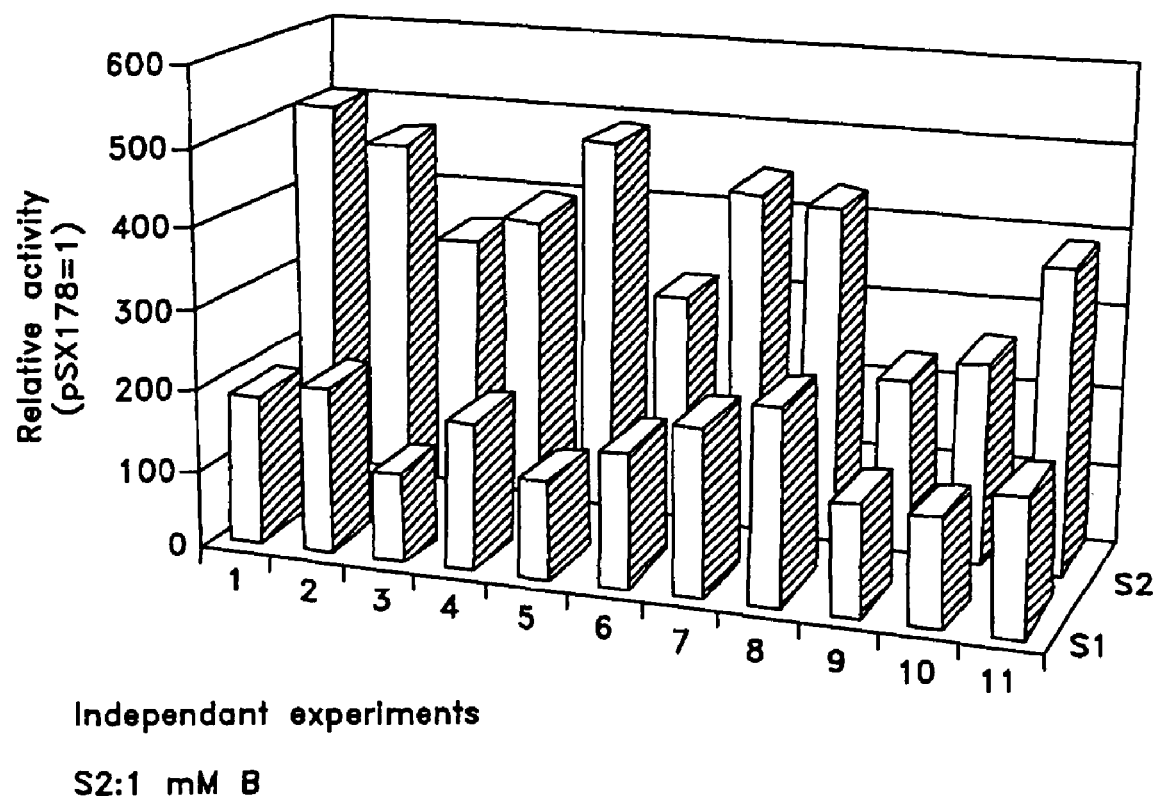
FIG. 16 shows the effect of compound B on the AP 1 transcription factor activity in JF1 yeast cells.
Figure 17:
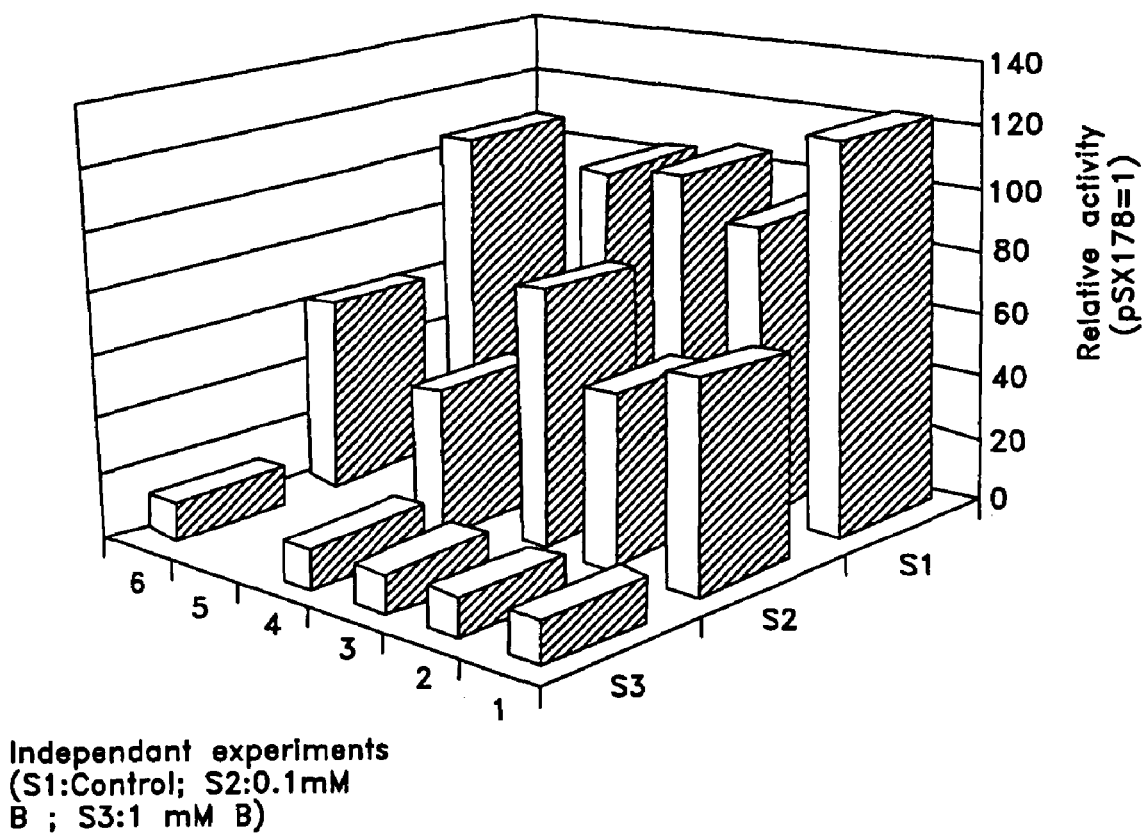
FIG. 17 shows the effect of compound B on the P1 transcription factor activity in AB 1380 yeast cells.

In FIG. 10. LPS induced TNF production in vitro of macrophages isolated from STZ diabetic (1) and normal (2) animals, in FIG. 11. the N-[2-hydroxy-3-(1-piperidinyl)propoxy]-3-piridinecarboximidoyl chloride maleate induced protection of keratinocytes against the growth inhibitory effect of cycloheximide, in FIG. 12. the N-[2-hydroxy-3-(1-piperidinyl)propoxy]-3-piridinecarboximidoyl chloride maleate (B) induced protection of cells (endothelial cells) against toxic effects of cycloheximide, in FIG. 13. N-[2-hydroxy-3-(1-piperidinyl)propoxy]-3-pyridine carboximidoyl chloride maleate (B) protection of human cervical HeLa cells against the growth inhibitory effect of the antibiotic cycloheximide, in FIG. 14. the N-[2-hydroxy-3-(1-piperidinyl)propoxy]3-piridinecarboximidoyl chloride maleate (B) induced protection of heart muscle cells against the growth inhibitory effect of the antibiotic cycloheximide, and in FIG. 15. the effect of N-[2-hydroxy-3-(1-piperidinyl)propoxy]-3-piridinecarboximidoyl chloride maleate (B) on P1 transcription factor activity in AB1380 yeast cells are demonstrated. Row 6. represents the mean values. Row 5. is empty. In FIG. 16. the effect of N-[2-hydroxy-3-(1-piperidinyl)propoxy]-3-piridinecarboximidoyl chloride maleate on AP1 transcription factor activity in JF1 yeast cells are demonstrated. Row 11. represents the mean values. In FIG. 17. the effect of N-[2-hydroxy-3-(1-piperidinyl)propoxy]-3-piridinecarboximidoyl chloride maleate (B) on P1 transcription factor activity in AB1380 yeast cells are demonstrated. Row 6. represents the mean values. Row 5. is empty.

Cardioprotective Effects of N-[hydroxy-3-(1-piperidinyl)propoxy]-3-piridinecarboximidoyl Chloride Maleate in Isolated Rat Hearts

1.

The objective of the study was to investigate the cardioprotective and antiarrhythmic effect of N-[2-hydroxy-3-(1-piperidinyl)propoxy]-3-piridinecarboximidoyl chloride maleate in isolated working rat hearts.

2. Methods

After a 10-min. aerobic working perfusion, hearts (n=10 in each group) were subjected to a 10-min. coronary occlusion followed by a 3-min. reperfusion in the presence of 0.05, 0.5, 5.0, 20.0, and 50 mg/L N-[2-hydroxy-3-(1-piperidinyl)propoxy]-3-pyridine carboximidoyl chloride maleate, respectively.

In the further studies rats were pretreated with the most effective (20 mg/kg) dose of N-[2-hydroxy-3-(1-piperidinyl) propoxy]-3-piridinecarboximidoyl chloride maleate, one and five hours before isolation of the hearts, respectively. After excision of the hearts, they were subjected to the coronary occlusion protocol detailed above while perfused in presence/absence of 20 mg/l N-[2-hydroxy-3-(1-piperidinyl)propoxy]-3-piridinecarboximidoyl chloride maleate.

In separate experiments the effects of heat stress, ischemia, N-[2-hydroxy-3-(1-piperidinyl)propoxy]-3-pyridine carboximidoyl chloride maleate and their combination were studied on myocardial HSP-70 protein content. Isolated hearts were subjected to 15 min. heat-stress (42° C.), global normothermic ischemia, and N-[2-hydroxy-3-hydroxy-3-(1-piperidinyl)propoxy]-3-pyridine carboximidoyl chloride maleate perfusion followed by 120 and 180 min. reperfusion, respectively.

3. Results

Before ischemia, N-[2-hydroxy-3-(1-piperidinyl)propoxy]-3-piridinecarboximidoyl chloride maleate increased coronary flow (CF) with a bell-shaped concentration-response relationship. Other cardiac functional parameters were not changed by lower concentrations of the drug. N-[2-hydroxy-3-(1-piperidinyl)propoxy]3-piridinecarboximidoyl chloride maleate at 50 mg/L caused significant bradycardia, a reduction in aortic flow (AF) and +dP/dt$_{max}$, and an increase in left ventricular end-diastolic pressure (LVEDP) before ischemia. In the control group, coronary occlusion markedly decreased CF, AF, +/−dP/dt$_{max}$, and increased LVEDP. N-[2-hydroxy-3-(1-piperidinyl)propoxy]-3-piridinecarboximidoyl chloride maleate alleviated ischemia-induced deterioration of cardiac function with a bell-shaped concentration-response relationship. The concentration of 20 mg/L N-[2-hydroxy-3-(1-piperidinyl)propoxy]-3-piridinecarboximidoyl chloride maleate showed the most pronounced anti-ischemic effect. Reperfusion after 10 min. coronary occlusion triggered ventricular fibrillation (V F) in all hearts of the control group. Higher concentrations of N-[2-hydroxy-3-(1-piperidinyl) propoxy]-3-piridinecarboximidoyl chloride maleate resulted in a dose-dependent antiarrhythmic effect.

After one hour pretreatment N-[2-hydroxy-3-(1-piperidinyl)propoxy]-3-pyridine carboximidoyl chloride maleate still afforded cardioprotection, and potentiated the acute effects of the compound. Five hours after pretreatment, the cardioprotective effect was not observable, however, some of the acute effects of N-[2-hydroxy-3-(1-piperidinyl)propoxy]-3-pyridine carboximidoyl chloride maleate perfusion were increased.

The compound alone did not increase myocardial HSP-70 content. Stetyocardial HSP-70 content was markedly elevated due to heat stress, however, ischemia resulted in a mild HSP-70 elevation. Nevertheless, when ischemia was induced in the presence of 20 mg/l N-[2-hydroxy-3-(1-piperidinyl)propoxy]-3-piridinecarboximidoyl chloride maleate, HSP-70 content was increased to approximately the same level as found after heat stress.

We conclude that N-[2-hydroxy-3-(1-piperidinyl)propoxy]-3-piridinecarboximidoyl chloride maleate exerts an anti-ischemic, and an antiarrhythmic effect. The concentration of 20 mg/L was found to produce both marked anti-ischemic and antiarrhythmic effect in the isolated rat heart. When the direct anti-ischemic effect of the drug disappears after one hour, it still increases the degree of protection afforded by acute N-[2-hydroxy-3-(1-piperidinyl)propoxy]-3-pyridine carboximidoyl chloride maleate treatment. N-[2-hydroxy-3-(1-piperidinyl)propoxy]-3-pyridine carboximidoyl chloride maleate and ischemic stress together induces a rapid de novo synthesis of HSP-70 in the rat heart. N-[2-hydroxy-3-(1-piperidinyl)propoxy]-3-piridinecarboximidoyl chloride maleate alone does not affect HSP-70 synthesis.

Figure 19:
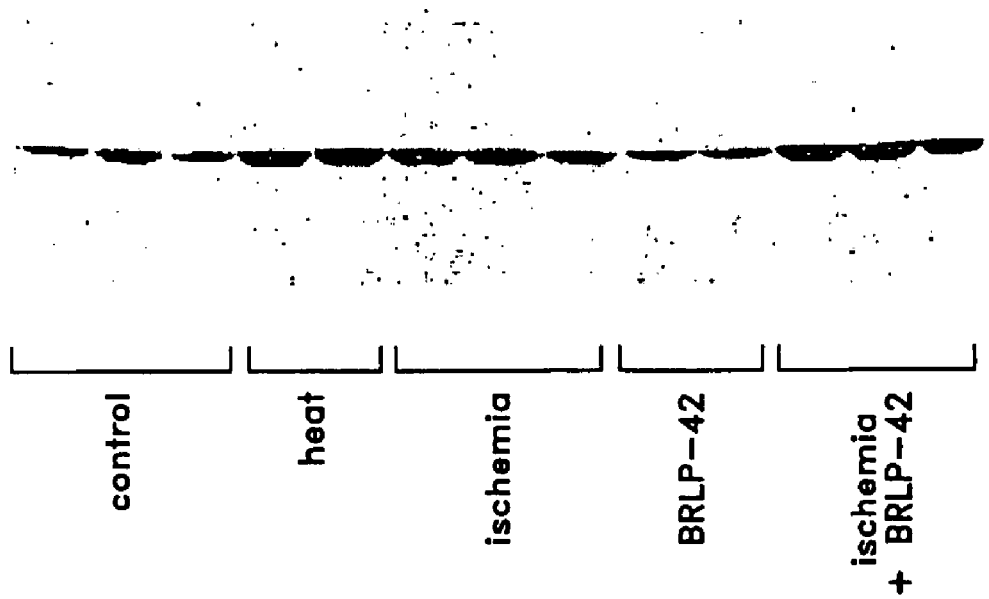
FIG. 19 shows the test results obtained on isolated functioning ischemic rat heart model wherein the model was treated with compound B, determined by Western blotting 3 hours after ischemia.
Figure 18:
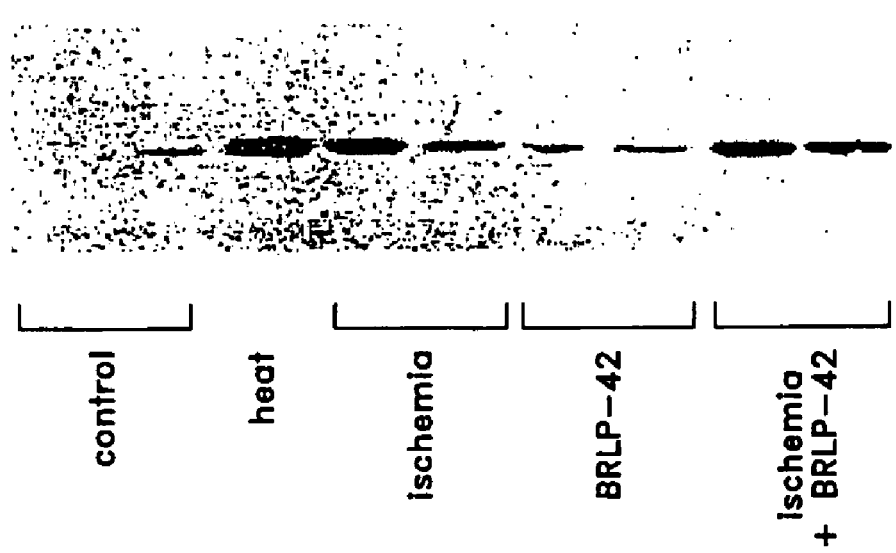
FIG. 18 shows the test results obtained on isolated functioning ischemic rat heart model wherein the model was treated with compound B, determined by Western blotting 2 hours after ischemia.

In FIGS. 18-19, the hsp protein levels, determined by Western blotting are demonstrated from control, heat shocked, item treated, the N-[2-hydroxy-3-(1-piperidinyl)propoxy]-3-piridinecarboximidoyl chloride maleate treated (B) and ischemia+hydroxy-3-(1-piperidinyl)propoxy]-3-pyridine carboximidoyl chloride maleate treated (Ischemia+B) rats followed by 2 (FIG. 18.) or 3 hours (FIG. 19) recovery.

Caperone-Booster N-[2-hydroxy-3-(1-piperidinyl) propoxy]-3-piridinecarboximidoyl Chloride Maleate in Prevention and Repair of Skin Damages: Ultraviolet Light B Protection in Human Skin Grafted Severe Combined Immunodeficiency Disease Mice and Accelerated Wound Healing in Diabetic Rat 1. Background Hsps appear to play a general role in the physiological protection of the skin from environmental stress. As molecular chaperones they participate in prevention and repair of damages caused by various exposures, such as mechanical trauma, light, heat and chemical injuries, infections, etc. (E. V. Maytin, JID 104:448, 1995.) In pathological conditions, such as diabetes mellitus attenuated function of certain hsps has been reported (M. Cherian and E. C. Abraham, Biochem. Biophys. Res. Com. 212:184, 1995). Since N-2[hydroxy-3-(1-piperidinyl)propoxy]-3-piridinecarboximidoyl chloride maleate was shown to act as a chaperon booster (Vigh et al., in preparation) we would expect that the drug is able to enhance most various protection and repair mechanisms.

The purpose of this study was to test the effect of systemic (i) and topical (ii) administration of N-[2-hydroxy-3-(1-piperidinyl)propoxy]-3-piridinecarboximidoyl chloride maleate:

(i) in protection against UVB light induced skin injury in human skin grafted on severe combined immunodeficiency disease (SCID) mice,
(ii) in repair of destroyed wound healing process in STZ-diabetic rats.

2. Methods (i) Human skin transplanted SCID mice treated by N-[2-hydroxy-3-(1-piperidinyl)propoxy]-3-piridinecarboximidoyl chloride maleate (5.0 mg/kg i.p.) or vehicle were exposed to UVB light (100 mJ/cm$^2$). After 24 h skin biopsies were taken for histological examination and for hsp72 determination using immunohistological and Western blotting techniques. Pretreatment with N-[2-hydroxy-3-(1-piperidinyl)propoxy]-3-piridinecarboximidoyl chloride maleate prevented UVB light induced skin injury determined clinically and histologically. Intensive hsp72 staining of linear basement membrane could be observed by immunofluorescence technique and increased amount of hsp72 was measured by Western blotting of N-[2-hydroxy-3-(1-piperidinyl)propoxy]-3-piridinecarboximidoyl chloride maleate treated skin samples.

(ii) Streptozotocin-induced diabetic (STZ) rats with partial-to full thickness thermal wounds created on bilateral thoracic depilated skin by electroheating probe (3 mm of diameter; 60° C.; for 30, 60 and 90 sec.), treated by topical application of 1%, 2% or 4% N-[2-hydroxy-3-(1-piperidinyl)propoxy]-3-piridinecarboximidoyl chloride maleate containing cream or vehicle were used to determine the wound healing in form of self-control, side to side comparison. Wound closure was recorded photographically and using the digital epiluminescence microscopic technique. Wound areas were measured by planimetry 48 h and 21 days after heat injury. Level of hsp72 of skin biopsy samples was determined using Western blot analysis.

3. Results

Treatment with 4% N-[2-hydroxy-3-(1-piperidinyl)propoxy]-3-piridinecarboximidoyl chloride maleate containing cream significantly (p<0.10) accelerated wound closure and elevated the hsp72 level in skin biopsy samples compared to vehicle control.

Our results lead to the conclusion that the administration of N-[2-hydroxy-3-(1-piperidinyl)propoxy]-3-piridinecarboximidoyl chloride maleate provides protection against injuries from UV exposure and has potential therapeutic applications for the clinical treatment of conditions with defect in wound repair or after surgical intervention.

Figure 20:
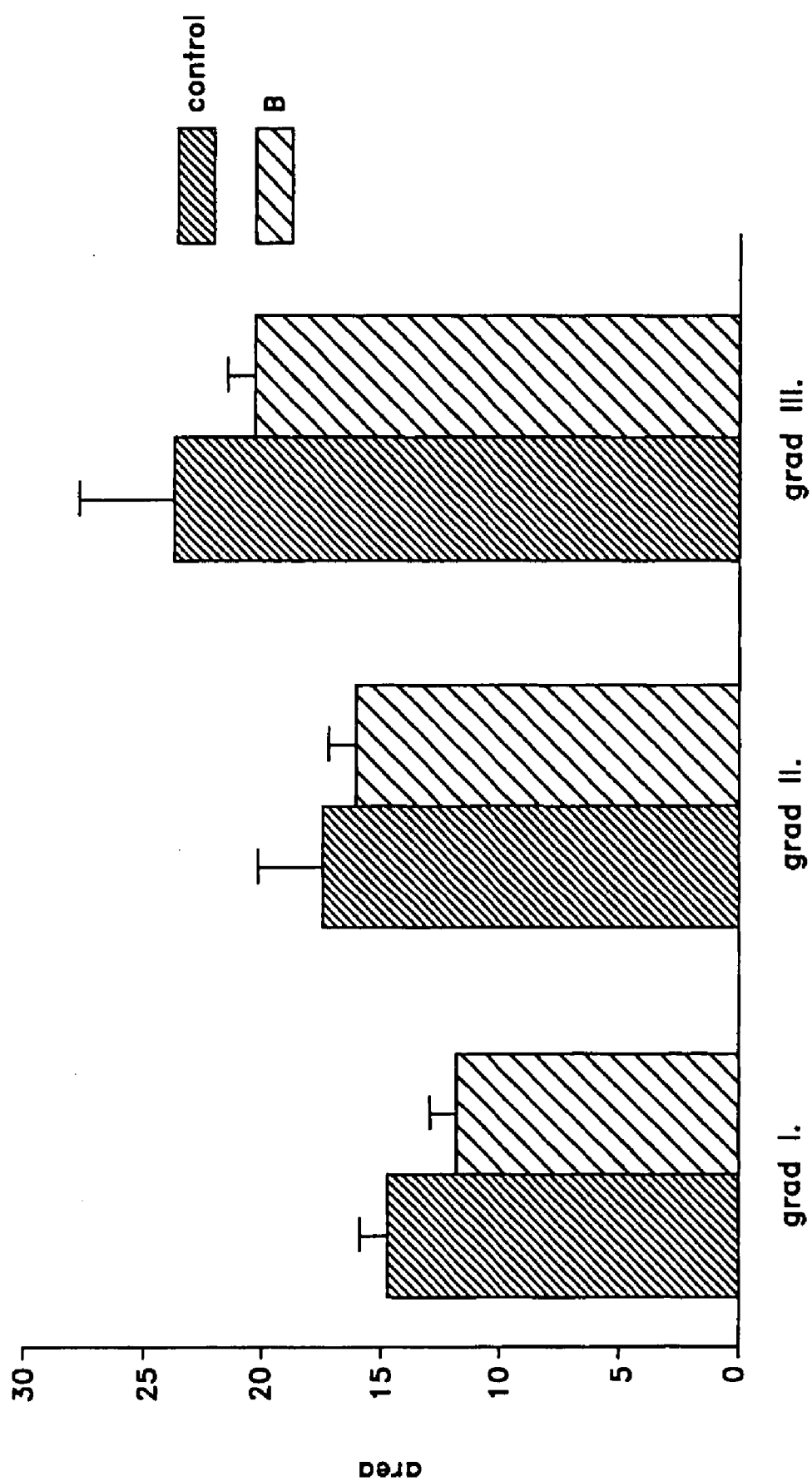
FIG. 20 shows the wound healing on STZ diabetic rats after heat injury by treatment of cream containing 1% compound B.
Figure 21:
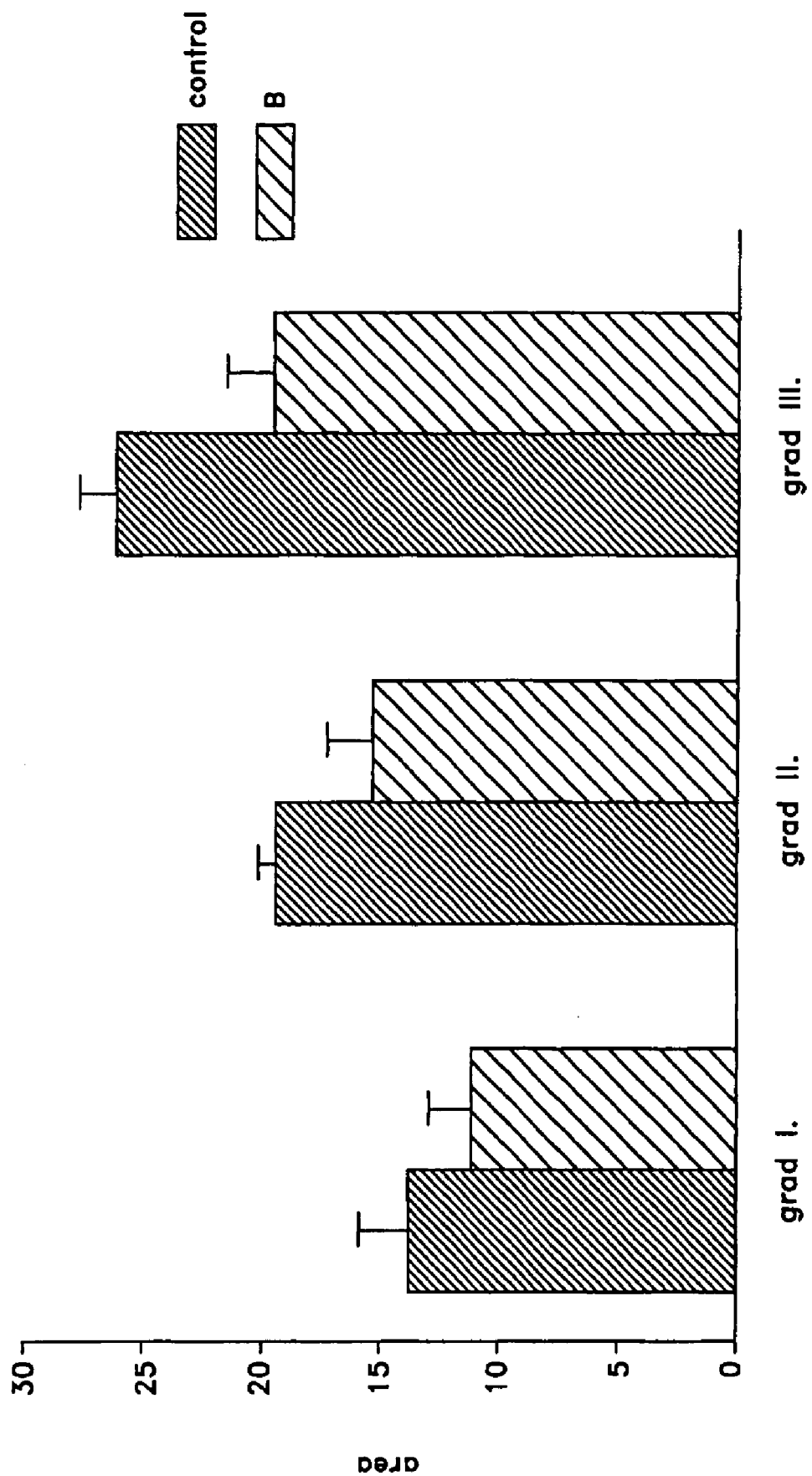
FIG. 21 shows the wound healing on STZ diabetic rats after heat injury by treatment of cream containing 2% compound B.
Figure 22:
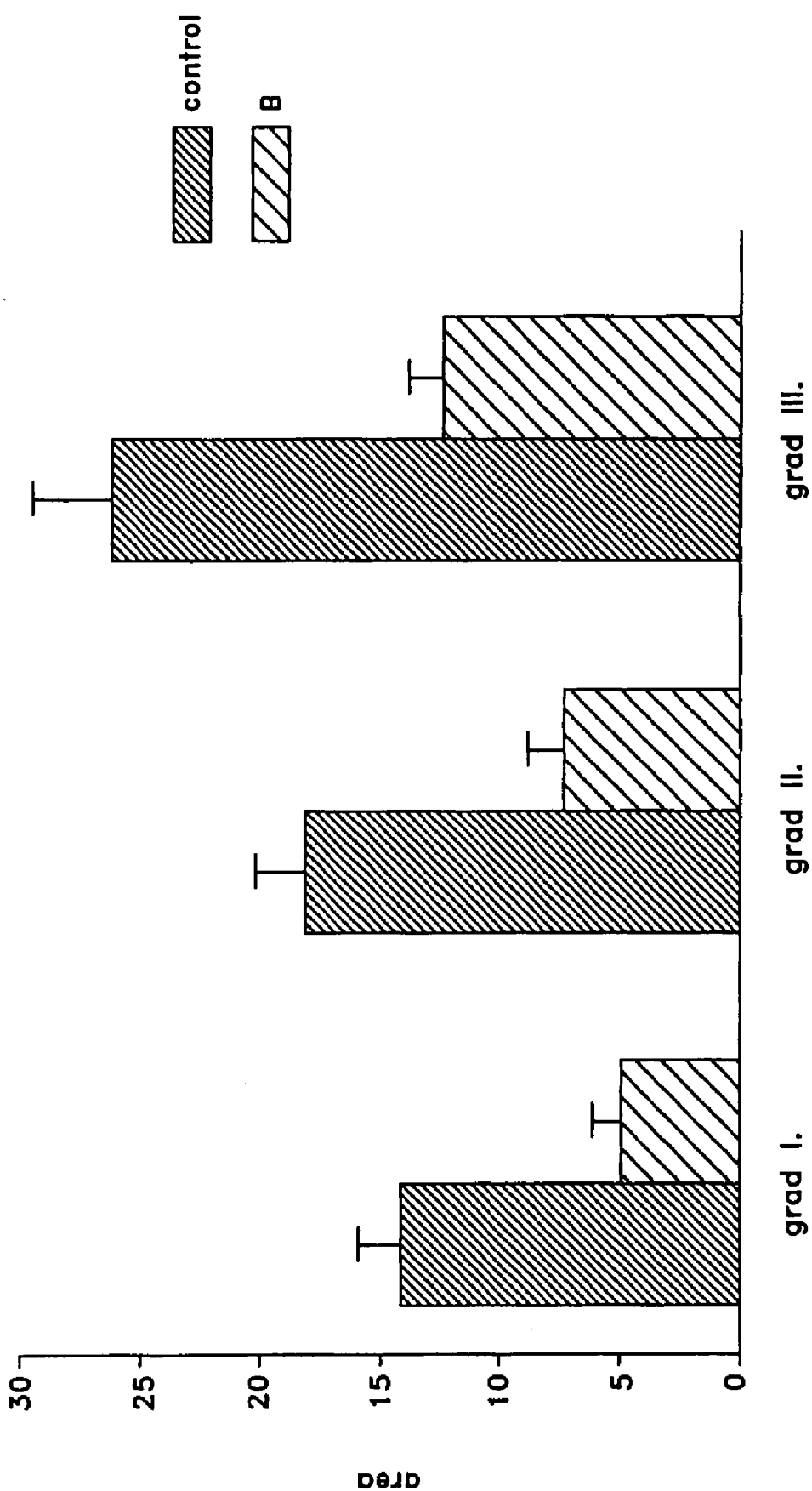
FIG. 22 shows the wound healing on STZ diabetic rats after heat injury by treatment of cream containing 4% compound B.
Figure 23:
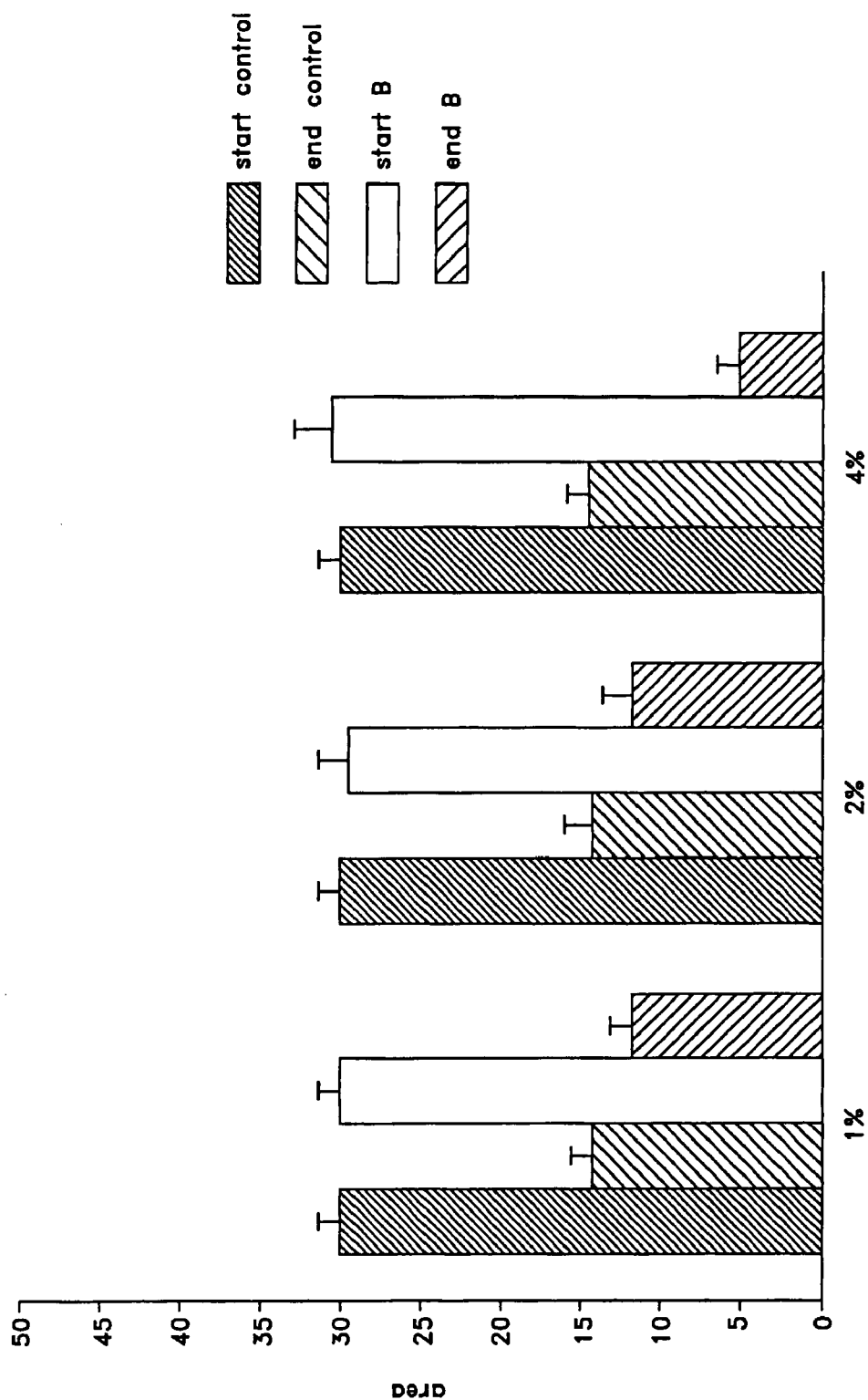
FIG. 23 shows the wound healing on STZ diabetic rats after heat injury by treatment of cream containing 1% compound B, but evaluated visually.
Figure 24:
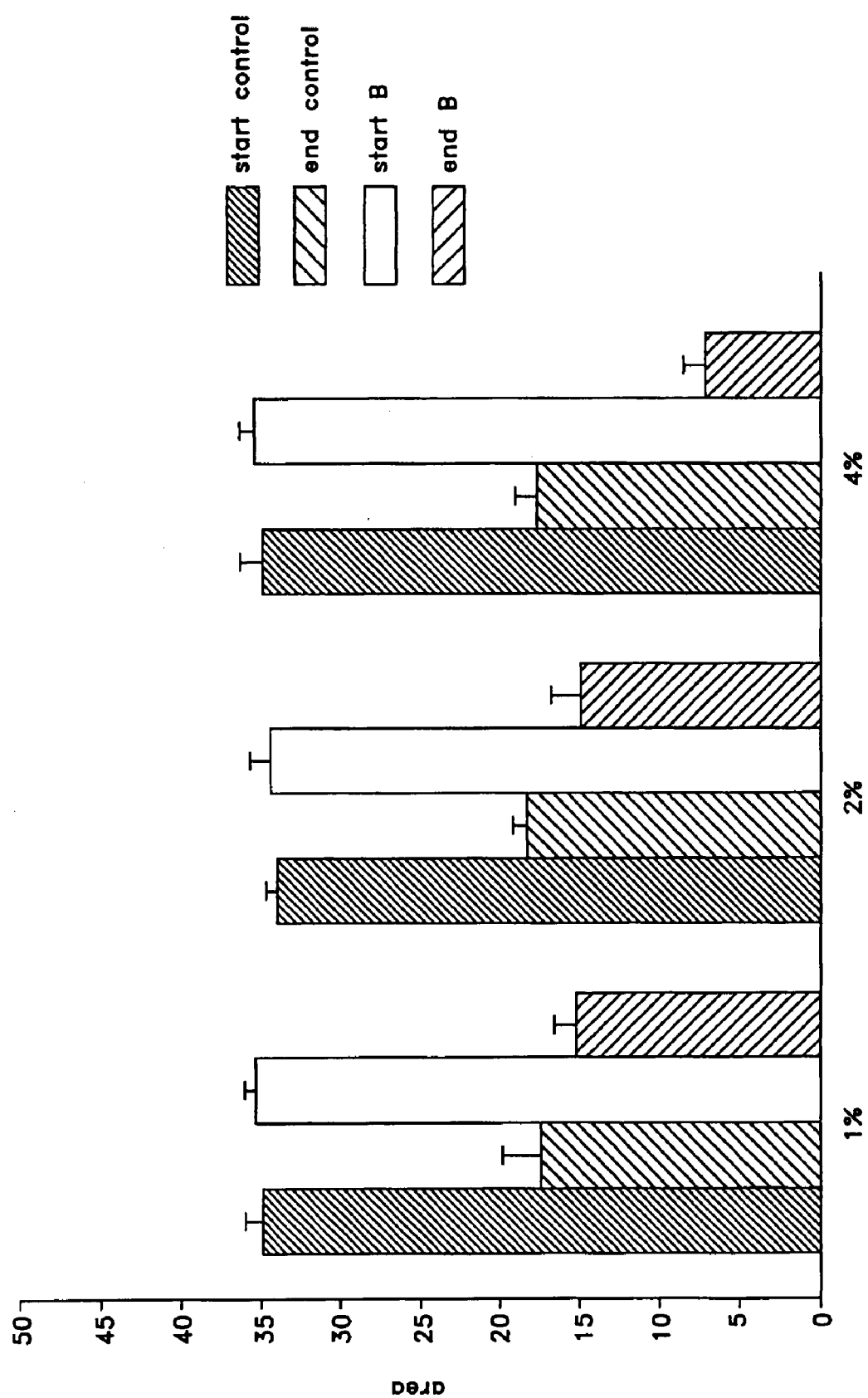
FIG. 24 shows the wound healing on STZ diabetic rats after heat injury by treatment of cream containing 2% compound B, but evaluated visually.
Figure 25:
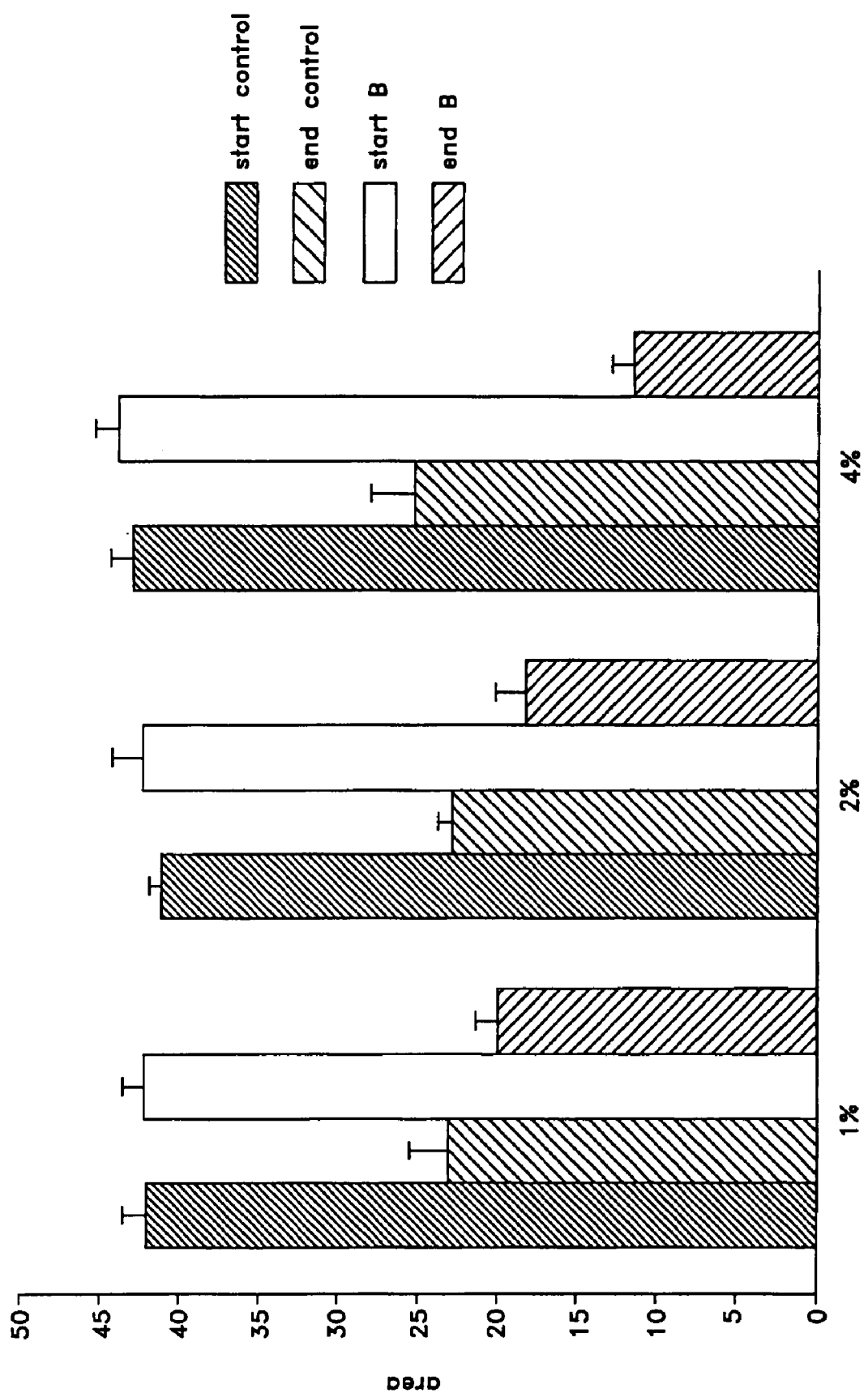
FIG. 25 shows the wound healing on STZ diabetic rats after heat injury by treatment of cream containing 4% compound B, but evaluated visually.

On FIG. 20, 21, 22 the effect of 1%, 2%, 4% N-[2-hydroxy-3-(1-piperidinyl)propoxy]-3-carboximidoyl chloride maleate (B) containing cream are demonstrated on wound healing. On FIG. 23, 24, 25 the results are shown according to the grade of wounds.

Figure 26:
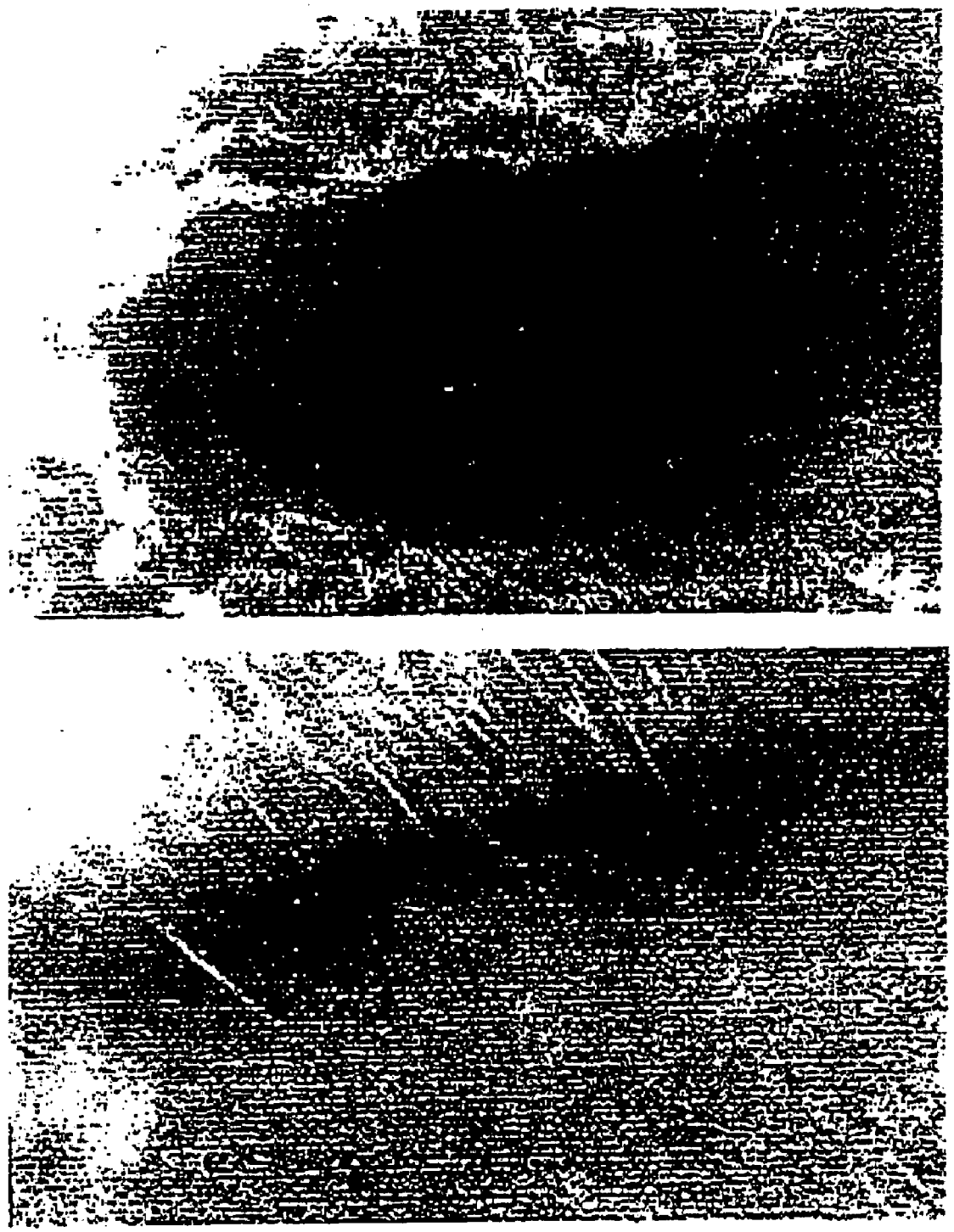
FIG. 26 shows the comparison photographs (treated and control) made in the above tests by digital epiluminescence microscopic technique.

On FIG. 26. the photographic pictures of untreated and N-[2-hydroxy-3-(1-piperidinyl)propoxy]-3-pyridinecarboximidoyl chloride maleate (B) treated wounds are shown.

Figure 27:
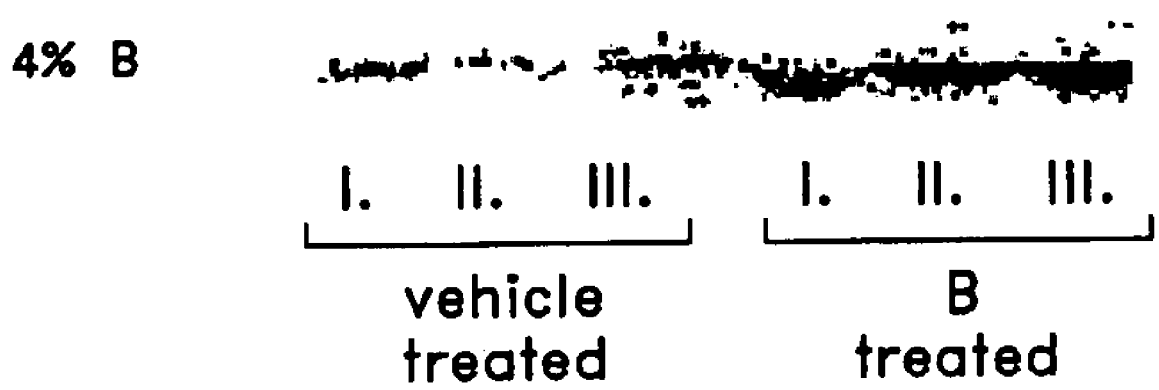
FIG. 27 shows the hsp72 level of the samples obtained in the previous tests determined by Western blotting at the treatments with creams containing 1, 2 and 4% compound B.

FIG. 27. shows the hsp72 protein levels of bioxy specimens from control N-[2-hydroxy-3-(1-piperidinyl)propoxy]-3-piridinecarboximidoyl chloride maleate (B) (1%, 2% and 4%) treated wounds.

Figure 28:
FIG. 28 shows the hsp72 levels determined by immunohistochemical analysis (treated and control) on SCID mice exposed to UV-B ray and treated with compound B.
Figure 28:

On FIG. 28 the immunhistochemical evaluation of hsp72 protein after N-[2-hydroxy-3-(1-piperidinyl)propoxy]piridinecarboximidoyl chloride maleate (B) treatment is shown.

Figure 29:
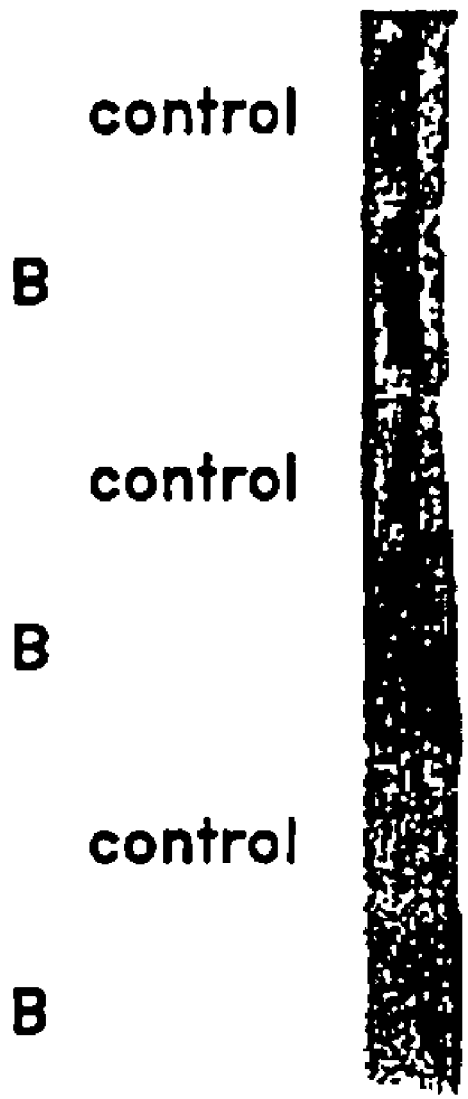
FIG. 29 shows the hsp72 levels determined by Western blotting on SCID mice skin biopsy samples exposed to UV-B ray and treated with compound B.

On FIG. 29. the hsp72 levels from N-[2-hydroxy-3-(1-piperidinyl)propoxy]-3-pyridine carboximidoyl chloride maleate (B) treated and untreated (Control) skin samples of SCID mice are demonstrated.

Evaluation of Stimulatory Effect of Hydroxylamine Derivatives, According to the Invention on HSP72 Expression in Cells Exposed to Stresses a.) Cell Culture Conditions From the applied cells the 3T3 and L-929 mouse fibroblasts were cultured in MEM medium and grew in monolayer, the U-937 human leukemia cells were maintained in RPMI-1640 medium, in suspension culture, while the HeLa human epithelial cells were cultured in DMEM medium and in monolayer form. Cell cultures were maintained as described in example 6.2 (a) with the difference that cells were cultured in the above mentioned culture mediums.

b.) Conditions of the Experiments

Experiments were carried out applying stress before and after the drug treatment. Stress was provoked by heat, by chemical agent, $HgCl_2$ treatment. The test compounds were applied in the treatments at the $10^{-5}$ M concentration.

Cytotoxicity studies, which were performed by a 3 days assay, and were evaluated by MTT (Cytotechnology 11:49-58) indicated that all of the test compounds had a 50% growth inhibitory effect at a concentration larger than $10^{-4}$ M. Consequently, the concentration used in HSP72 studies has no significant cytotoxic effect.

1. Experiments with Heat Stress

These experiment were performed on 3T3 and L-929 mouse fibroblast cells furthermore on U-937 human leukemia cells.

The experiments on 3T3 cell applying heat stress were performed as described in the 6.2. (c) point of example 6, with the difference that stress was induced by a 30 min. exposure at 43° C. temperature and treatment with the test compounds was performed 15 min. before or 100 min. after the heat stress.

Immunodetection was carried out using the HSP72 specific SPA 810 (StressGene) primary and the horse-radish peroxidase conjugated A9044 (Sigma) secondary antibodies. Densitometric evaluation was performed by a LKB Ultrascan XL densitometer.

Results are summarized in Table 2 and Table 3.

TABLE 2

Stimulatory effect of hydroxylamine-derivatives by the invention on the heat stress induced HSP72 production in 3T3 cells if treatment precedes stress exposure.

| Compounds | HSP72 level relative to the stress exposed control |
|---|---|
| N-[2-hydroxy-3-(1-piperidinyl)-propoxy]-3-pyridine-carboximidoyl-chloride-maleate | +++ |
| 5,6-dihydro-5-(1-piperidinyl)-methyl-3-(piridyl)-4H-1,2,4-oxadiazine | +++ |
| 3-(3-piridyl)-5-[(1-piperidinyl)-methyl]-5,6-dihydro-6H-1,4,2-dioxazine-(Z)-2-butenedioate(1:1) | ++ |
| N-[2-hydroxy-3-(1-piperidinyl)-propoxy]-benz-imidoyl-chloride monohydrochloride | + |
| N-[2-hydroxy-3-(1-piperidinyl)-propoxy]-N',N'-diethyl-3-pyridine-carboximidamide monohydrochloride | +++ |

TABLE 2-continued

Stimulatory effect of hydroxylamine-derivatives by the invention on the heat stress induced HSP72 production in 3T3 cells if treatment precedes stress exposure.

| Compounds | HSP72 level relative to the stress exposed control |
|---|---|
| 3-(3-piridyl)-5-diethylaminomethyl-5,6-dihydro-6H-1,4,2-dioxazine hydrochloride | + |
| 3-phenyl-5-[(1-piperidinyl)-methyl]-5,6-dihydro-6H-1,4,2-dioxazine hydrochloride | ++ |
| /R/(+)-N-[2-hydroxy-3-(1-piperidinyl)-propoxy]-3-pyridine-carboximidoyl-chloride-(Z)-2-butenedioate(1:1) | +++ |
| (−)N-[2-hydroxy-3-(1-piperidinyl)-propoxy]-3-pyridine-carboximidoyl-chloride-(Z)-2-butenedioate(1:1) | +++ |
| N-[2-hydroxy-3-(piperidinyl)-propoxy]-naphtalene-1-carboxamide | +++ |
| 3-(3-piridyl)-5-t-butylamino-5,6-dihydro-6H-1,4,2-dioxazine | + |
| N-(2-hydroxy-3-piperidino-propoxy)-ethylurethane | + |
| N-[2-palmitoyloxy-3-(1-piperidinyl)-propoxy]-3-pyridine-carboximidamide monohydrochloride | +++ |
| N-[2-hydroxy-3-(1-piperidinyl)-propoxy]-N'-propyl-urea | +++ |
| N-(3-chloro-phenyl)-N'-[2-hydroxy-3-(1-piperidinyl)-propoxy]-urea | +++ |
| N-(3-piperidino-1-propoxy)-3-pyridine-carboximidoyl-chloride dihydrochloride | +++ |
| O-(3-diethylamino-propoxy)-3-pyridine-carboximidoyl-chloride hydrochloride | +++ |
| O-(3-piperidino-propyl)-3-nitro-benzhydroximoyl-chloride hydrochloride | +++ |
| 1-{[3-(t-butylamino)-2-hydroxy-propoxy]-imino}-1-(m-trifluoromethyl-phenyl)-ethane acetate | +++ |
| N-[2-hydroxy-3-(1-piperidinyl)-propoxy]-benzylurethane | 0 |
| N'-[2-hydroxy-3-(1-methyl-1-piperidinillm-1-yl)-propoxy]-N-methyl-piridinium-3-carboximidoyl-chloride diiodide | +++ |
| N-hexyl-N'-[3-(1-piperidinyl)-propoxy]-urea | ++ |
| N-cyclohexyl-N'-[2-acetoxy-3-(1-piperidinyl)-propoxy]-urea hydrochloride | 0 |
| N-[2-hydroxy-3-(1-piperidinyl)-propoxy]-2-nitro-benzimidoyl-chloride monohydrochloride | +++ |
| N-[2-hydroxy-3-(1-piperidinyl)-propoxy]-3-quinoline-carboximidamide dihydrochloride | +++ |
| N-[2-hydroxy-3-(1-piperidinyl)-propoxy]-N,N'-diphenyl-benzamidine | 0 |
| N,N-dimethyl-N'-[2-hydroxy-3-(1-piperidinyl)-propoxy]-N''-phenyl-guanidine | 0 |
| N,N-dimethyl-N'-phenyl-N''-[3-(1-piperidinyl)-propoxy]-guanidine hydrochloride | ++ |
| N-methyl-N-[3-(1-piperidinyl)-propoxy]-benzamide hydrochloride | + |
| 5,6-dihydro-3-(4-chloro-phenyl)-5-[N-methyl-piperidinium-1-E1]-methyl-4H-1,2,4-oxadiazine iodide | ++ |
| Methyl-{N-[3-(1-piperidinyl)-propoxy]}-3-pyridine-carboximidate maleate | 0 |
| N-methyl-N-[3-(1-piperidinyl)-propoxy]-m-trifluoromethyl-benzamide hydrochloride | +++ |
| N-[3-(I-piperidinyl)-propoxy]-N'-tetramethylene-3-pyridine-carboxamidine hydrochloride | +++ |
| N-[3-(I-piperidinyl)-propoxy]-N-methyl-N'-(n-hexyl)-urea | 0 |

TABLE 3

Stimulatory effect of hydroxylamine-derivatives by the invention on the heat stress induced HSP72 production in 3T3 cells if treatment followed stress exposure.

| Compounds | HSP72 level relative to the stress exposed control |
|---|---|
| N-[2-hydroxy-3-(1-piperidinyl)-propoxy]-3-pyridine-carboximidoyl-chloride-maleate | 0 |
| N-[2-hydroxy-3-(1-piperidinyl)-propoxy]-2-nitro-benzimidoyl-chloride monohydrochloride | 0 |
| 5,6-dihydro-5-(1-piperidinyl)-methyl-3-(3-piridyl)-4H-1,2,4-oxadiazine | 0 |
| O-(3-piperidino-propyl)-3-nitro-benzhydroximoyl-chloride hydrochloride | + |
| N-[2-palmitoyloxy-3-(1-piperidinyl)-propoxy]-3-pyridine-carboximidamide monohydrochloride | + |
| N-hexyl-N'-hexyl-N'-2-hydroxy-3-(1-piperidinyl)-propoxy]-urea | +++ |
| N-[2-hydroxy-3-(1-piperidinyl)-propoxy]-naphtalene-1-carboxamide | ++ |
| N-[2-hydroxy-3-(1-piperidinyl)-propoxy]-4-pyridine-carboximidoyl-chloride-(Z)-butenedioate (1:1) | ++ |
| N'-[2-hydroxy-3-(1-methyl-1-piperidinium-1-yl)-propoxy]-N-methyl-piridinium-3-carboximidoyl-chloride diiodide | +++ |
| N-[2-hydroxy-3-(1-piperidinyl)-propoxy]-3-quinoline-carboximidamide dihydrochloride | +++ |

In the Table 0 indicates that the treatment altered by ±20% the stress induced hsp72 level in the cells, while +, ++, +++ indicate 21-50%, 51-100% and >100% increase in the hsp72 levels, respectively, relative to the level of the stress exposed control.

Experiments using heat shock on U-937 leukemia and L-929 mouse fibroblast cells were carried out similarly as described above, but drug treatments in these tests always preceded the heat stress. The compound N-[2-hydroxy-3-(1-piperidinyl)-propoxy]-3-pyridine-carboximidoyl chloride maleate was tested at the $10^{-5}$ M concentration under these experimental conditions.

The treatment resulted in a more than 50% increase in the heat stress induced hsp72 level.

2. Experiments with Stress Induced by Chemical Agent

These experiments were performed on HeLa, human epithelial and U-937, human leukemia cells using $HgCl_2$ to induce stress response. Drug treatment was carried out before cells were exposed to the stress. Test cultures were prepared and treatments were performed as in the experiments with the 3T3 cells. After the drug treatment cells were incubated at 37° C. for 15 min. than all the cultures except two (non stressed control) were exposed to 0.5 µg/ml concentration of $HgCl_2$ and the incubation was followed. The induced amount of hsp72 was measured 6 hours after the exposure to stress. The applied concentration of $HgCl_2$ resulted in 15-30% of maximal hsp72 level.

On HeLa cells N-[2-hydroxy-3-(1-piperidinyl)-propoxy-benzimidoyl-chloride monohydrochloride and N-[3-(1-piperidinyl)-propoxy]-3-nitro-benzimidoyl-chloride monohydrochloride increased by more than 20% and by more than 50%, respectively the stress induced hsp72 level.

On U-937 cells N-[2-hydroxy-3-(1-piperidinyl)-propoxy-3-pyridine-carboximidoyl-chloride maleate treatment enhanced by more than 20% the stress induced hsp72 level relative to the stress exposed control.

3. Experiments on Primary Tissue Explants

These experiments were performed on rat spleen and testicular tissue explants applying heat stress after treatment with the experimental compounds. Experiments on spleen suspension were carried out as follows.

Spleens of CFY rats weighing 200 g were removed aseptically, and were homogenized in 10% fetal bovine serum containing MEM culture medium. The concentration of the cell suspension was adjusted to 50-100 mg/5 ml.

Five ml cell suspension was given into each of the culture dishes of 6 cm of diameter and the explants were incubated for one hour in a 5% $CO_2$ containing humidified air at 37° C. then cultures were treated with the $10^{-5}$ M concentration of the test compounds. After further 15 min. incubation at 37° C. the cultures were exposed to heat shock at 43° C. for 30 min. in an incubator. The amount of the induced hsp72 was measured after a further 6 hours incubation at 37° C.

Results are presented in Table 4. and enhanced levels of hsp72 are scored by the same scale as in Table 2. and 3.

TABLE 4

Stimulatory effect of hydroxylamine-derivatives by the invention on the heat stress induced hsp72 expression in rat spleen explant

| Compounds | Level of hsp72 relative to the stress exposed control |
|---|---|
| N-{3-[(1,1-dimethyl-ethyl)-amino]-2-hydroxy-propoxy}-3-trifluoromethyl-benzamide | + |
| N-[2-hydroxy-3-(1-piperidinyl)-propoxy]-N'-heptyl-urea | +++ |
| N-(3-chloro-phenyl)-N'-[2 hydroxy-3-(1-piperidinyl)-propoxy]-urea | +++ |
| 5,6-dihydro-5-(1-piperidinyl)-methyl-3-(3-piridyl)-4H-1,2,4-oxadiazine | 0 |

Experiments on rat testicular explant were performed as follows.

Testis of CFY rats weighing of 200 g were removed in sterile conditions and the released testicular tubuli were suspended in 10% fetal bovine serum containing MEM culture medium in that way that five ml suspension contained 50-100 mg tissue. The explants were incubated in 5% $CO_2$ containing humidified air at 37° C. for one hour, then the cultures were treated with $10^{-5}$ M concentration of the tested compounds. After a further incubation for 15 min. at 37° C., explants were exposed to heat shock at 43° C. for 30 min. The amount of the induced hsp72 was measured after a further 6 hours incubation at 37° C.

Results are summarized in Table 5. and the increase in hsp72 level is scored by the same scale as in Table 4.

TABLE 5

Stimulatory effect of hydroxylamine-derivatives by the invention on the heat stress induced hsp72 expression in rat testicular explant

| Compounds | Level of hsp72 relative to the stress exposed control |
|---|---|
| N-[2-hydroxy-3-(1-piperidinyl)-propoxy]-3-pyridine-carboximidoyl-chloride maleate | +++ |
| 5,6-dihydro-5-(1-piperidinyl)-methyl-3-(3-piridyl)-4H-1,2,4-oxadiazine | ++ |
| N-[2-hydroxy-3-(1-piperidinyl)-propoxy]-benzimidoyl-chloride monohydrochloride | +++ |
| N-{3-[(1,1-dimethyl-ethyl)-amino]-2-hydroxy-propoxy}-3-trifluoromethyl-benzamide | 0 |
| N-[2-benzyloxy-3-(1-piperidinyl)-propoxy]-3-pyridine-carboximidoyl-chloride-(Z)-2-butenedioate (1:1) | ++ |
| 3-(3-piridyl)-5-diethylaminomethyl-5,6-dihydro-6H-1,4,2-dioxazine hydrochloride | ++ |
| N-[2-hydroxy-3-(1-piperidinyl)-propoxy]-4-acetamido-benzamidine monohydrochioride | 0 |
| 3-(3-piridyl)-5-t-butylamino-5,6-dihydro-6H-1,4,2-dioxazine | 0 |
| N-[2-palmitoyloxy-3-(1-piperidinyl)-propoxy]-3-pyridine carboximidamide monohydrochloride | 0 |
| N-hexyl-N'-[2-hydroxy-3-(1-piperidinyl)-propoxy]-urea | 0 |
| N-(3-piperidino-1-propoxy)-3-pyridine-carboximidoyl-chloride dihydrochloride | ++ |
| O-(3-diethylamino-propoxy)-3-pyridine-carboximidoyl-chloride hydrochloride | 0 |
| O-(3-piperidino-propyl)-3-nitro-benzhydroximoyl-chloride hydrochloride | ++ |
| 1-{[3-(t-butylamino)-2-hydroxy-propoxy]-imino}-1-(m-trifluoromethyl-phenyl)-ethane acetate | + |
| N-{3-[1,1-dimethyl-ethyl)-amino]-2-hydroxy-propoxy}-3-trifluoromethyl-benzimidoyl-chloride monohydrochloride | + |
| N-[3-(diethylamine)-2-hydroxy-propoxy]-3-trifluoromethyl-benzimidoyl-chloride monohydrochloride | + |
| N-[2-palmitoyloxy-3-(1-piperidinyl)-propoxy]-3-pyridine carboximidoyl-chloride dihydrochloride | +++ |
| N-hexyl-N'-[3-(1-piperidinyl)-propoxy]-urea | 0 |
| N-[2-hydroxy-3-(1-piperidinyl)-propoxy]-3-nitro-benzimidoyl-chloride monohydrochloride | + |
| N-[2-hydroxy-3-(1-piperidinyl)-propoxy]-2-nitro-benzimidoyl-chloride monohydrochloride | ++ |
| N-[2-hydroxy-3-(1-piperidinyl)-propoxy]-N'-heptyl-urea | ++ |
| N-[2-hydroxy-3-(1-piperidinyl)-propoxy]-1-isoquinoline-carboximidamide dihydrochloride | +++ |
| N-methyl-N-[3-(1-piperidinyl)-propoxy]-benzamide hydrochloride | + |
| 5,6-dihydro-3-(4-chloro-phenyl)-5-[N-methyl-piperidinium-1-yl]-methyl-4H-1,2,4-oxadiazine iodide | + |
| N-[3-(1-piperidinyl)-propoxy]-tiophene-2-carboximidoyl-chloride-hydrochloride | ++ |

Measurement of the Level of HSP mRNA in the Thoracic Aorta of Rats with Genetic Hypertension Rats with genetic hypertension were divided into four groups of four. The groups were treated daily, orally, the first group with physiological saline, the second group with N-[2-hydroxy-3-(1-piperidinyl)]-propoxy-3-pyridine-carboximidoyl-chloride maleate (20 mg/kg) for 8 days, the third group with N-[2-hydroxy-3-(1-piperidinyl)-propoxy]-benzimidoyl-chloride monohydrochloride (5 mg/kg) for 20 days and the fourth group with N-[2-hydroxy-3-(1-piperidinyl)-propoxy]-2-thiophenecarboximidoyl-chloride monohydrochloride (5 mg/kg) for 20 days. Animals were sacrificed, aortas were isolated, snap frozen in liquid nitrogen and were stored at −70° C. till they were used.

a) Morphological Examination of the Thoracic Aorta

The examination was performed according to published methods (Br. J. of Pharmacol., 1995; 115, 515-420). A 1 mm² area of the thoracic aorta was excised and fixed in 2.5% glutaral-dehyde at room temperature. Post fixation was performed in 1% osmium-tetroxide for one hour. The tissue was dehydrated in ethanol and was embedded in Durcupan ACM. Pictures were taken by a Hitachi 7100 electronmicroscope and were evaluated qualitatively.

It was observed that the N-[2-hydroxy-3-(1-piperidinyl)-propoxy]-3-pyridine-carboximidoyl-chloride maleate and N-[2-hydroxy-3-(1-piperidinyl)-propoxy]-benzimidoyl-chloride monohydrochloride and N-[2-hydroxy-3-(1-piperidinyl)-propoxy]-2-tiophenecarboximidoyl-chloride monohydrochloride treatment facilitated the regeneration of the cells of aorta on an average and strong fashion, respectively.

b) Quantitative Measurement of hsp70

Experiments were carried out by the quantitative reverse transcription polymerase chain reaction. The principle of the method is that if two very similar, but distinguishable templates are amplified in the same PCR reaction then the ratio of the their products is not changed during the process. When the initial amount of one of the templates is known and the relative amount of the products is measurable then the amount of the unknown initial template can be calculated. In the most frequently used method the known template (competitor) and the unknown template (target) differ only in the length, the competitor is shorter, consequently the PCR products are separable based on their size.

RNA was isolated from the tissues by a guanidinium-isocyanate method (Chomczynski P. and Sacci N.: Anal Biochem. 162: 156, 1987). The concentration and the quality of the nucleic acid were evaluated by spectrophotometer and by agarose gel electrophoresis in denaturing condition (Shambrook J. et al.: Molecular Cloning. A Laboratory Manual, Cold Spring Harbour Laboratory Press, 1989). The isolated RNA was stored at −70° C.

A fragment was constructed from a hsp-70 gene coding cDNA by splicing out an internal sequence (PCR-splicing, Riedy M C et al.: Biotechniques 18: 70, 1995). The fragment was amplified by primers specifically bind to the external part of the construct (Erlich A.: PCR Technology, Principles and Applications for DNA Amplification. Stockton Press, 1989) and after measuring the concentration of the product it was stored at −70° C.

The reverse transcription was performed by standard conditions using 1 μg isolated RNA/sample with the help oligo dT (dTI6) primer. (Shambrook J. et al., the same as above).

Equal amount of cDNAs, prepared from RNA samples were mixed with various amounts of synthetic competitor (derived from 3, 10 times serial dilutions) and the templates were amplified by polymerase chain reaction. The temperatures applied during the cycles were the followings: denaturation (95° C., 1 min.), annealing (58° C. 1 min.), synthesis (72° C., 0, 5 min.).

After PCR amplification the products were separated on agarose gel (1%) and were stained by ethidium-bromide under standard conditions. (Sambrook et al., the same as above). The stained DNA fragments were visualized by UV-translumiator for photography. The amount of the PCR products was measured by densitometry from the negatives of the photos.

It was observed that the hsp-70 level in the thoracic aorta of the N-[2-hydroxy-3-(1-piperidinyl)-propoxy]-pyridine-carboximidoyl-chloride maleate, N-[2-hydroxy-3-(1-piperidinyl)propoxy]-benzimidoyl-chloride monohydrochloride and N-[2-hydroxy-3-(1-piperidinyl)-propoxy]-2-tiophene-carboximidoyl-chloride-monohydrochloride treated rats was more than 50% higher than the hsp-70 in the control animals.

Examination of the Inhibitory Effect on the Aging of Guinea Pig Skin

The inhibitory effect of the compounds, according to the invention, on the aging of the skin was examined in guinea pig. The skin of five animals per group was depilated and an 1 $cm^2$ area was irradiated from a UV-B source of 100 $mJ/cm^2$ of intensity on both sides. After the irradiation one side of the skin was treated with a cream composed according to the example 10 and containing 5% (w/w) of N-[2-hydroxy-3-(1-piperidinyl)-propoxy]-3-pyridine-carboximidoyl-chloride maleate or N-[2-hydroxy-3-(1-piperidinyl)-propoxy]-benzimidoyl-chloride monohydrochloride or N-[2-hydroxy-3-(1-piperidinyl)-propoxy]-2-nitro-benzimidoyl-chloride-monohydrochloride while the other side of the animals was treated with the same cream without the active ingredient. This was a self-controlled experiment.

The treatment started immediately after the irradiation and was performed twice daily for two weeks.

The UV-B irradiation resulted in a severe skin injury (vesicle, bull, injury of the epithelium, and wound formation) which healed 4 days earlier and the size of the wound was significantly smaller if the animals were treated with compounds according to the invention. The compounds facilitated the formation of the epithelium.

The experiment shows that the treatment increased the resistance of the skin against the UV-B irradiation and improved the regeneration of the skin.

Chemical Structures of compounds referenced in specification:

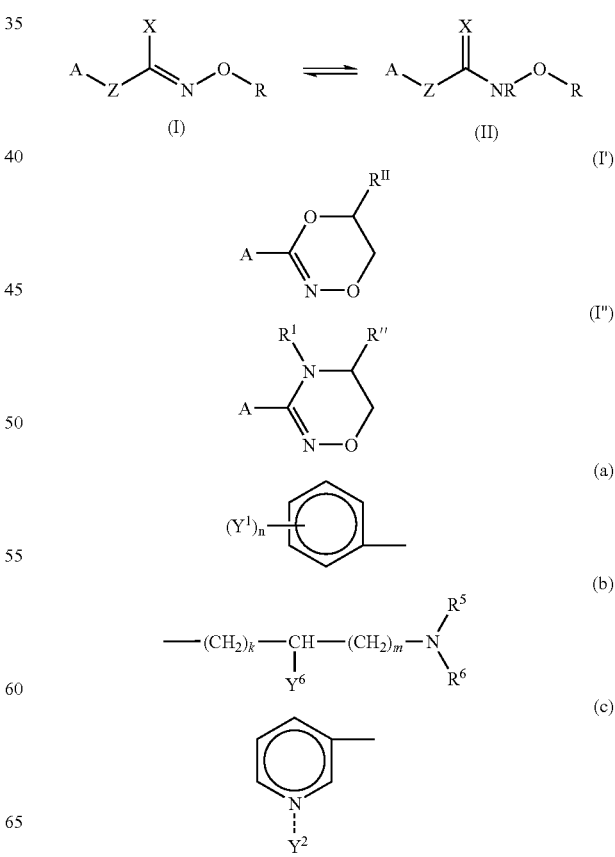

-continued

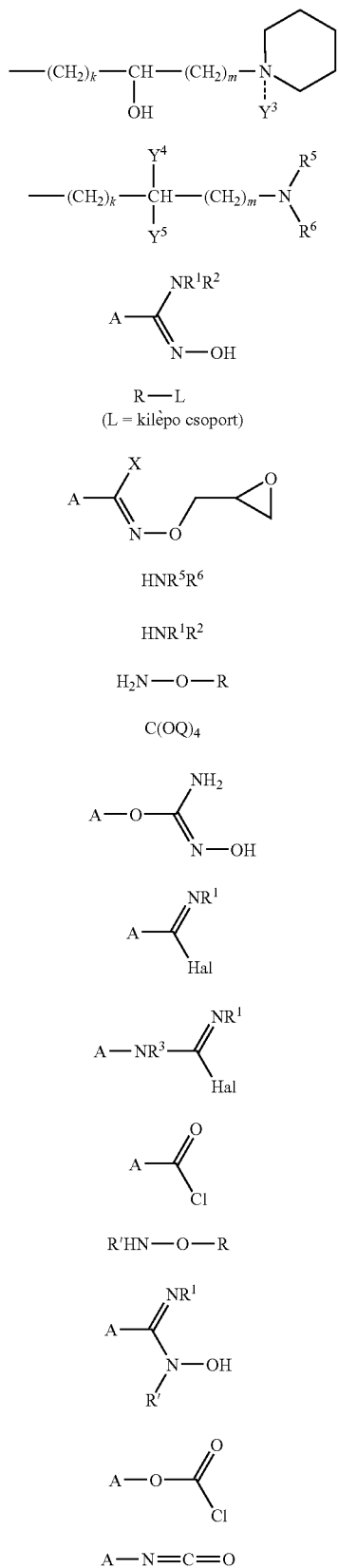

(d) 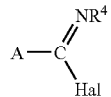

(e)

What is claimed is:

1. A method of treating a condition selected from an epithelial disease of renal tubules, atherosclerosis, coronarial disease, pulmonary hypertonia, cerebrovascular ischemia, stroke, and traumatic head injury in a mammal, comprising administering to said mammal a chemical compound, represented by formula (I"), or a salt thereof or an optically active stereoisomer thereof, wherein
R" is alkyl or substituted alkyl,
A is unsubstituted or substituted aryl or heteroaryl, and
$R^1$ is H, unsubstituted or substituted straight or branched alkyl.

2. The method of claim 1 wherein the mammal is a human organism.

3. The method of claim 1, wherein A is phenyl, phenyl substituted with one or more alkyl, halo alkoxy, haloalkyl or nitro, or naphthyl or N-containing heteroaryl which may be condensed with a benzene ring, or an S-containing or O-containing heteroaryl.

4. The method of claim 3, wherein A is an N-containing heteroaryl.

5. The method of claim 1, wherein R" is ω-amino-alkyl which may be substituted on the amino and/or alkyl chain, and wherein the alkyl chain has 1 to 5 carbon atoms.

6. The method of claim 5, wherein R" is an ω-amino-alkyl mono- or disubstituted on the amino, and wherein the amino substituent or substituents, independently, are one or two straight or branched alkyl or cycloalkyl, or the two amino substituents, together with the nitrogen atom attached thereto, form a 3- to 7-membered saturated hetero ring, which may contain additional heteroatoms.

7. The method of claim 1, wherein the chemical compound of formula (I") is 5,6-dihydro-5-(1-piperidinyl)-methyl-3-(3-pyridyl)-4H-1,2,4-oxadiziane.

8. The method of claim 1 or 7, wherein the condition is selected from artherosclerosis, coronarial disease, pulmonary hypertonia, cerebrovascular ischemia, stroke, and traumatic head injury.

9. The method of claim 8, wherein the condition is selected from artherosclerosis, coronarial disease, cerebrovascular ischemia, and stroke.

10. The method of claim 1, wherein one or more cells of the mammal have been exposed to a physiological stress, cell membrane injury, or cell organellum injury.

11. The method of claim 10, wherein the chemical compound is administered in an amount effective to increase the expression of a molecular chaperone by one or more cells of the mammal beyond an amount induced by the physiological stress, cell membrane injury, or cell organellum injury alone.

* * * * *